US011147900B1

(12) United States Patent
Hofmeister et al.

(10) Patent No.: US 11,147,900 B1
(45) Date of Patent: Oct. 19, 2021

(54) BIOMIMETIC NANOFIBER TISSUE SCAFFOLDS

(71) Applicant: ULTRA SMALL FIBERS, LLC, Wartrace, TN (US)

(72) Inventors: William H. Hofmeister, Nashville, TN (US); Robert A. Van Wyk, St. Petersburg, FL (US); Collin D. Anderson, Arlington Heights, IL (US)

(73) Assignee: ULTRA SMALL FIBERS, LLC, Wartrace, TN (US)

( * ) Notice: Subject to any disclaimer, the term of this patent is extended or adjusted under 35 U.S.C. 154(b) by 0 days.

(21) Appl. No.: 17/244,908

(22) Filed: Apr. 29, 2021

(51) Int. Cl.
*A61L 27/18* (2006.01)
*A61L 27/56* (2006.01)
*C08J 5/18* (2006.01)
*A61L 33/00* (2006.01)

(52) U.S. Cl.
CPC .............. *A61L 27/18* (2013.01); *A61L 27/56* (2013.01); *A61L 33/0041* (2013.01); *A61L 33/0082* (2013.01); *C08J 5/18* (2013.01); *A61L 2300/414* (2013.01); *A61L 2300/42* (2013.01); *A61L 2300/604* (2013.01); *A61L 2430/36* (2013.01)

(58) Field of Classification Search
CPC .................... A61L 27/18; C08J 5/18
See application file for complete search history.

(56) References Cited

U.S. PATENT DOCUMENTS

| | | | |
|---|---|---|---|
| 3,354,022 A | 11/1967 | Johnson, Jr. | |
| 5,407,737 A | 4/1995 | Halterbeck | |
| 8,303,693 B2 | 11/2012 | Leung | |
| 8,652,229 B2 | 2/2014 | Ensor et al. | |
| 9,012,596 B2 | 4/2015 | Sung | |
| 9,069,244 B2 | 6/2015 | Korbrin | |
| 9,817,154 B2 | 11/2017 | Kawaguchi | |
| 9,964,782 B2 | 5/2018 | Huynh | |
| 10,159,926 B2 | 12/2018 | Hofmeister et al. | |
| 2013/0216779 A1 | 8/2013 | Hofmeiser et al. | |
| 2015/0093550 A1 | 4/2015 | Hofmeister | |
| 2015/0367380 A1 | 12/2015 | Kotov | |
| 2016/0222345 A1 | 8/2016 | Hofmeister | |
| 2016/0257857 A1 | 9/2016 | Sitti | |
| 2017/0072349 A1 | 3/2017 | Hofmeister | |
| 2017/0320057 A1 | 11/2017 | Hofmeister et al. | |
| 2018/0353883 A1 | 12/2018 | Konishi | |
| 2019/0314746 A1 | 10/2019 | Leung | |
| 2020/0306029 A1 | 10/2020 | Rocco | |

OTHER PUBLICATIONS

Chen, et al., Flexible, Aligned Carbon Nanotube/Conducting Polymer Electrodes for a Lithium-Ion Battery, Chem. Mater., 2007, 19, 6595-3597 (Year 2007).

Pushparaj, et al., Flexible energy storage devices based on nanocomposite paper, Proced. Natl. Acad. Sci., Aug. 21, 2007, vol. 104, No. 34, 13574-13577, www.pnas.org_cgi_doi_10.1073_pnas.0706508104 (Year: 2007).

Burton and Bhushan, "Hydrophobicity, Adhesion, and Friction Properties of nanopatterned Polymers and Scale Dependence for Micro- and Nanoelectromechanical Systems," Nano Letters, 2005, vol. 5, No. 8, pp. 1607-1613.

White, Y. et al., "Single-Pulse Ultrafast-laser machining of high aspect nano-holes at the surface of SiO2," Optics Express, 2008, vol. 16, No. 19, pp. 14411-14420.

HybriSlip product brochure, Grace Bio-Labs, http://www.gracebio.com/media/product/2010_HybriSlip_Product_Information_File_wo_price.pdf(2010) (downloaded Mar. 8, 2021) (Year:2010).

*Primary Examiner* — Kyle A Purdy
(74) *Attorney, Agent, or Firm* — Eric B. Fugett; Mark A. Pitchford; Pitchford Fugett, PLLC

(57) ABSTRACT

A biomimetic tissue scaffold for repairing an elongated tissue in need of repair can comprise a plurality of coiled flexible polymeric ribbons having a surface on which is formed an array of nanofibers, the ribbons forming a tubular body defining a first open end in which a first end of the elongated tissue is receivable, a second open end in which a second end of the elongated tissue is receivable, and a lumen extending between the first and second open ends.

16 Claims, 46 Drawing Sheets

BIOMIMETIC NANOFIBER TISSUE SCAFFOLDS

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

Not Applicable.

STATEMENT REGARDING FEDERALLY SPONSORED RESEARCH OR DEVELOPMENT

Not Applicable.

REFERENCE TO SEQUENCE LISTING OR COMPUTER PROGRAM LISTING APPENDIX

Not Applicable.

BACKGROUND OF THE INVENTION

Stem Cells and the Extracellular Matrix

The use of stem cells for regenerative treatment of injuries is now commonplace. Stem cells from bone marrow aspirate or other sources are frequently injected into knees as a treatment for arthritis. Embryonic stem cells derived from umbilical cord blood and tissue are introduced intravenously in an attempt to cure various chronic conditions. While these treatments may be beneficial for some conditions, their regenerative abilities are limited because they lack a physiologically structured extracellular matrix ("ECM"). This matrix surrounds cells and provides support and organization that allows the creation of organs and other tissue structures.

The ECM is more than a structural support network. The ECM is a highly complex structure that heavily influences the behavior of cells within the matrix. Cells respond to external signals received from the matrix, and provide signals to the matrix that cause the matrix to beneficially adapt. Cells bind to features of the ECM and significant chemical and mechanical signaling occurs between the ECM and the cell. In "outside-in" signaling, physical cues play a significant and, until recently, underappreciated role in cell fate. For stem cells, particularly human mesenchymal stem cells ("hMSCs"), these signals heavily influence the decision to either maintain their stem cell phenotype or differentiate towards a specified cell lineage.

Scaffolds of various types have been devised that function as a temporary substitute for the ECM so as to enable the regeneration of complex tissue structures. These scaffolds may have a variety of configurations and be formed of a wide range of bioabsorbable materials. Flexible scaffolds may be used for various applications including the reinforcement, support and augmentation of soft tissue, while more rigid structures are suitable for the regeneration of bone and cartilage.

The biomaterials community has been reorienting their design process towards generating an optimal scaffold that can reliably and reproducibly mimic the extracellular matrix, one of the primary environmental constituents that heavily influences cell fate.

The need for tissue scaffolds is evidenced by the number of patent applications filed wherein the subject is a tissue scaffold. The subject inventions are focused on creating constructs that temporarily perform the functions of an extracellular matrix. These applications address a myriad of ways of providing a structure to support cells and providing channels for their propagation. These inventions also address numerous ways of controlling aspects of the behavior of stem cells—their propagation, maintaining their "stemness", and their differentiation into desired cell types.

An effective tissue scaffold must be biomimetic. That is, it must mimic the structures and functions of the ECM. The scaffold must be biocompatible, immunologically inert, and provide an environment conducive to cellular growth, differentiation and propagation. Scaffolds for soft tissue repair may be made by a variety of methods. For instance, Smith and Nephew, Inc. (Andover, Mass.) markets a flexible scaffold for augmenting rotator cuff tissue. Their Regeneten™ BioInductive Implant scaffold is derived from highly purified bovine Achilles tendon. A similar product, the Allopatch HD™ by Conmed, Inc. (Utica, N.Y.), is made of human acellular dermal matrix. These two products are supplied as a sheet for conformal application to a tissue surface. Another scaffold with a tubular form, configured for the reconnection of severed nerves, Avance Nerve Graft™ by AxoGenis (Alachua, Fla.) is a processed human peripheral nerve allograft. The graft is decellularized while maintaining aspects of the ECM so as to provide a beneficial environment for the regrowth of nerve tissue.

The ECM is composed of collagen fibers that provide structural and biochemical support to cells. The cells attach to the matrix through fibrils with nanometer-scale diameters, the physical/mechanical properties of the fibrils (i.e. rigidity, spacing, among others) providing cues to the cells that are a factor in the determination of cell behavior. Prior art tissue scaffolds made of suitable polymeric materials attempt to mimic this environment. Among these are scaffolds made of fibrous materials. Microfibers or nanofibers are formed into highly porous constructs that provide interstitial spaces in which cells may propagate. Some take the form of sheet material in which long continuous fibers of random or controlled orientation form a non-woven mat or fabric. In other instances the scaffold may have a cylindrical or tubular configuration with the fibers aligned generally parallel to the axis of the scaffold. In these configurations cell propagation through the interstitial spaces favors the formation of elongate cells aligned with the scaffold axis.

The natural ECM in human tissue is mainly composed of proteoglycans and fibrous proteins, both with nanoscale structural dimensions. Studies have shown that scaffolds with nanoscale structures support cell adhesion and proliferation, and function better than their microscale counterparts.

Because nanofibers are comparable in scale to the fibrils of the ECM, nanofibers are a primary focus of tissue scaffold development efforts. A primary method for forming these nanofibers is electrospinning, a method that requires the use of high voltages and a flowing polymer solution containing solvents that evaporate during production. Jingwei in U.S. Pat. No. 9,655,995 describes methods for electrospinning nanofibers and forming tissue scaffolds therefrom for the treatment of damaged cadiac tissue. In the methods described, the electrospinning process requires electrical potentials in the 25 kV to 30 kV range and the close control of several process parameters. The rates of nanofiber production are low in the examples given. It is not an environmentally friendly process due to the solvents required.

Electrospinning produces an interconnected web (or mat) of continuous small fibers with length to diameter ratios generally 1,000,000:1 or greater.

When forming nanofibers by electrospinning, the nanofiber materials are limited to polymers that can be mixed with a solvent to achieve the properties required for the process. If there is retained solvent in the nanofibers, the behavior of cells within a scaffold formed therefrom may be adversely affected.

In electrospinning the fibers of a closely controlled diameter are deposited onto a substrate. The substrate may be a flat plate oriented normal to the axis of the origin of the solution stream. Alternatively, the substrate may be a rotating element with a cylindrical, conical or other radially symmetric shape, the axis of rotation being perpendicular to the axis of the solution stream. Or the substrate may be a rotating disc with the axis of rotation parallel to the axis of the solution stream. Each of these substrate forms allow the forming of fiber mats configured to achieve specific design objectives through optimizing the deposition pattern of the fibers. If translation of the substrate in a plane normal to the solution stream is added to any of the substrate configurations, the deposited fiber may be given a directionality. Indeed, the fiber mat may be formed with a predetermined pattern to achieve design objectives for a given application. Microfiber or nanofiber mats with a particular preferential orientation of the fibers are frequently referred to as "ordered", and in some cases an "ordered matrix", or "ordered construct". The "order" to which this refers, then, is that the elongate continuous fibers forming the mat do not have a random directionality, but rather have a greater portion oriented parallel to a first axis than to a second axis. This is a two-dimensional effect only since the fiber mat forms a thin sheet, frequently membrane-like.

Johnson in US 2014/0030315 describes methods for forming tissue scaffolds from electrospun nanofibers in which nanofibers forming the construct are aligned parallel to each other and form a sheet-like structure. Bellamkonda in U.S. Pat. No. 8,652,215 describes methods for electrospinning elongate sheets of nanofibers with a uniaxial orientation. Multiple elongate sheets so formed are then stacked one on another to from a three dimensional construct with the nanofibers aligned. This construct is then positioned within a polysulfone tubular nerve conduit to form a cylindrical nanofiber scaffold useful for the regeneration of nerve tissue when treating a severed peripheral nerve or other elongate tissue structure. The propagation of axons (nerve cells) is directed through interstitial spaces between the nanofibers, parallel to the axis of the scaffold.

Jackson et al., in U.S. Pat. No. 10,507,187 describe a peripheral nerve guide with a core of aligned nanofibers surrounded by a sheath of non-aligned nanofibers. The core nanofibers are seeded with pluripotent mesenchymal stem cells. Axons propagate in the interstitial spaces between the aligned nanofibers. The non-aligned nanofibers forming the sheath provide support to the aligned nanofiber core. Biochemical factors supplied by the stem cells enhance nerve regeneration.

While the nanofibers of the previously described prior art examples are of a scale similar to fibrous tissue forming the ECM, they do not provide a biomimetic structure. Cells populating any of the scaffolds previously described will propagate through interstitial spaces, and will attach to the scaffold, however, this attachment differs from attachment to the native ECM wherein collagen tendrils of the ECM form focal adhesions with cells within the ECM.

The propagation and differentiation of stem cells is affected by the geometric characteristics of a scaffold. In the case of fibrous scaffolds, the diameter of the fibers may affect the ability of the stem cells to attach to the fibers. The pore size and composition also affect stem cell behavior. For instance, native bone has a porosity of between fifty and ninety percent with an average pore size typically in the one millimeter range. Providing a scaffold with similar pore density and size favors the growth of osteocytes and vascularization. Smaller pores favor chondrocyte growth. Accordingly, there is an emphasis on manufacturing methods for scaffolds that allow control of the fiber diameter and density to achieve desired effects. The fabrication of polymer filaments on the scale of fibrous ECM elements (2-200 nm) is accomplished by electrospinning. As previously herein described, the electrospinning process forms long fibers of polymer solvent solution which are extruded at high (>10 kV) potential to a collector base plate that is traversed at a predetermined rate to form layers of fiber mat. The orientation of these long fibers is substantially random within planes parallel to the plane of the base plate. By controlling the parameters of the electrospinning process and movement of the collector, fiber size and density may be optimized for a given application. Patent JP 5,249,785 and U.S. Pat. No. 10,137,223 by Francis et. al. describe methods for forming electrospun scaffolds having a variety of configurations for treating, among other injuries, a severed or damaged nerve, muscle, or blood vessel, as well as a skin or other wound. These patents also describe methods of promoting differentiating of stem cells into osteoblasts, chondrocytes, ligaments or tendons, and muscle. Their method of differentiation, however, is primarily through culturing cells of a selected type in the scaffold, not through physical cues provided by the scaffold fibers.

Other scaffolds, not generally commercially available at this time, may be formed as a porous foam with controlled pore size and pore density. And researchers are also working on methods in which additional pores are created in a formed scaffold by laser drilling, or in which scaffolds are manufactured by 3D printing.

It should be understood that, while in some discussions of fibrous scaffolds the term "pore" is used, a "pore" is defined as "a minute opening in a surface". Scaffolds formed of fibrous mats do not have the requisite surfaces to have actual pores. The fiber diameter, density and average inter-fiber spacing of the fibers in a fibrous scaffold may be adjusted to favor a preferred cell behavior through control of the average cross-sectional area of the highly irregular channels for cell propagation. This may be considered an effective pore size.

Scaffolds with optimized fiber size, and effective pore size and density designed to achieve a desired effect on the propagation and differentiation of stem cells are frequently broadly referred to as "tuned" scaffolds or "tuned" arrays of fibers. Additionally, the term "tuned" is frequently applied to fibrous scaffolds in which the direction of the elongate continuous fibers have a preferred range of orientation in planes parallel to the basal plane of the scaffold. These "tuned" scaffolds may also have two or more discrete regions in which the porosity characteristics of each region are optimized to favor the differentiation of stem cells to favor, for example, osteocytes and chondrocytes. Frequently, scaffolds with these discrete regions with differing characteristics are also referred to as "biomimetic", that is mimicking a naturally occurring structure that favors stem cell propagation and differentiation to form structures within the body. In the case of scaffolds for treating osteochondral lesions, a scaffold that has at least a first portion with fiber diameter and fiber densities that mimic those of native bone, and a second portion with fiber diameter and densities that mimic those of the cartilaginous extracellular matrix would be considered biomimetic under the commonly used definition.

However, it must be noted that the fiber length in these "tuned" fibrous scaffolds is not controlled and therefore cannot be optimized for a given use. These elongate nanofibers may be aligned so as to favor the propagation of elongate cell structures in the interstitial spaces, however they lack ECM features for attachment and for "outside in" signaling that is a factor in affecting cell behavior. While these scaffolds may be referred to as tuned, they are only optimized for parameters that can be controlled in the manufacturing process. Indeed, the average density and effective pore size can only be controlled within broad ranges. Advantages that may be achieved through control of the length, orientation, and three-dimensional arrangement of fibers cannot be realized with current commonly used manufacturing techniques. Naturally occurring structures within the body are not limited in the way that these manufactured scaffolds are limited. Accordingly, while the manufactured scaffolds may be referred to as "biomimetic" in that they grossly mimic natural structures, their long continuous fibers, regardless of orientation, do not provide sites for cell attachment that mimic the tendrils of the ECM, and the focal attachments of the tendrils with their inherent ability to provide outside-in signaling to the cell, thereby affecting cell behavior.

There is a need for tissue scaffolds that more closely mimic the extracellular matrix in that they have features that mimic the tendrils of the ECM, that is, that provide nanofibers of finite length attached to structural elements of the scaffold in an arrangement that closely mimics the spacing of the ECM fibrils.

The development of advanced manufacturing methods that allow improved control of additional fiber characteristics and the three-dimensional arrangement of these fibers will enable the creation of scaffolds that achieve enhanced results through their ability to more closely approximate naturally occurring structures of the ECM.

BRIEF SUMMARY

The presently disclosed subject matter overcomes some or all of the above-identified deficiencies of the prior art, as will become evident to those of ordinary skill in the art after a study of the information provided in this document.

Scaffolds with enhanced biomimetic features formed using advanced manufacturing methods are the subject of the instant invention, along with methods for their use. Specifically, scaffolds of the present invention have patterned matrices ("arrays") of nanofibers that are spaced on the micron scale formed on elements of the scaffold, the nanofibers being similar in size and morphology to collagen fibrils universally found within mammalian cells. This biomimetic aspect of these scaffolds is enabled by an advanced manufacturing method and imparts beneficial properties unachievable in other, less biomimetic scaffolds.

In healthy, naturally occurring tissue the extracellular matrix is formed of many types of collagen. More specifically, the basement membrane is formed of highly cross-linked collagen IV, which is quite stiff, while Type II collagen fibrils constitute the bulk of hyaline cartilage. Type II collagen fibrils are flexible and are the primary conduits for chemokine and proteoglycan communication between cells. Focal adhesions formed by stem cells on Type II fibrils affect the behavior of stem cells through "outside in" signaling. One specific mechanical aspect of this is communication from the collagen forming the ECM to a stem cell is through the tendrils attached to a stiff matrix. Another is through the creation of shear stresses between the cell and the ECM. To create shear stress at the focal adhesions the tendrils must have not only sufficient tensile strength but a degree of rigidity. Here we come to the most overlooked aspect of biomimetic scaffolds. Many flexible Type II fibrils are anchored to and protrude from a stiff basement membrane. This stiffness gradient in Type II collagen is sensed by the cell and is a primary driver in cell mobility and an important cue in determining cell fate.

It will be understood that prior art scaffolds, while claiming to be "biomimetic" lack the fine complex features of the extracellular matrix that control cell adhesion, propagation and differentiation in the natural structure.

Scaffolds of the present invention mimic the tendril arrays present on the basement membrane of cross-linked collagen forming the ECM. This is accomplished by providing arrays of nanofibers formed on surfaces of the scaffold, the nanofibers of an array having a spacing similar to the collagen tendril attachment to a stiffer matrix of cross-linked fibers, and, like the tendrils, the nanofibers are substantially normal to the surface at the attachment site. The nanofibers may have somewhat irregular shapes in that they may have bumps, ridges, seams, and portions with asymmetric cross sections, however the nanofibers are generally tapered with a distally decreasing cross-section over their length. Each nanofiber may be viewed as a cantilevered beam with decreasing stiffness along its length, the greatest stiffness being adjacent to its attachment point to the surface. This allows secure attachment by cells through focal adhesions formed at the tips of the nanofibers, and also allows the creation of shear stresses between the scaffold and cells attached thereto. Additionally, nanofiber arrays of the present invention may provide outside-in signaling to cells within the scaffold that determine, for instance, the tendency of stem cells to maintain their "stemness" or to differentiate, and, in the case of differentiation, to increase the proclivity of the cells to differentiate to a preferred cell type.

Disclosed herein are biomimetic tissue scaffolds formed of elongate ribbon-like structures ("bioribbons") formed of a basal film upon a surface of which are formed nanofiber arrays. Scaffolds of the present invention are formed of a plurality of bioribbons on which are integrally formed nanofibers patterned on the micron scale over expanses of surfaces of the ribbon. Unlike the fibers of prior art scaffolds previously herein described, nanofibers of the present invention have a predetermined length and are oriented substantially normal to the basal plane of the ribbon. The fibers are generally tapered over their length so that the stiffest part of the fiber is adjacent to its attachment to the surface of the bioribbon. The fibers are arranged in ordered arrays (matrices) in which the nanofibers may be arranged in rows, the spacing of the nanofibers within a row and the spacing between rows being regular or irregular and predetermined by the manufacturing method used. Bioribbons of the present invention have an elongate flexibly planar base formed of a film of a suitable bioabsorbable material, with nanofiber arrays formed on a first surface thereof.

Biomimetic tissue scaffolds of the present invention may be formed by assembling a plurality of bioribbons, the bioribbons having formed on a surface thereon ordered matrices of nanofibers, the nanofibers and their arrangement in the arrays being configured to affect a desired tissue behavior. In some embodiments for forming sheet-like scaffolds, the bioribbons may be woven, either singly or from yarn made from multiple bioribbons (see, e.g., scaffold 2800 in FIG. 88). In other embodiments, the bioribbons are formed into a non-woven mat that may optionally be formed into a non-woven fabric held together by needling, by thermal or adhesive bonding, or other methods. In some embodiments the alignment of bioribbons forming the mat or fabric may be random. In others, a portion or all of the ribbons may have a preferential alignment. Some of the scaffolds are formed of bioribbons having a single nanofiber array configuration formed on all bioribbons of the construct, the nanofiber array being optimized to achieve specific cell behaviors. In other embodiments, scaffolds of the present invention may have a stratified construction with a first region having bioribbons with nanofiber arrays optimized for a first cell behavior, and a second region having bioribbons with nanofibers optimized for a second cell behavior. Indeed, scaffolds of the present invention may have multiple regions each with unique combinations of bioribbon configurations and alignments to achieve specific tissue regeneration objectives. For instance, a first portion of a scaffold for treatment of a wound may have a first proximal portion configured for optimal regeneration or regrowth of subsurface tissue, and a second distal portion configured for the regeneration or regrowth of dermal tissue.

Biomimetic scaffolds of the present invention may also be configured with cylindrical or tubular shapes, or as a scaffold with both cylindrical and tubular portions. As with the previously described sheet-type scaffolds, scaffolds with radial symmetry may be made of bioribbons with a single configuration and random or aligned construction. Alternatively, the scaffold may have a first portion with a first nanofiber array configuration and/or orientation for a first tissue effect, and a second nanofiber array and/or orientation for a second tissue effect. For instance, a scaffold for the regeneration of an elongate tissue structure may have a central cylindrical portion formed of a bundle of bioribbons oriented parallel to the axis of the scaffold so as to form interstitial spaces through which elongate cells may propagate, and a surrounding tubular portion formed of unaligned, or circumferentially aligned bioribbons, configured to bind the central bioribbon bundle and provide support to the structure. Bioribbons forming the aligned central bundle may have formed on them nanofiber arrays optimized for the propagation of a preferred elongate cell type along ribbon surfaces forming axially directed interstitial spaces. Bioribbons forming the tubular portion may have formed on them nanofiber arrays optimized for forming equiaxial cells or cells with another optimized shape for providing desired structural properties.

Bioribbons of the present invention may be cut into short ribbon segments that may be implanted into a wound. These segments may be combined with a suitable liquid so as to form a flowable scaffold that may be implanted by injection or through use of an instrument like a spatula packer. In some embodiments the liquid is platelet rich plasma (PRP) that may further include stem cells.

Indeed, scaffolds of the present invention, regardless of their configuration may be infused with stem cells, PRP or other biologics that enhance the healing response, and/or with cells of a chosen type for the tissue to be regenerated.

Scaffolds of the present invention may be beneficially used for the treatment of chronic wounds including pressure injuries, neuropathic (diabetic) foot ulcers, non-healing surgical wounds, and those due to venous insufficiency.

Scaffolds of the present invention may also be used for tissue augmentation. When a tendon or ligament is torn, the repair site is subject to re-injury during healing, and subsequent to healing due to the repaired region having insufficient strength. This may be avoided/minimized by augmenting the tissue at the repair site. This augmentation increases the strength of the repaired structure both during healing and after healing is complete. When implanting a tissue scaffold for tissue augmentation it is desirable that the scaffold have physical properties approximating those of the native tissue forming the structure into which the scaffold is implanted. Scaffolds of the present invention allow the strength, stiffness and resilience of the scaffold to be optimized through the physical dimensions of the bioribbons forming the scaffold without affecting the tuned topography of nanofiber arrays on the ribbon. Accordingly, scaffolds of the present invention may have optimal physical properties for an application and tuned nanofiber arrays that favorably affect tissue differentiation and propagation.

Bioribbons of the present invention with their nanofiber arrays are formed without the use of solvents or high voltage. Specifically, nanofiber arrays of the present invention may be formed in a molding process in which a suitable polymer, positioned between a first surface of a mold with an array of nanoholes formed therein and a surface of a second compressing element, flows into the nanoholes of the mold when a compressive force is applied to the polymer by the second element, the polymeric material being heated to a temperature sufficient to allow flow into the nanoholes. Subsequently, the polymeric material is cooled sufficiently so that when the compressing element is removed, the polymer with the attached molded nanofibers can be stripped from the mold surface. The result is a planar polymeric film portion with an array of nanofibers integrally formed on a first surface thereof, the form of the nanofiber array being complementary to nanohole array in the mold. The first surfaces of the mold and compressing element may be planar with the polymeric material introduced therebetween as a film prior to heating and material flow into the mold nanoholes. Alternatively, the mold and second compressing element may be rotating cylinders, the polymer in molten form being introduced onto the circumferential surface of the mold, and subsequently compressed between the mold and the cylindrical surface of the compressing element. This compression enhances the flow of the polymer into the nanoholes of the mold while simultaneously cooling the material so that it can be subsequently peeled from the mold. In other embodiments, molten polymer is applied to the cylindrical surface of a rotating cylindrical mold with the mold heated sufficiently to cause molten polymer to flow into the nanoholes due to surface tension effects without the use of a compressing element. The polymer is then cooled sufficiently by an air blast or other means to allow the film with attached nanofibers to be stripped from the mold. In yet other embodiments, an elongate film is applied to the rotating cylindrical mold. In one embodiment the film is heated sufficiently to soften the material and cause it to flow into the nanoholes with use of a compressing element. In another embodiment the film is heated sufficiently to soften the material and cause it to flow into the nanoholes due to surface tension effects only. In both cases, the polymer is subsequently cooled sufficiently to allow the film with the nanofiber arrays formed thereon to be stripped from the mold. Whether formed in discrete segments as when using a mold of planar geometry, or formed as elongate strips using the rotating cylindrical mold, the resulting film with ordered arrays of integral nanofibers formed thereon may be cut, slit, chopped or otherwise divided into bioribbons of the present invention.

In some embodiments bioribbons of the present invention are cut into short segments that may be formed into discrete scaffolds, suspended in a suitable gel to make a flowable scaffold material, or that may be applied to a wound site and retained in place by a dressing or other means.

DETAILED DESCRIPTION

Figure 1:
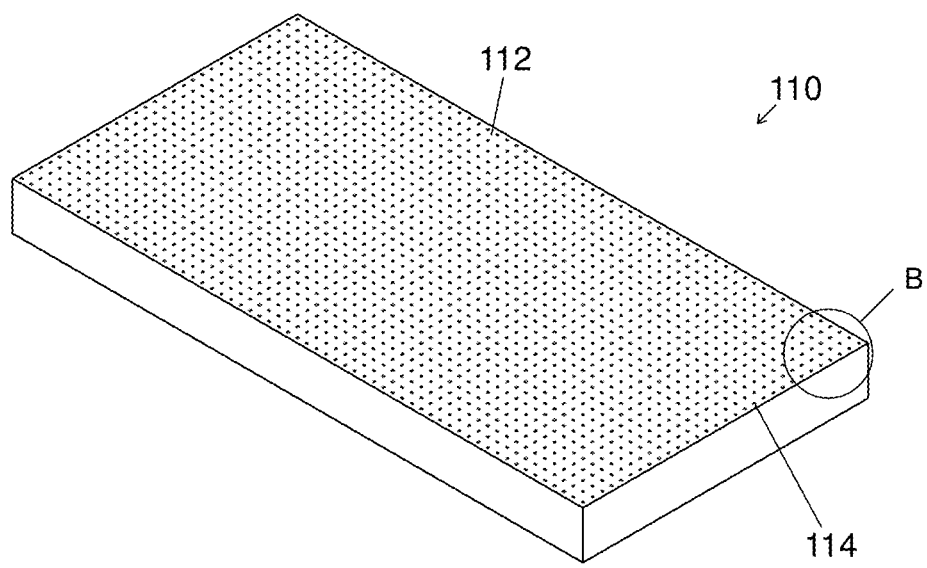
FIG. 1 is a perspective view of an embodiment of a mold for making embodiments of biomimetic scaffold materials of the present invention.
Figure 2:
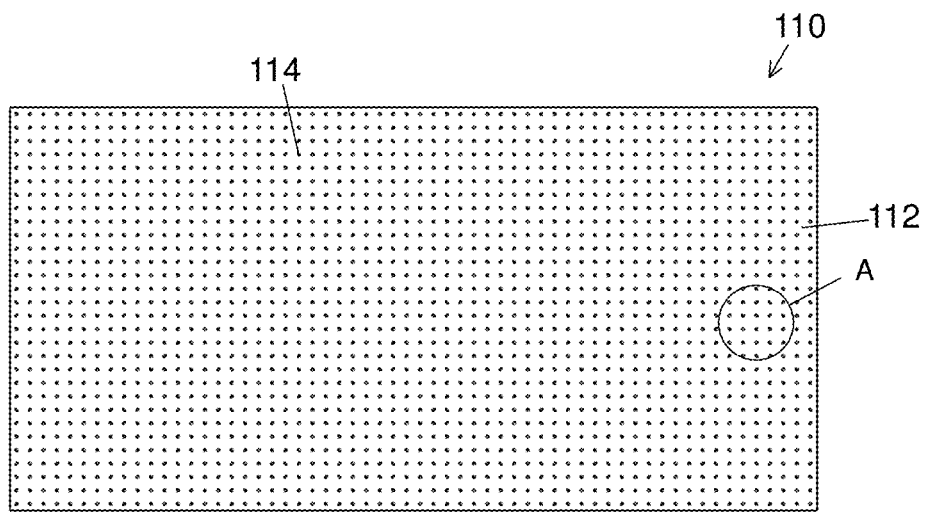
FIG. 2 is a plan view of the mold of FIG. 1.
Figure 3:
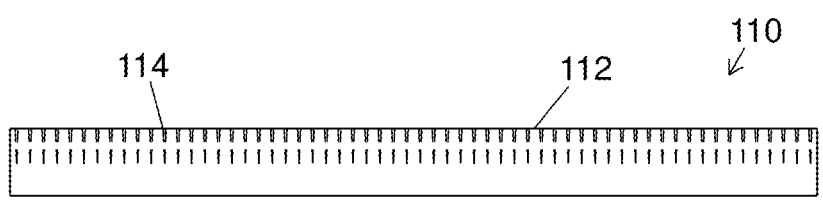
FIG. 3 is a side elevational view of the mold of FIG. 1.
Figure 4:
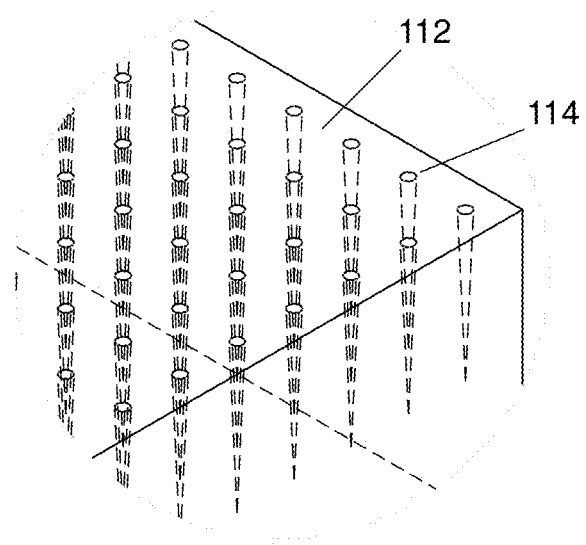
FIG. 4 is an expanded view of the mold of FIG. 1 at location B.
Figure 5:
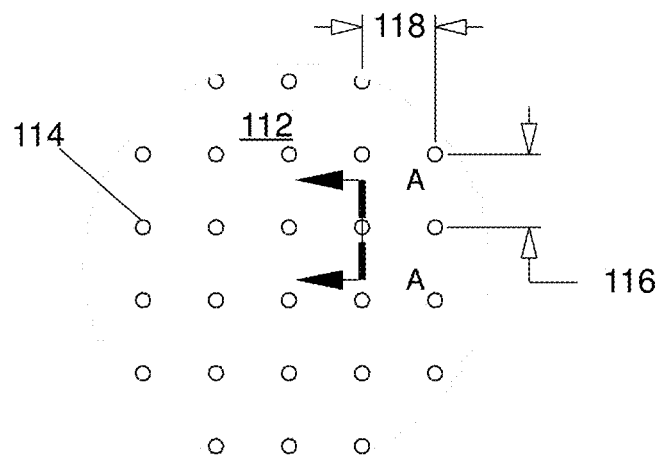
FIG. 5 is an expanded view of the mold of FIG. 2 at location A.
Figure 6:
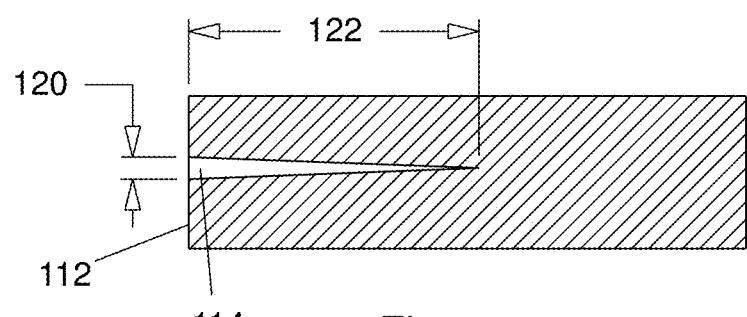
FIG. 6 is an expanded sectional view of the mold of FIG. 5 at location A-A.

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention.

To facilitate the understanding of the embodiments described herein, a number of terms are defined below. The terms defined herein have meanings as commonly understood by a person of ordinary skill in the portions relevant to the present invention. Terms such as "a," "an," and "the" are not intended to refer to only a singular entity, but rather include the general class of which a specific example may be used for illustration. The terminology herein is used to describe specific embodiments of the invention, but their usage does not delimit the invention, except as set forth in the claims.

The details of one or more embodiments of the presently disclosed subject matter are set forth in this document. Modifications to embodiments described in this document, and other embodiments, will be evident to those of ordinary skill in the art after a study of the information provided herein. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the subject matter disclosed herein.

Unless defined otherwise, all technical and scientific terms used herein have the same meaning as commonly understood by one of ordinary skill in the art to which the subject matter disclosed herein belongs. Although any methods, devices, and materials similar or equivalent to those described herein can be used in the practice or testing of the presently disclosed subject matter, representative methods, devices, and materials are now described.

The terms "a", "an", and "the" refer to "one or more" when used in this application, including the claims. Thus, for example, reference to "a cell" includes a plurality of such cells, and so forth. The use of the word "a" or "an" when used in conjunction with the term "comprising" in the claims and/or the specification may mean "one," but it is also consistent with the meaning of "one or more," "at least one," and "one or more than one."

All references to singular characteristics or limitations of the present disclosure shall include the corresponding plural characteristic(s) or limitation(s) and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and devices of the present disclosure, including components thereof, can comprise, consist of, or consist essentially of the essential elements and limitations of the embodiments described herein, as well as any additional or optional components or limitations described herein or otherwise useful.

Unless otherwise indicated, all numbers expressing physical dimensions, quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently disclosed subject matter.

As used herein, the term "about," when referring to a value or to an amount of mass, weight, time, volume, concentration, percentage or a physical dimension such as length, width, or diameter, is meant to encompass variations of in some embodiments ±20%, in some embodiments ±10%, in some embodiments ±5%, in some embodiments ±1%, in some embodiments ±0.5%, and in some embodiments ±0.1% from the specified value or amount, as such variations are appropriate to perform the disclosed methods.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The present disclosure relates to the inventor's demonstration that the patterned matrices of polymer nanofibers disclosed herein promote stemness and cell-cell interaction of stem cells. Accordingly, in some embodiments, the disclosure is directed to a novel tissue scaffold, that is, a temporary structure that provides an environment suitable for the regeneration of tissues and organs. Embodiments of a scaffold for promoting tissue growth may include a plurality of elongate ribbon-like structures (hereinafter referred to as "bioribbons" or simply "ribbons") formed of a polymer film and a patterned matrix of polymer nanofibers protruding from a surface thereof.

By the term "ribbon" it is generally meant a long thin strip of material. When used in reference to biomimetic scaffolds of the present invention, a bioribbon or ribbon refers to a narrow elongate strip of polymer film on which an ordered array of nanofibers has been formed integral to the film. A plurality of bioribbons of the present invention may be aligned and formed into a bundle or tubular structure so as to create a biomimetic scaffold for treating elongate tissue structures such as, for instance, tendons, ligaments, vessels or nerves. Alternatively, bioribbons may be formed into a sheet of woven or non-woven mat or fabric usable as a tissue scaffold for affecting the growth of tissue for the purpose of creating or augmenting tissue of a structure like, for instance, skin, rotator cuff, or myocardial tissue. Scaffolds created of bioribbons of the present invention form a structure that temporarily mimics the extracellular matrix during tissue regeneration. Spaces formed between ribbons of scaffolds of the present invention create passages for tissue propagation and the supply of nutrients.

The polymer film from which bioribbons are formed can be any bioabsorbable thermoplastic polymer. Examples of suitable bioabsorbable thermoplastic polymers include epsilon-polycaprolactone (PCL), polyglycolic acid (PGA), polylactic acid (PLA), polydioxanone (PDS), and copolymers of PGA and PLA, among others.

By the term "patterned" it is generally meant that the polymer nanofibers disclosed herein are arranged or ordered into a user-defined pattern or array. In some embodiments, the term "patterned" can refer to the spacing of polymer nanofibers on a lamella. On a substantially flat structure, such as a polymer film forming a bioribbon, the nanofibers disclosed herein can be spaced along an X-axis and a Y-axis at the same or different intervals along either axis. In some embodiments, nanofibers can be spaced about 50 microns, 40 microns, 30 microns, 20 microns, 10 microns, 9 microns, 8 microns, 7 microns, 6 microns, 5 microns, 4 microns, 3 microns, 2 microns, or 1 microns apart on an X-axis and about 50 microns, 40 microns, 30 microns, 20 microns, 10 microns, 9 microns, 8 microns, 7 microns, 6 microns, 5 microns, 4 microns, 3 microns, 2 microns, or 1 micron apart on a Y-axis The term "matrix" as used herein refers generally to a structure or environment in which living cells can be cultured and "patterned matrix" refers to a matrix with engineered order. For example, a patterned matrix of polymer nanofibers can include a plurality of standing polymer nanofibers with user-defined physical dimensions arranged in one or more arrays according to user-defined spatial parameters. Patterned matrices forming biomimetic scaffolds of the present invention may be optimized (tuned) to facilitate desired cellular behavior. User-tunable parameters include fiber spacing, diameter (also sometimes referred to herein as "width"), height (also sometimes referred to herein as "length"), and number of fibers per unit of surface area (also referred to herein as "fiber surface area density").

In some embodiments, a patterned matrix of polymer nanofibers can include nanofibers having an average length of at least 10.00 microns. In certain embodiments, the nanofibers can have a length of from about 10.00 microns to about 60.00 microns. In an exemplar embodiment, the nanofibers can have an average length of from about 15.00 microns to about 35.00 microns. In specific embodiments, the nanofibers can have a length of about 10.00 microns, 11.00 microns, 12.00 microns, 13.00 microns, 14.00 microns, 15.00 microns, 16.00 microns, 17.00 microns, 18.00 microns, 19.00 microns, 20.00 microns, 21.00 microns, 22.00 microns, 23.00 microns, 24.00 microns, 25.00 microns, 26.00 microns, 27.00 microns, 28.00 microns, 29.00 microns, 30.00 microns, 31.00 microns, 32.00 microns, 33.00 microns, 34.00 microns, 35.00 microns, 36.00 microns, 37.00 microns, 38.00 microns, 39.00 microns, 40.00 microns, 41.00 microns, 42.00 microns, 43.00 microns, 44.00 microns, 45.00 microns, 46.00 microns, 47.00 microns, 48.00 microns, 49.00 microns, 50.00 microns, 51.00 microns, 52.00 microns, 53.00 microns, 54.00 microns, 55.00 microns, 56.00 microns, 57.00 microns, 58.00 microns, 59.00 microns, or 60.00 microns.

In some embodiments, a patterned matrix of polymer nanofibers can include nanofibers having an average diameter of from about 0.10 microns to about 1.20 microns. In an exemplar embodiment, the nanofibers can have an average diameter of 0.24 microns to 0.34 microns. In certain embodiments, the nanofibers can have an average diameter of about 0.10 microns, 0.15 microns, 0.20 microns, 0.25 microns, 0.26 microns, 0.27 microns, 0.28 microns, 0.29 microns, 0.30 microns, 0.31 microns, 0.32 microns, 0.33 microns, 0.34 microns, 0.35 microns, 0.40 microns, 0.45 microns, 0.50 microns, 0.55 microns, 0.60 microns, 0.65 microns, 0.70 microns, 0.75 microns, 0.80 microns, 0.85 microns, 0.90 microns, 0.95 microns, 1.00 microns, 1.05 microns, 1.10 microns, 1.15 microns, or 1.20 microns.

The nanofiber lamella surface area density can range from about 1 to about 30 nanofibers per 100 microns$^2$. In some embodiments, the nanofiber surface area density can range from about 6 to about 25 nanofibers per 100 microns$^2$. In specific embodiments, the nanofiber surface density is about 6, 7, 8, 9, 10, 11, 12, 13, 14, 15, 16, 17, 18, 19, 20, 21, 22, 23, 24, or 25 nanofibers per 100 microns$^2$. In an exemplar embodiment, the nanofiber surface area density is about 16.7 nanofibers per 100 micron.

In certain embodiments, a matrix of polymer nanofibers is configured to modulate gene expression in stem cells cultured on or recruited to the scaffold relative to control cells cultured in the absence of the matrix. As used herein, "modulate gene expression" refers to increasing or decreasing the expression of one or more genes encoding a polypeptide involved in cell self-renewal or cell-cell interaction, alone or in combination with other transcription and/or translational regulatory factors or nucleic acids encoding such a polypeptide. As used herein, the term "stem cell" can be any type of undifferentiated cell of a multicellular organism that is capable of giving rise to more cells of the same type, and from which certain other kinds of cell arise by differentiation. Stem cells can be either embryonic or adult stem cells. In an exemplar embodiment, the stem cells are human mesenchymal stem cells. The terms "culture" and "cultured" as used herein refer to the cultivation or maintenance of cells under conditions suitable for growth.

In specific embodiments, the patterned nanofiber matrix is configured to increase expression in cells cultured on or recruited to the matrix of a nucleic acid encoding a self-renewal transcription factor polypeptide or a cell-cell interaction marker polypeptide relative to control cells cultured in the matrix.

The terms "polypeptide" refers to a polymer of amino acids, or amino acid analogs, regardless of its size or function. Exemplary polypeptides include gene products, naturally occurring proteins, homologs, orthologs, paralogs, fragments and other equivalents, variants, and analogs of the foregoing.

A preferred method for manufacturing herein described ribbons and ribbon segments of the present invention with nanofiber arrays for bioribbons of the present invention is hot pressing, a casting method in which a suitable polymeric film is positioned between a temperature controlled compressing plate and a substrate/mold formed of silica or another suitable material in which patterns of nanoholes have been formed, the pattern of the nanoholes being complementary to the pattern of nanofibers to be produced.

Referring now to FIGS. 1 through 6, mold 110, formed of silica or another suitable transparent material, has a first planar surface 112 in which are formed a plurality of nanoholes 114, nanoholes 114 being formed in a predetermined pattern. Each nanohole 114 is formed by a single femto-second laser pulse. Methods for making molds with patterns of nanoholes formed therein by single-pulse femtosecond laser machining are described in detail in US 2015/0093550, herein incorporated by reference in its entirety. Nanoholes 114 are spaced distance 116 apart in a first direction, and distance 118 in a second direction perpendicular to first direction 116. In some embodiments distances 116 and 118 are equal. In others they are not. Holes 114 have a first diameter 120 at its intersection with surface 112, and a depth 122.

Suitable materials for mold 110 are transparent materials like borosilicate glass, soda lime glass, BK7 optical glass, plastic, single-crystal quartz, diamond and sapphire. All have been successfully micromachined with femtosecond laser pulses. Fused silica is a preferred material since it offers a combination of properties like wide range of spectral transparency, low autofluorescence, good biocompatibility, chemical inertness, near zero thermal expansion, excellent thermal shock resistance, and low dielectric constant and losses.

Figure 7:
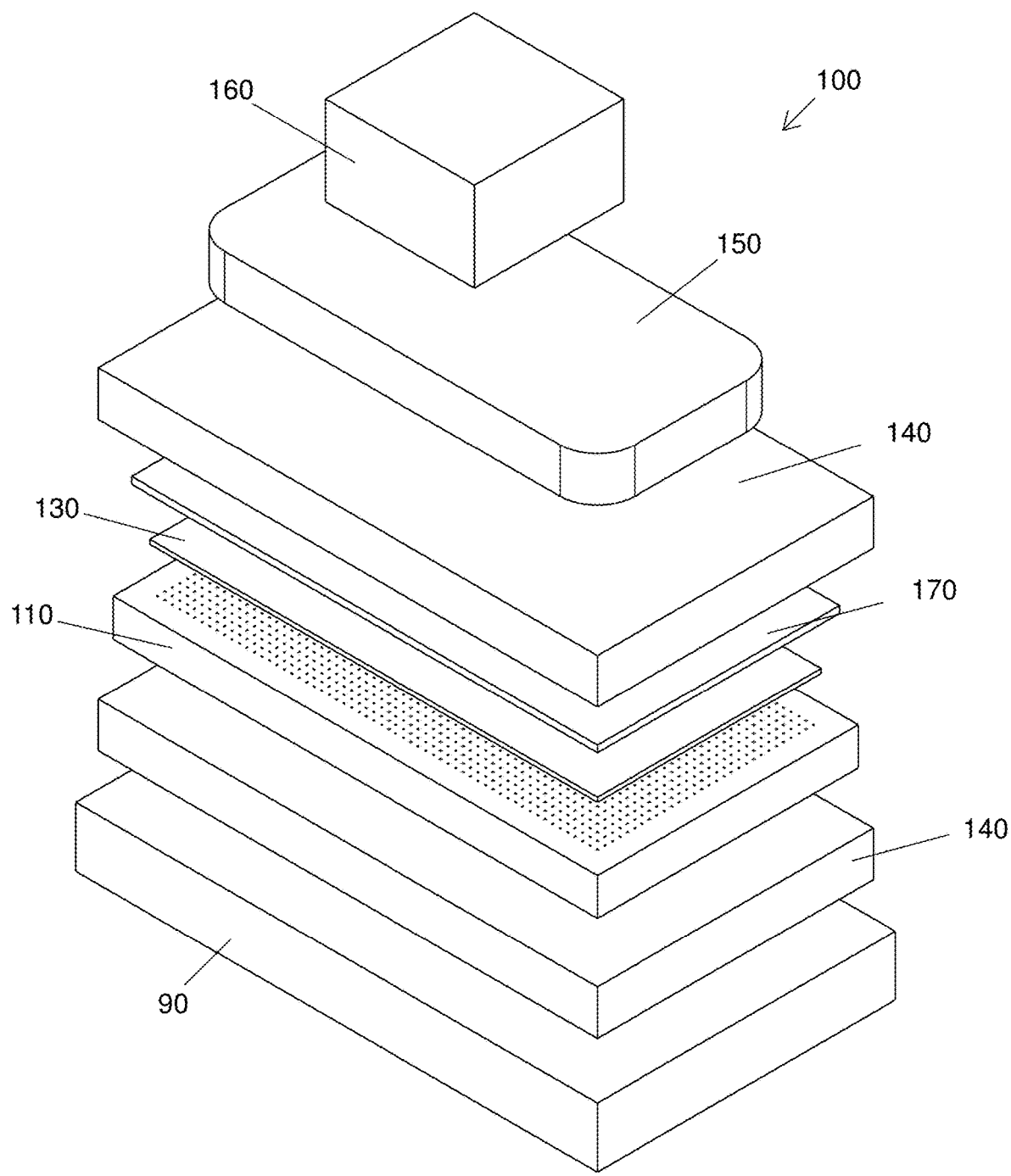
FIG. 7 is a perspective exploded depiction of elements of an embodiment of a system for molding embodiments of biomimetic scaffold materials of the present invention.
Figure 8:
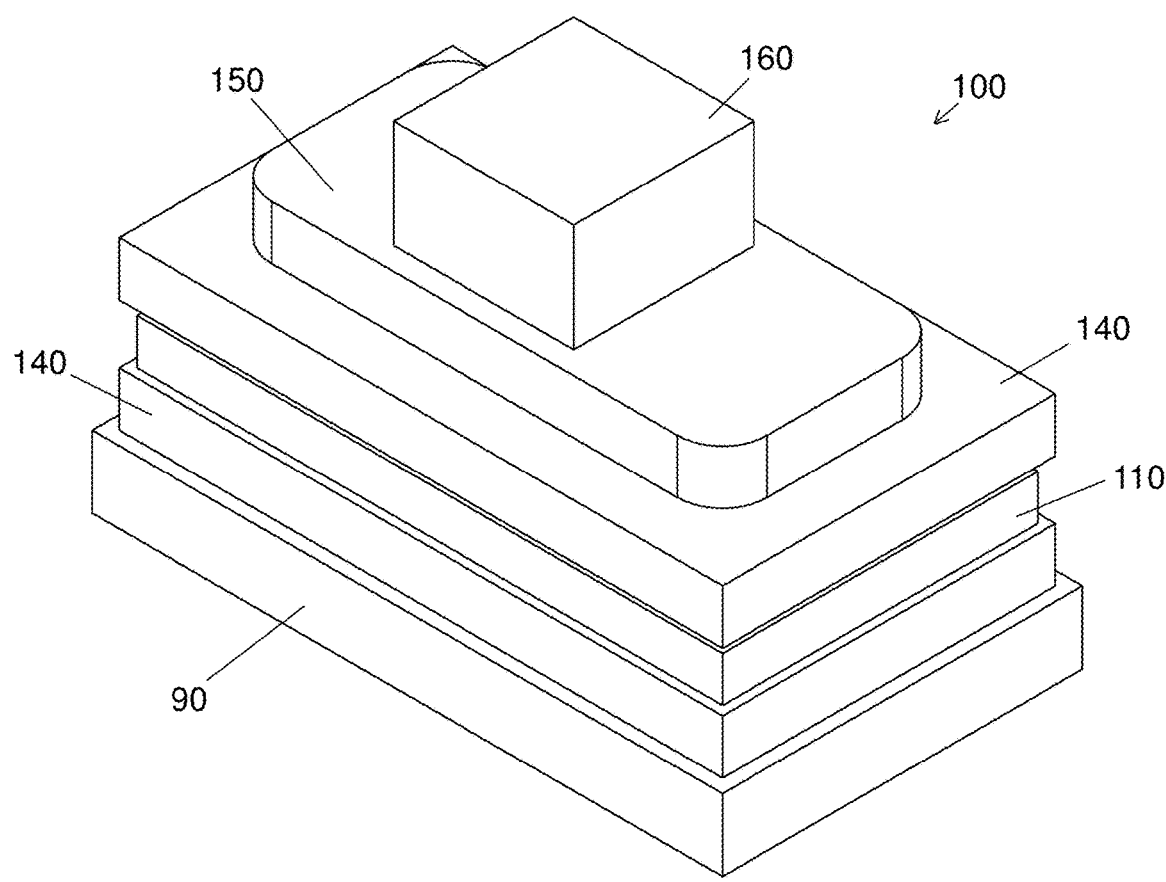
FIG. 8 is a perspective depiction of the objects of FIG. 7 assembled into an embodiment of a system for molding embodiments of biomimetic scaffold materials of the present invention.
Figure 9:
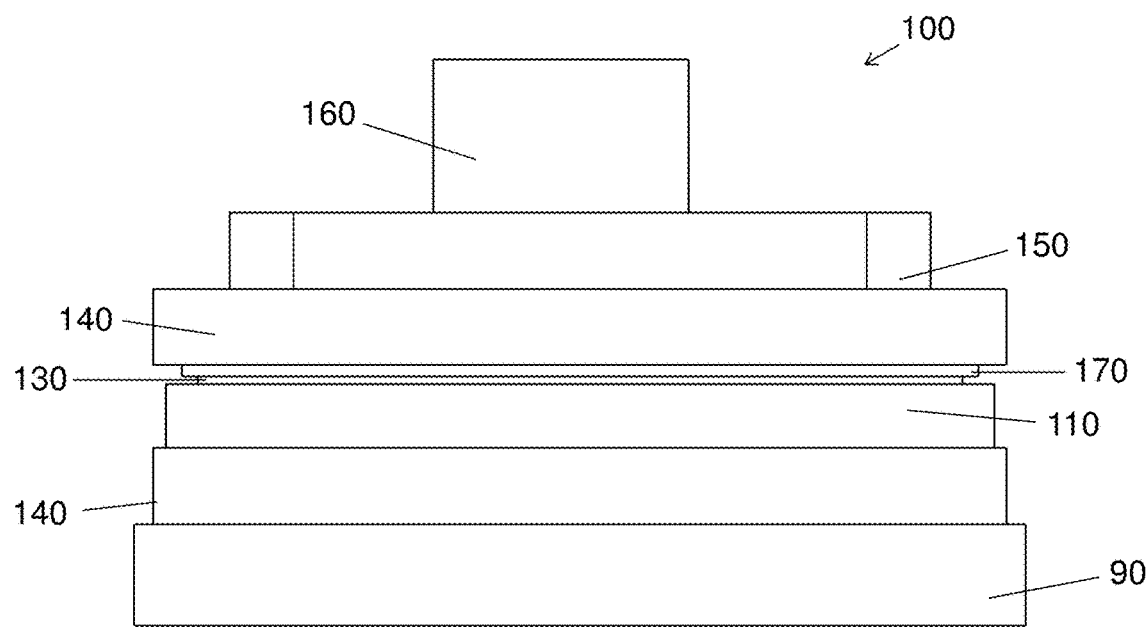
FIG. 9 is a side elevational view of the molding system of FIG. 8.
Figure 10:
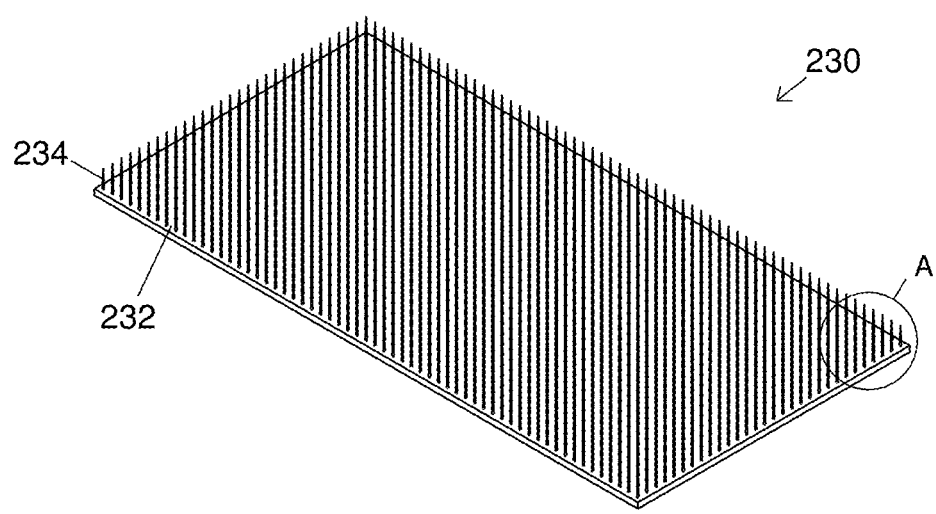
FIG. 10 is a perspective view of an embodiment of a film sheet with nanofibers formed on a surface thereof using the molding system of FIG. 9.
Figure 11:
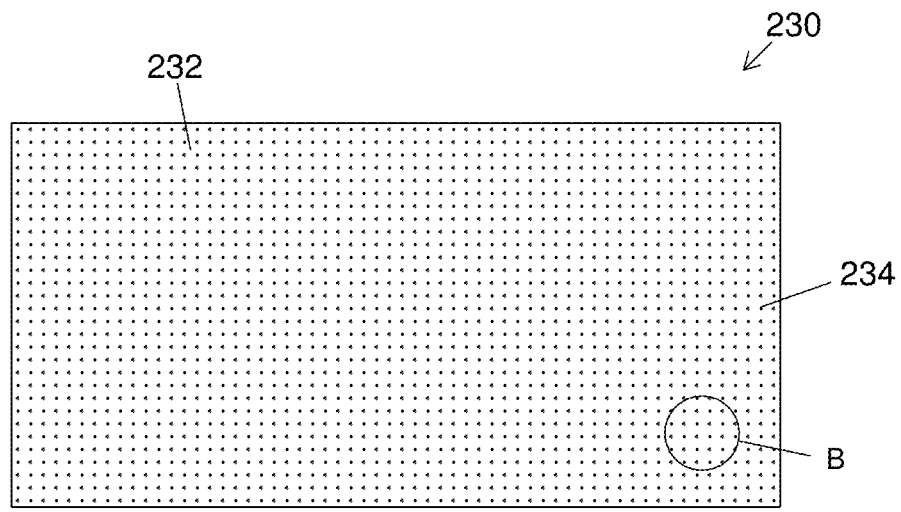
FIG. 11 is a plan view of the objects of FIG. 10.
Figure 12:
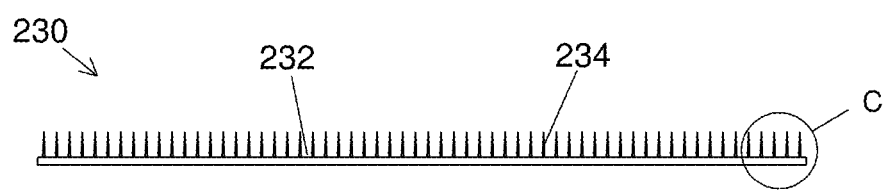
FIG. 12 is a side elevational view of the objects of FIG. 10.
Figure 13:
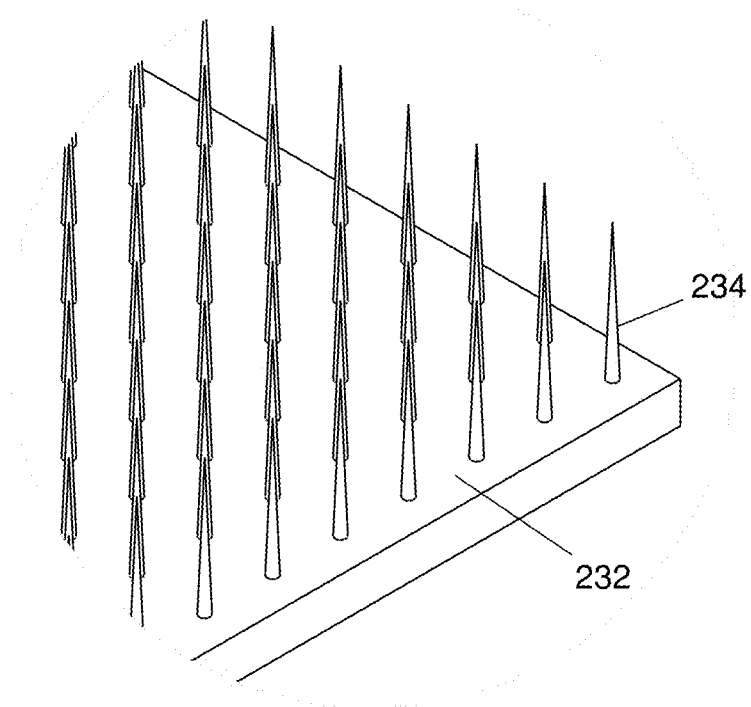
FIG. 13 is an expanded view of the objects of FIG. 10 at location A.

FIGS. 7 through 9 depict a system 100 for casting nanofiber bearing polymer films for making bioribbons of the present invention. A first temperature controlled plate 140 is positioned between base plate 90 and mold 110. Film 130 is positioned between first surface 112 of mold 110 and polymeric sheet 170, which in turn is adjacent to second temperature controlled plate 140. Compressing plate 150 is positioned between force supplying element 160 and a second temperature controlled plate 140. In use, compressing plate 150, mold 110, polymeric sheet 170 and film 130 are heated to a predetermined temperature by temperature controlled plates 140 and a force is applied to the compressing plate by force supplying element 160 so as to press film 130 against first surface 112 of silica mold 110. Heating of film 130 causes softening of the film material, and when film 130 reaches a temperature sufficient to melt the film material, the softened material of film 130 flows into nanoholes 114 in mold 110. In some embodiments wherein film 130 is formed of certain materials, the softened polymer forming film 130 infiltrates the nanoholes due to surface tension effects only. In other embodiments with films formed of the same or different materials, infiltration of the nanoholes is accomplished by a combination of hydrostatic pressure and surface tension. When the flow of film material into nanoholes 114 is maximal, system 100 is cooled sufficiently to allow film 130 to be peeled off of mold 110 with molded nanofibers attached to its surface.

The hot-pressing method for molding films with nanofiber arrays is described in detail by Hofmeister, et al. in US 2016/0222345, herein incorporated by reference. While hot pressing is a preferred method for casting film with nanofiber arrays for bioribbons of the present invention, solution casting may also be used. The solution casting method for producing film with nanofiber arrays is described in detail by Hofmeister, et al. in US 2015/0093550.

Figure 16:
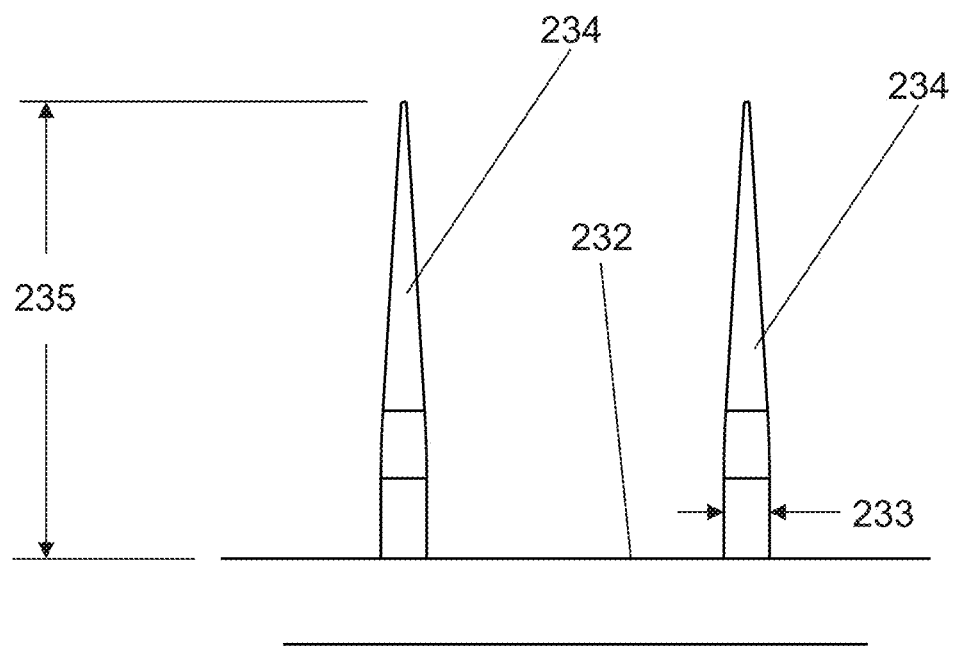
FIG. 16 is a side elevational depiction of a first nanofiber configuration that may be formed on a film for making embodiments of biomimetic scaffold materials of the present invention.
Figure 17:
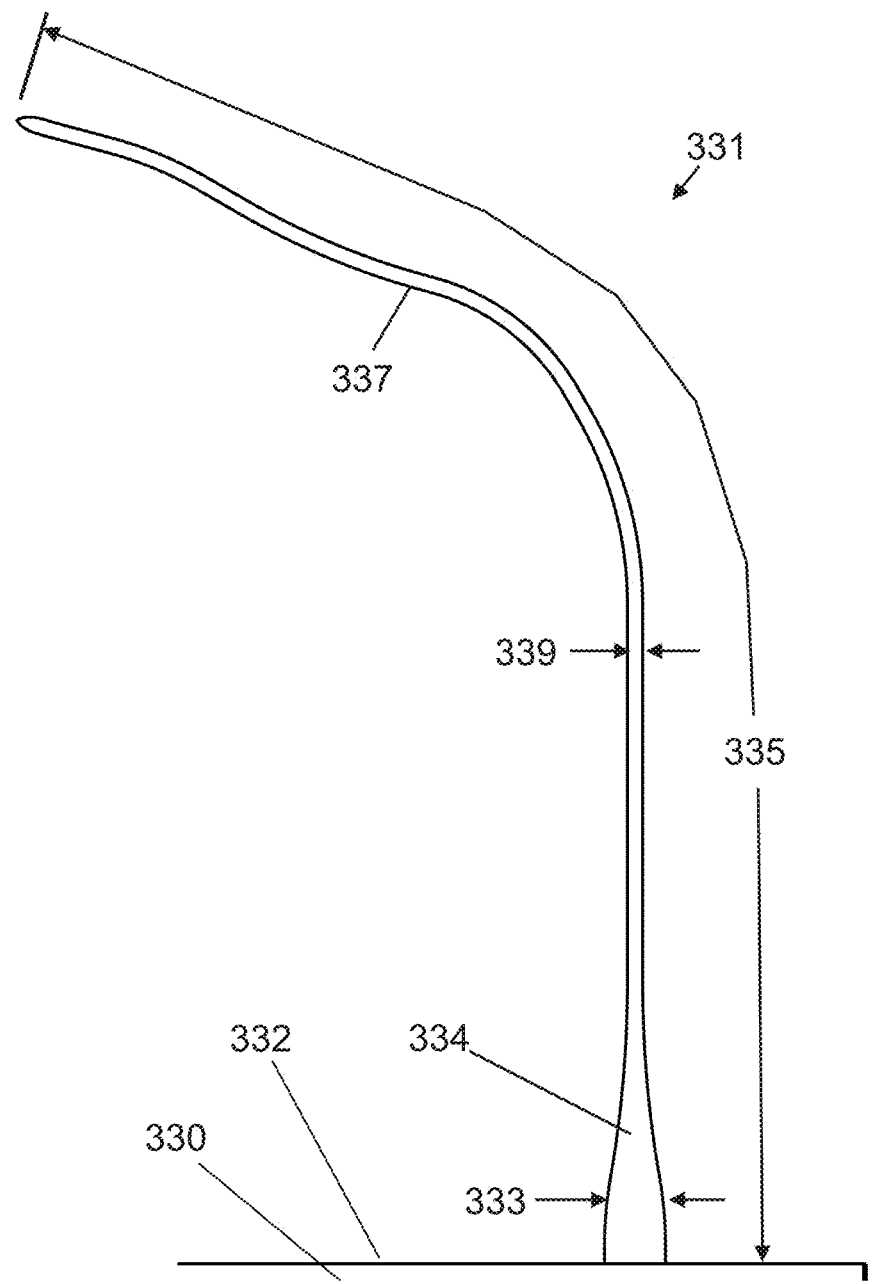
FIG. 17 is a side elevational depiction of a second nanofiber configuration that may be formed on a film for making embodiments of biomimetic scaffold materials of the present invention.

Referring now to FIGS. 10 through 15, film 230 has a first surface 232 on which are formed arrays of nanofibers 234, nanofibers 234 being form by the hot press molding process previously herein described. Nanofibers 234 are spaced distance 238 in a first direction and distance 240 in a second direction perpendicular to the first direction. Distance 238 is equal to distance 116 between nanoholes 114 in mold 110 (see FIG. 5). Distance 240 is equal to distance 118 between nanoholes 114 in mold 110, the geometry of the array of nanofibers 234 of film 230 being complementary to the geometry of the array of nanoholes in mold 110. Nanofibers formed in methods of the present invention have a generally tapered shape, the length, base diameter and length together determining the rigidity of the nanofiber. Nanofiber 234, depicted in FIG. 16, has a degree of rigidity imparted by the ratio of length 235 to first (base) diameter 233, length 235 being a low multiple of diameter 233. FIG. 17 depicts a nanofiber 331 of length 335 with low rigidity. Nanofiber 331, formed on surface 332 of film 330 has a first diameter 333 adjacent to surface 332, and a tapered portion 334 adjacent thereto from which extends elongate distal portion 337 of diameter 339.

Characteristics of an array of nanofibers may be optimized to provide signaling to cells that affects the cell differentiation and fate. Distances 238 and 240 between nanofibers 234 (see FIG. 14) may be selected to approximate the spacing of the collagen tendrils on the basement membrane of the ECM of a desired tissue type. Like the ECM tendrils, nanofibers 234 and 334 have a proximal portion that is rigidly normal to film portions 230 and 330. The proximal portions of nanofibers 234 and 334 act as a cantilever beam with a degree of rigidity determined by their shape and length. Accordingly, the rigidity of nanofibers forming an array and the length of those nanofibers together affect shear forces at the focal connections between cells populating the scaffold and the nanofibers of arrays on bioribbons forming the scaffold. As with the spacing between nanofibers of an array, the configuration of the nanofibers of an array may be optimized to mimic the tendrils of an ECM for a desired cell type and behavior. The controlled spacing, rigidity and length of nanofibers forming arrays allow the creation of a "tuned topography" that allows the control of cell behavior not possible in prior art scaffolds. Scaffolds of the present invention with nanofiber arrays that approximate the fibrils on the basement membrane of an ECM are biomimetic to a degree far surpassing that of prior art scaffolds.

Figure 18:
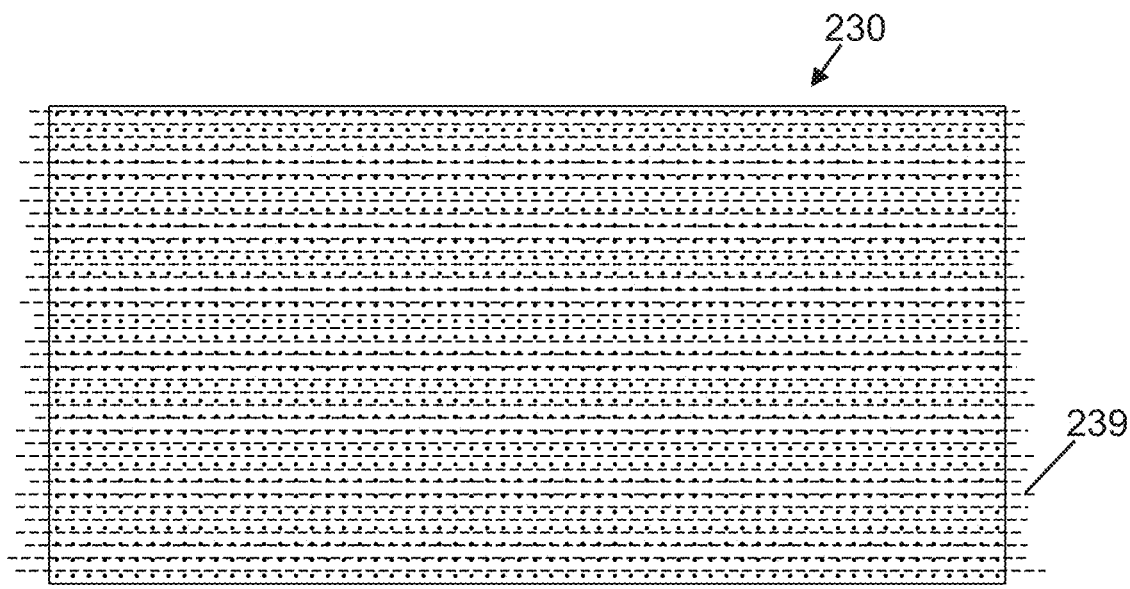
FIG. 18 is a plan view depicting the film sheet of FIG. 10 with linear parallel cuts to create nanofiber-bearing bioribbons for forming embodiments of biomimetic tissue scaffolds of the present invention.
Figure 19:
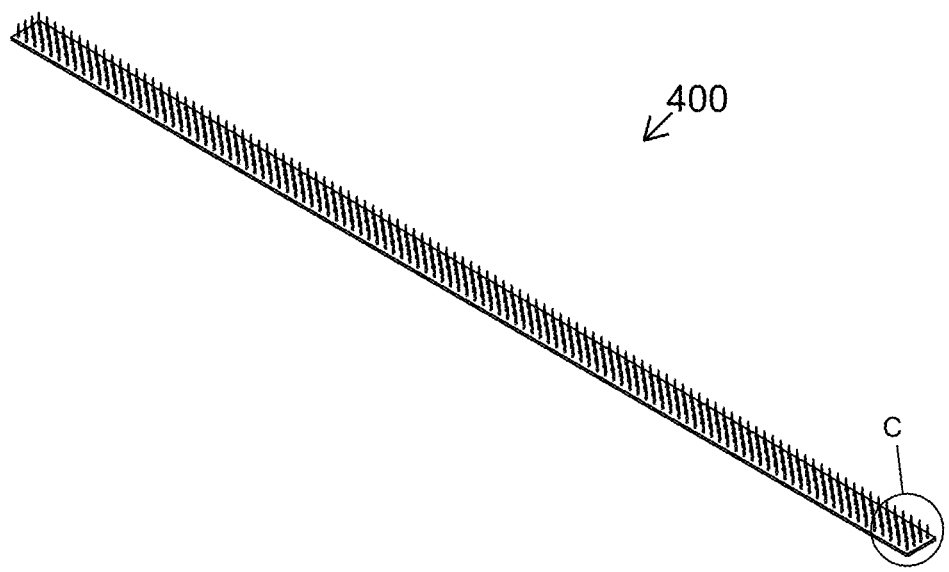
FIG. 19 is a perspective view of a portion of an embodiment of a nanofiber-bearing bioribbon of the present invention used to create embodiments of biomimetic scaffolds of the present invention.
Figure 20:
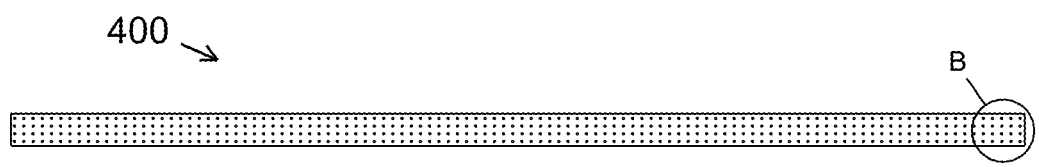
FIG. 20 is a plan view of the objects of FIG. 19.
Figure 21:
FIG. 21 is a side elevational view of the objects of FIG. 19.
Figure 22:
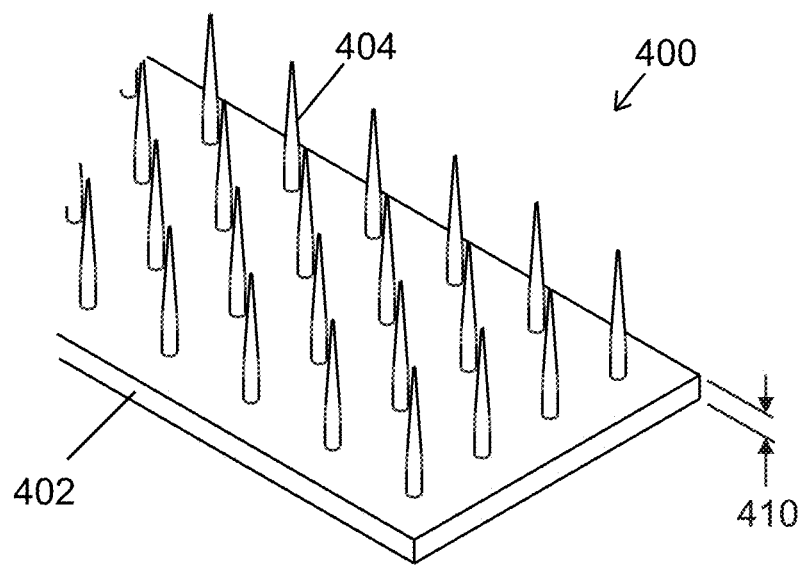
FIG. 22 is an expanded view of the objects of FIG. 19 at location C.
Figure 23:
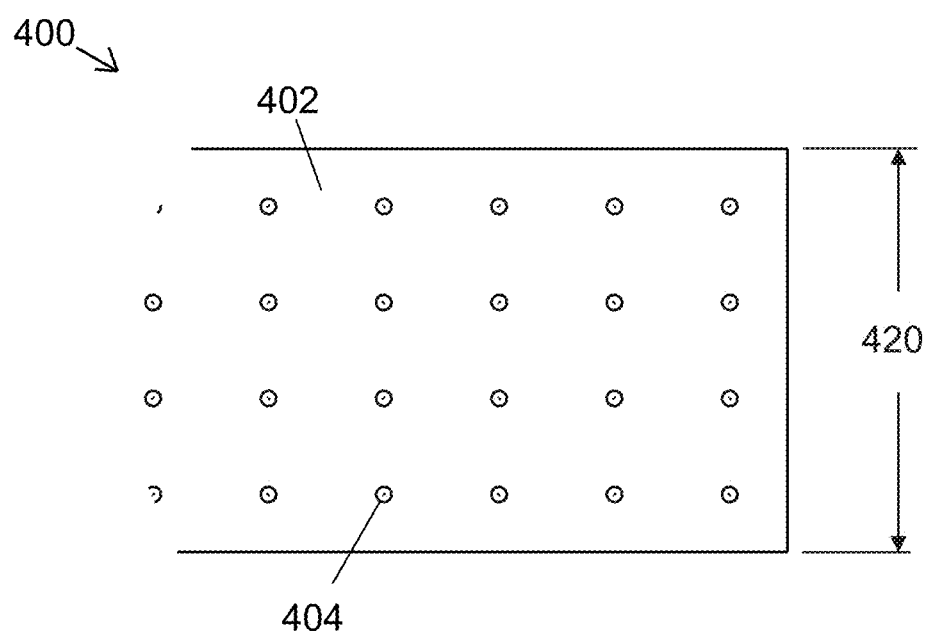
FIG. 23 is an expanded view of the objects of FIG. 20 at location B.

Film 230 may be cut into narrow strips as depicted in FIG. 18 to create bioribbons of the present invention. FIGS. 19 through 23 depict a portion of a bioribbon 400 of the present invention. Ribbon 400 of thickness 410 and width 420 has a film portion 402 from which protrudes an array of nanofibers 404. Width 420 is preferably less than 100× thickness 410, more preferably less than 50×, and still more preferably less than 10×, the particular ratio being optimized for the particular application of the biomimetic scaffold and for ease of manufacture.

Figure 24:
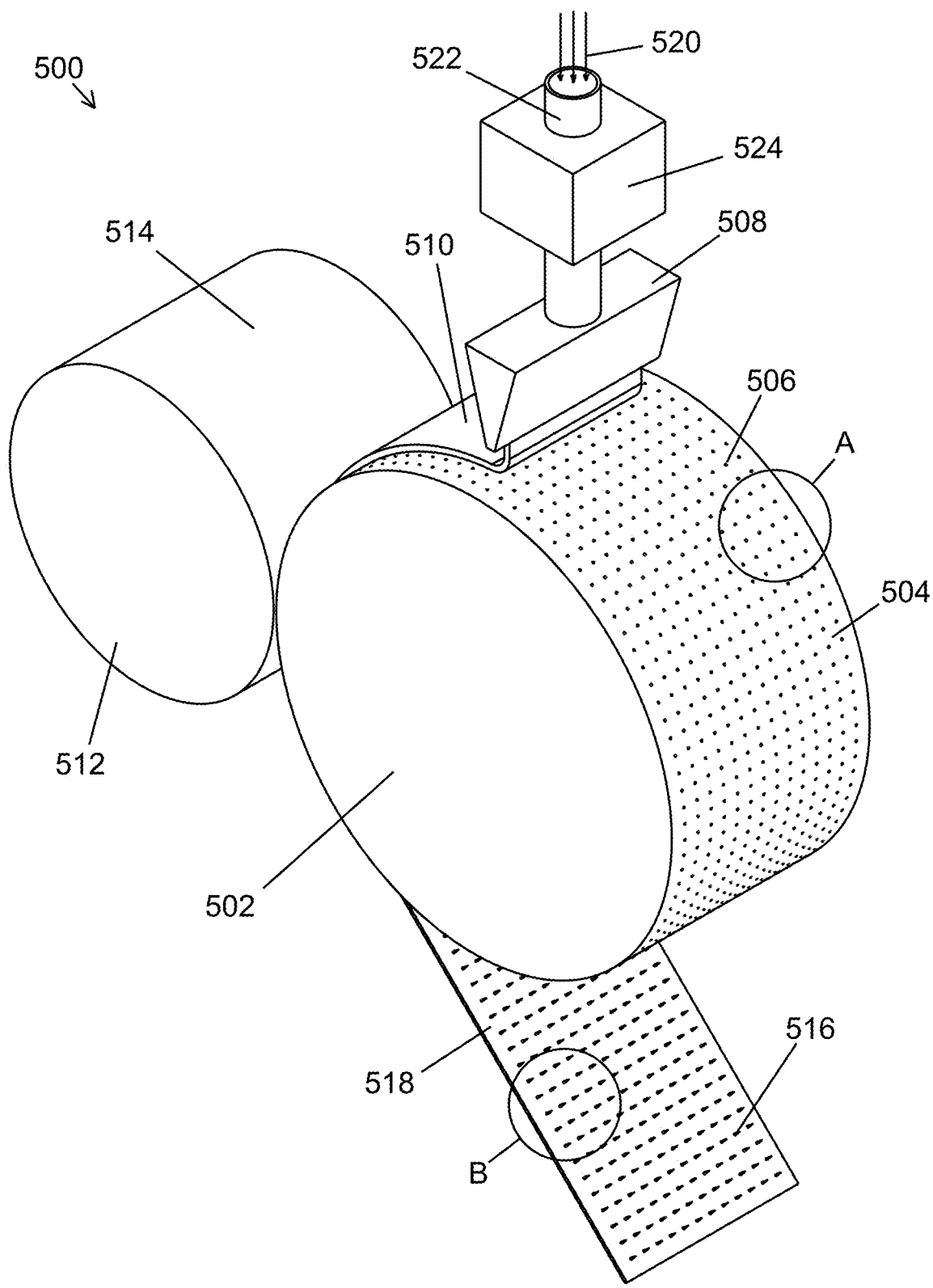
FIG. 24 is a perspective view of an alternate embodiment of a molding system for forming elongate film elements with nanofibers formed on a surface thereof for making embodiments of biomimetic tissue scaffolds of the present invention therefrom.

Another preferred method for manufacturing bioribbons of the present invention has the ability to produce continuous elongate strips of film with arrays of nanofibers formed on at least one surface thereof. In method 500, a variation of a film producing technique referred to as "chill roll casting" and depicted in FIG. 24, polymer 520 is supplied via tubular member 522 to extrusion head 508. Polymer 520 is heated above its melt point by heater 524 and the melted polymer 510 is then applied to rotating cylindrical roll 502 (referred to as a "chill roll") formed of silica or another suitable material. An array of nanoholes 506 is formed in the circumferential surface 504 of roll 502 so as to form a mold, the nanohole array being complementary to the array of nanofibers to be formed. The nanoholes are formed using methods previously described herein. Molten polymer 510 flows into nanoholes 506 as it is applied to circumferential surface 504 of rotating chill roll 502. Chill roll 502 is maintained at a temperature such that during a predetermined portion of the roll rotation of chill roll 502, polymer 510 in nanoholes 506 is cooled along with the portion of polymeric material 510 coating circumferential surface 504 of roll 502. A cylindrical metallic roll 512, commonly referred to as a "anvil roll" or "quench roll" functions as the compressing element and is positioned adjacent to chill roll 502 such that after a predetermined angular rotation of chill roll 502 polymeric material 510 coating the surface of chill roll 502 is compressed between surface 504 of chill roll 502 and surface 514 of the quench roll 512. As implied by the name "quench roll" polymeric material 510 undergoes rapid cooling during contact with quench/anvil roll 512 so that it may be subsequently stripped from the surface of chill roll 502 as a continuous elongate strip of film 518. When the polymer strip 518 is removed from chill roll 502, material 510 that had previously flowed into nanoholes 506 forms molded nanofibers 516 on the surface of film strip 518. In subsequent processing elongate strips 518 may be slit, cut, chopped or otherwise formed into bioribbons of the present invention. As with the previously described hot pressing method, polymer 520 is not contained in a solution so the use of environmentally undesirable solvents is not required.

Under certain conditions, with suitable polymers, quench roll 512 is eliminated. The thickness of film strip 518 is determined by process parameters. These may include properties of polymer 520, the temperature of polymer 510 as it is deposited on surface 504 of chill roll 502, the temperature and rotational speed of chill roll 502, and other factors that affect the cooling of film strip 518. Under these conditions, material is drawn into nanoholes 506 of surface 504 of chill roll 502 by surface tension as a compressing element is not used.

Figure 25:
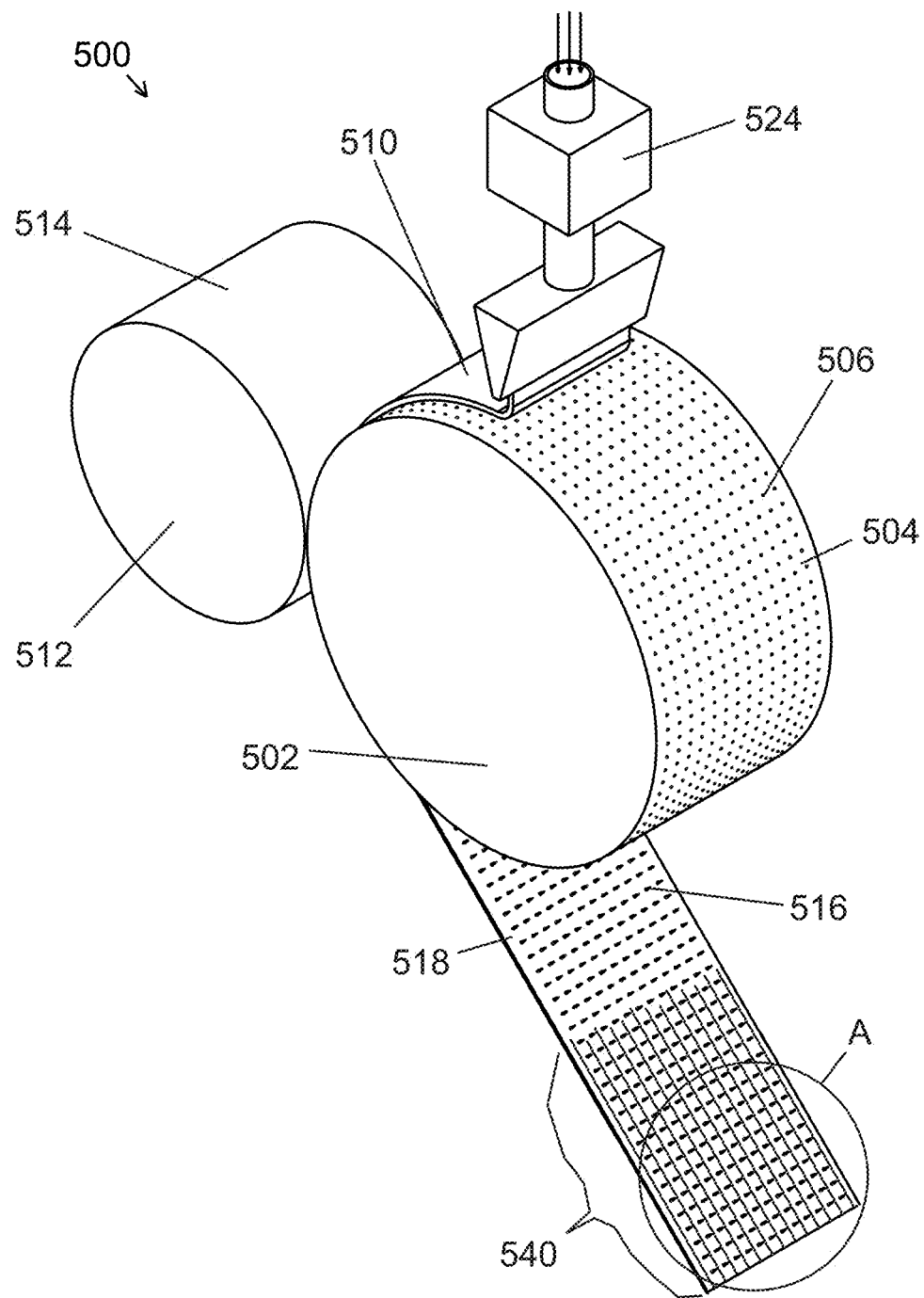
FIG. 25 is a perspective view of the molding system of FIG. 24 including means for automatically forming elongate slits in the elongate film element as it is molded.
Figure 26:
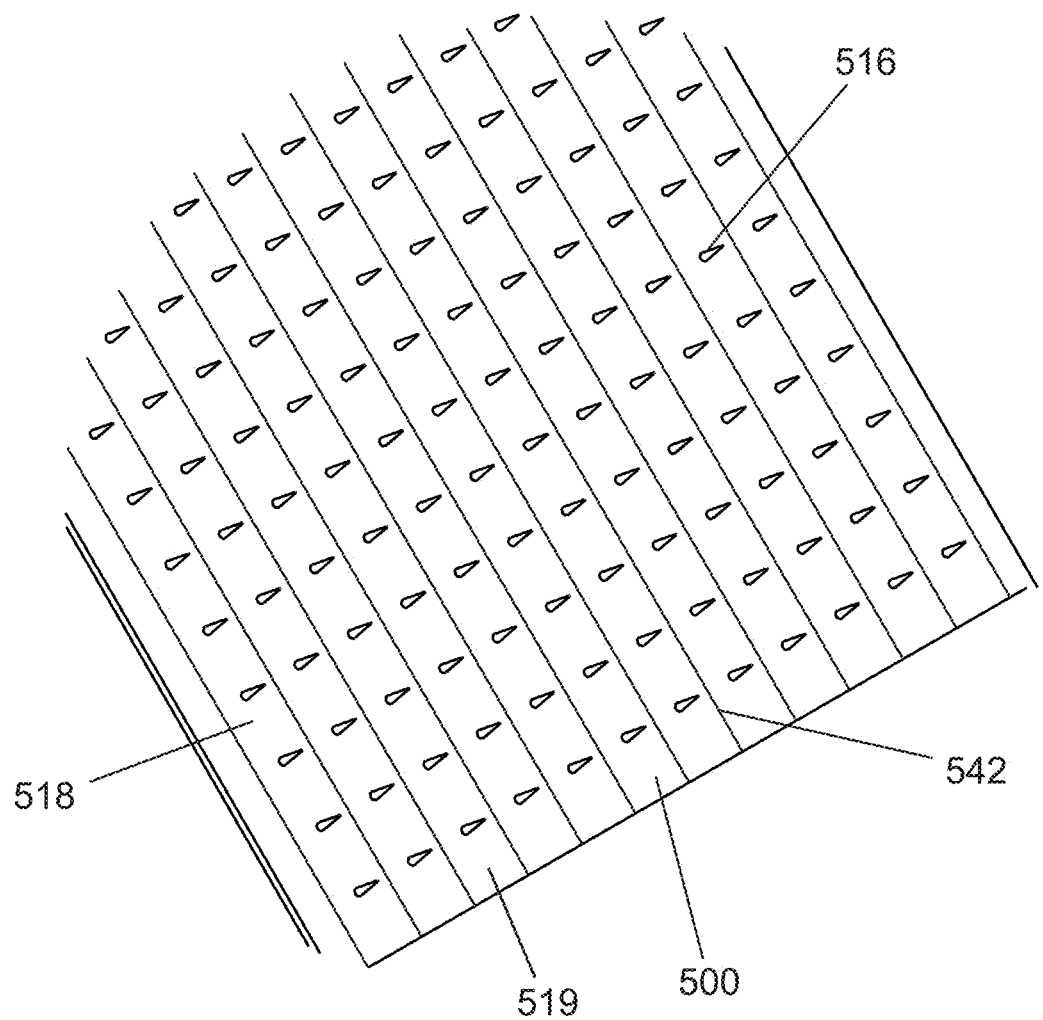
FIG. 26 is an expanded view of the film element of FIG. 25 at location A.
Figure 27:
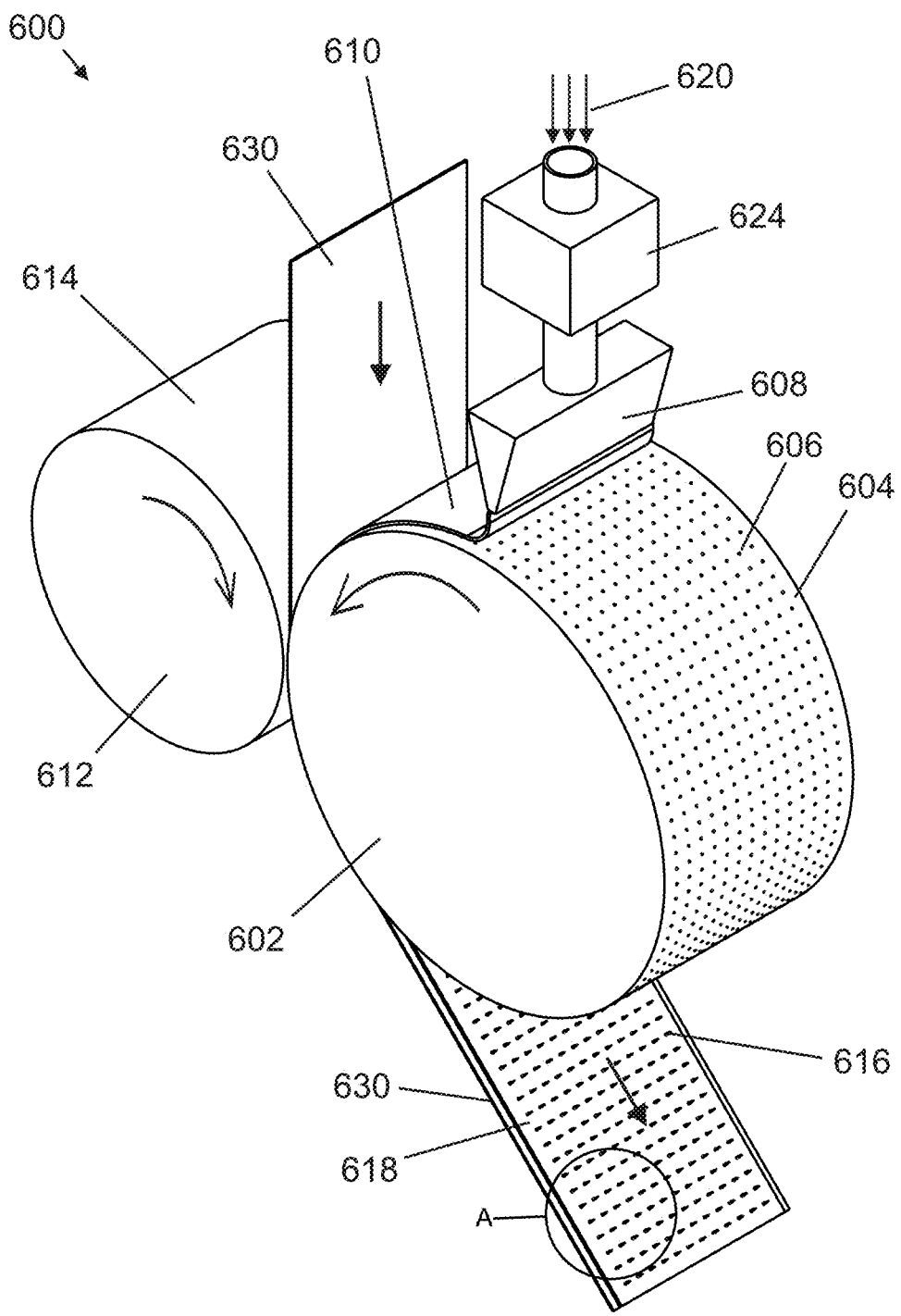
FIG. 27 is a perspective view of another alternate embodiment molding system for forming laminar elongate film elements with nanofibers formed on a surface thereof for making embodiments of biomimetic tissue scaffolds of the present invention therefrom.
Figure 28:
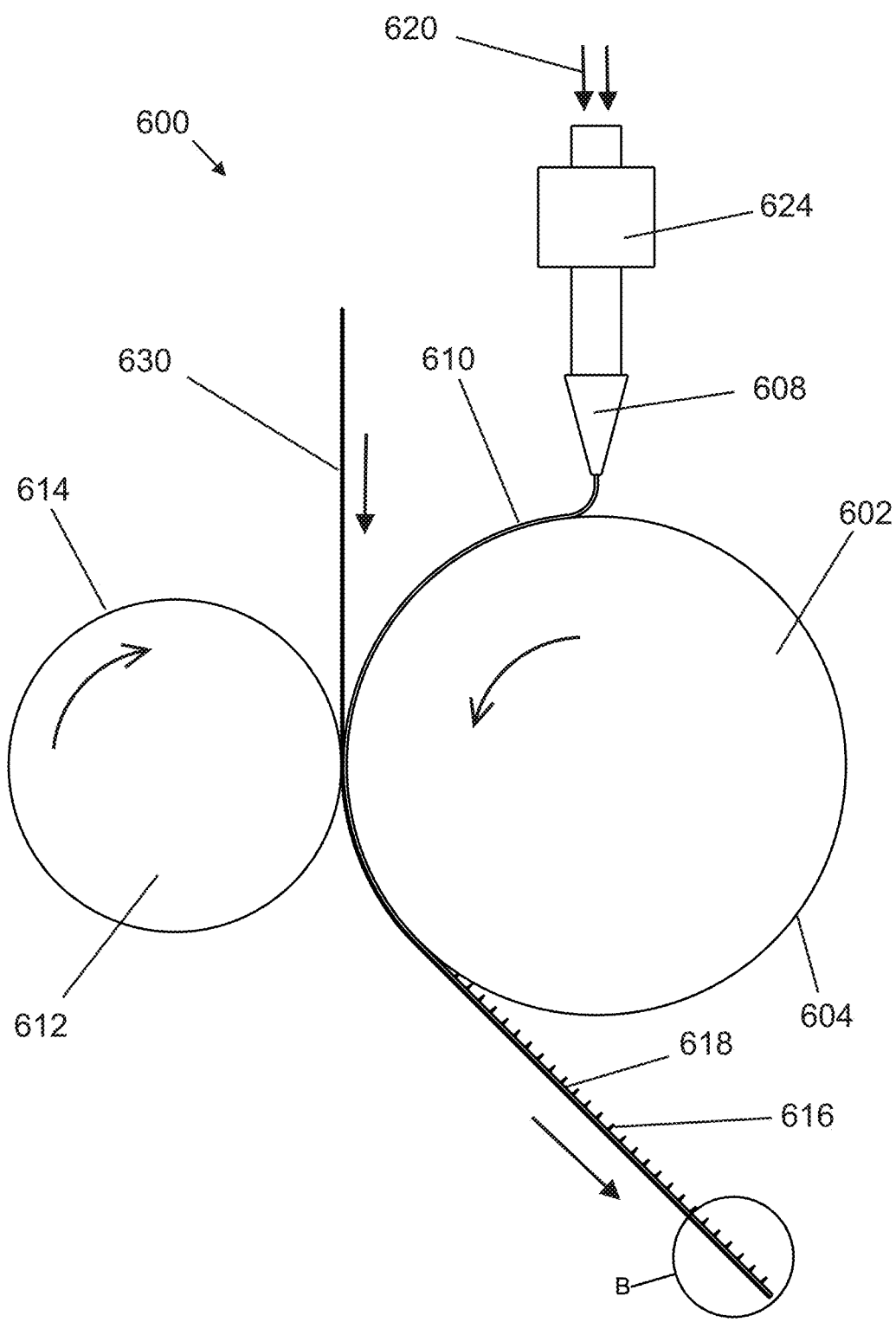
FIG. 28 is a side elevational view of the objects of FIG. 27.
Figure 29:
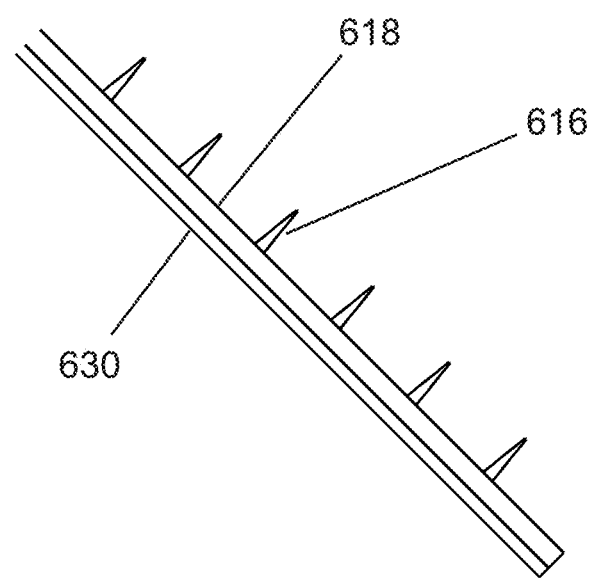
FIG. 29 is an expanded view of the film of objects of FIG. 28 at location B.
Figure 30:
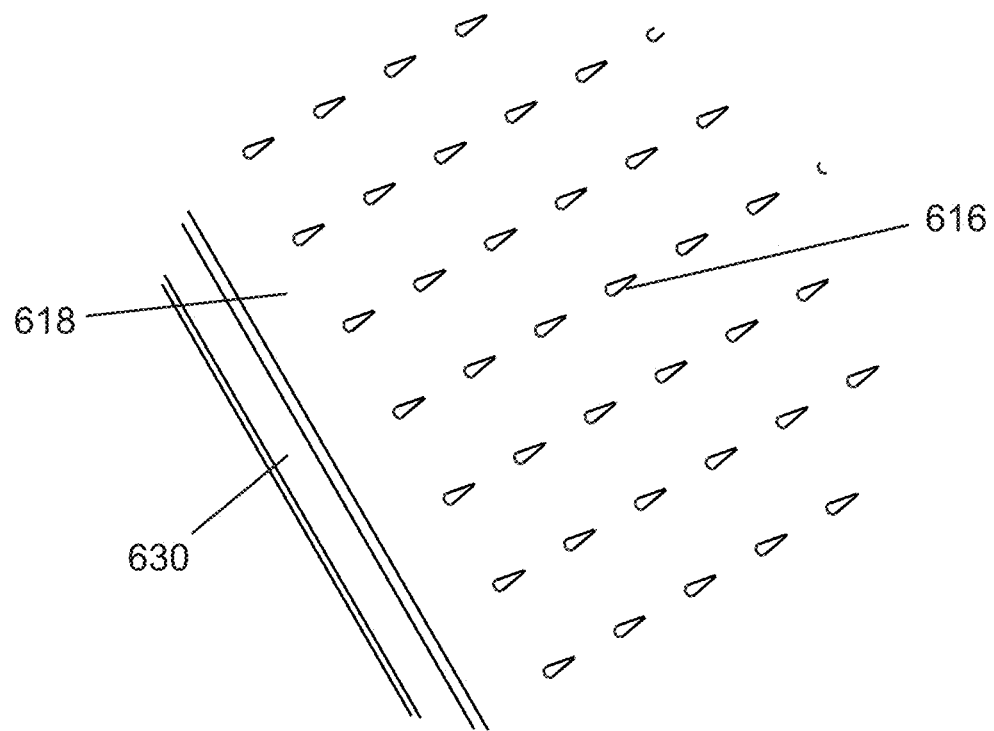
FIG. 30 is an expanded view of the objects of FIG. 27 at location A.

Unlike prior art processes for producing nanofibers for tissue scaffolds, the chill roll casting process previously herein described is scalable and may be automated to enable production of quantities of nanofiber-bearing bioribbons rapidly and at low cost. For instance, referring now to FIGS. 25 and 26 depicting chill roll casting system 500 (FIG. 24), slitting of film strip 518 may accomplished automatically by adding a slitting means as depicted in FIG. 18. Subsequent to the removal of film strip 518 from chill roll 520, a plurality of slits 542 are formed in strip 518 so as to form a plurality of bioribbons 519 of the present invention as depicted in region 540 of FIG. 25. Ribbons 518 are analogous in form and function to elongate ribbons 400 depicted in FIGS. 19 through 23. The slitting may be accomplished by mechanical means using a rotating cylindrical cutting element with a plurality of sharpened circumferential cutting edges formed on its cylindrical surface, and a second rotating cylinder. The axes of both cylinders are parallel to the axis of chill roll 504, and are positioned such that the cutting edges of the cutting element contact or are in very close proximity to the surface of the second rotating cylinder. Strip 518 passes between this rotating cutting element and the second cylinder so that each cutting edge forms a continuous longitudinal slit 542 in strip 518. Slitting of film material in this manner is well known in the art.

In the casting system 500 of FIGS. 25 and 26 longitudinal slits 542 are formed in strip 518 automatically as strip 518 is produced. In other methods of the present invention, slitting of strip 518 is done as a secondary process remote from the system 500. Strip 518 may be wound onto a spool for storage and subsequent slitting. In the previous example, longitudinal slits 542 were formed in strip 518. In other methods for making bioribbons of the present invention, lateral slits are made to form ribbons. Indeed, any method of cutting, slitting or chopping a film strip on which nanofiber arrays are formed may be used to form bioribbons of the present invention. All fall within the scope of this invention.

FIGS. 27 through 30 depict a chill casting system 600 of the present invention for making a layered film for forming bioribbons of the present invention. Polymer 620 is supplied via tubular member 622 to extrusion head 608. Polymer 620 is heated above its melt point by heater 624 and the melted polymer 810 is then applied to rotating chill roll 602. Molten polymer 610 flows into nanoholes 606 as it is applied to circumferential surface 604 of rotating chill roll 602. Polymer film 630 is drawn into the juncture between quench roll 612 and cylindrical surface 608 of chill roll 604 upon which melted polymer 610 has been deposited. Quench roll 612 cools molten polymer 610 in the manner previously described, but also forms a bond between film 630 and polymer 610 so that when film strip 618 is removed from chill roll 604 as a layered construct with a first layer on which are formed nanofiber arrays of the present invention, and a second layer formed of film 630. In this manner film and the bioribbons formed therefrom may have nanofiber arrays formed of a first polymeric material 610 with optimal properties for forming nanofiber arrays with desirable characteristics for a given application, bonded to a second polymeric material forming film 630. Forming a construct in this manner allows polymers with optimal properties for nanofiber formation to be bonded to polymer films that have other optimal properties for tissue scaffolds formed of bioribbons.

Figure 31:
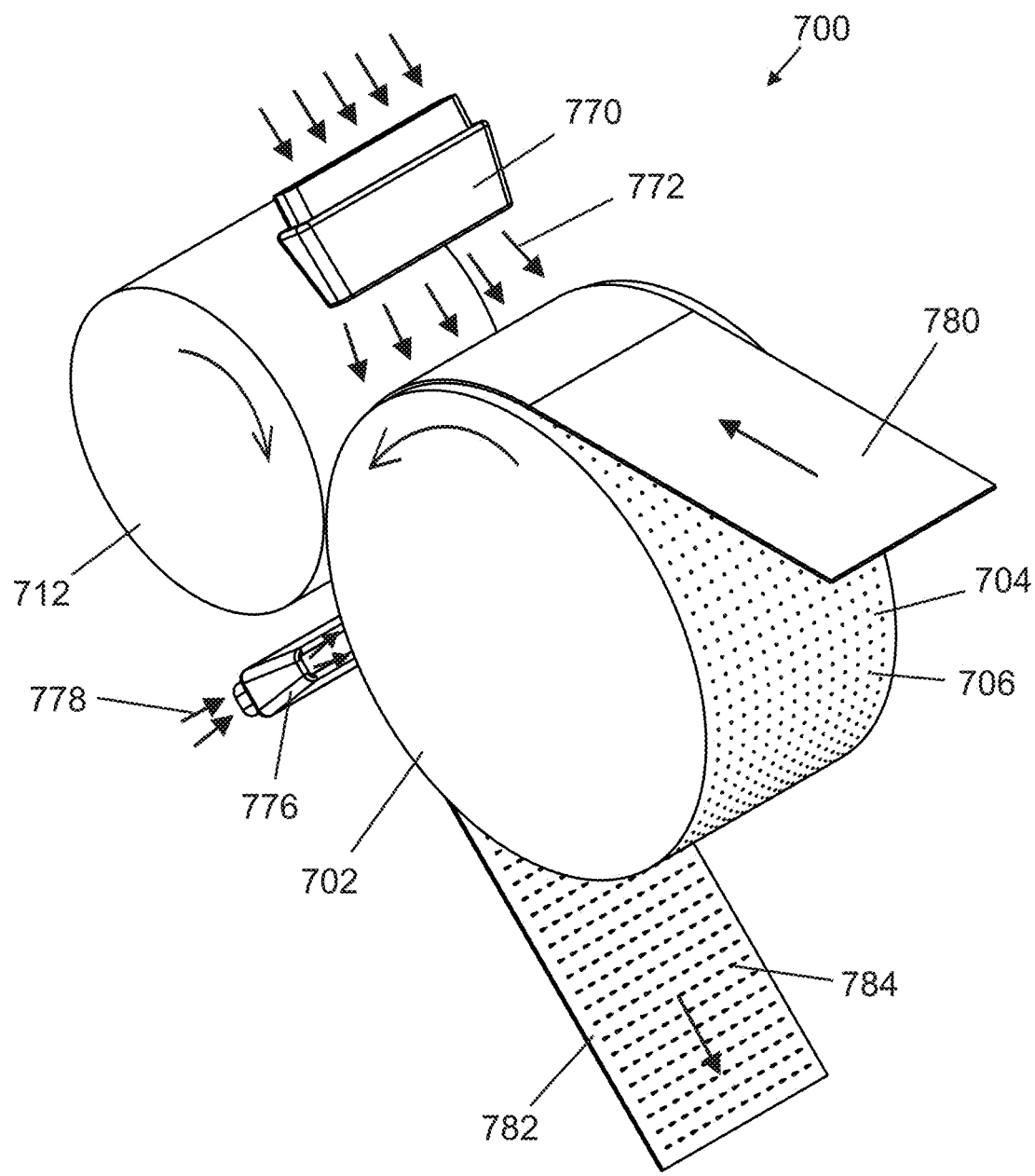
FIG. 31 is a perspective view of yet another alternate embodiment molding system for forming laminar elongate film elements with nanofibers formed on a surface thereof for making embodiments of biomimetic tissue scaffolds of the present invention therefrom.
Figure 32:
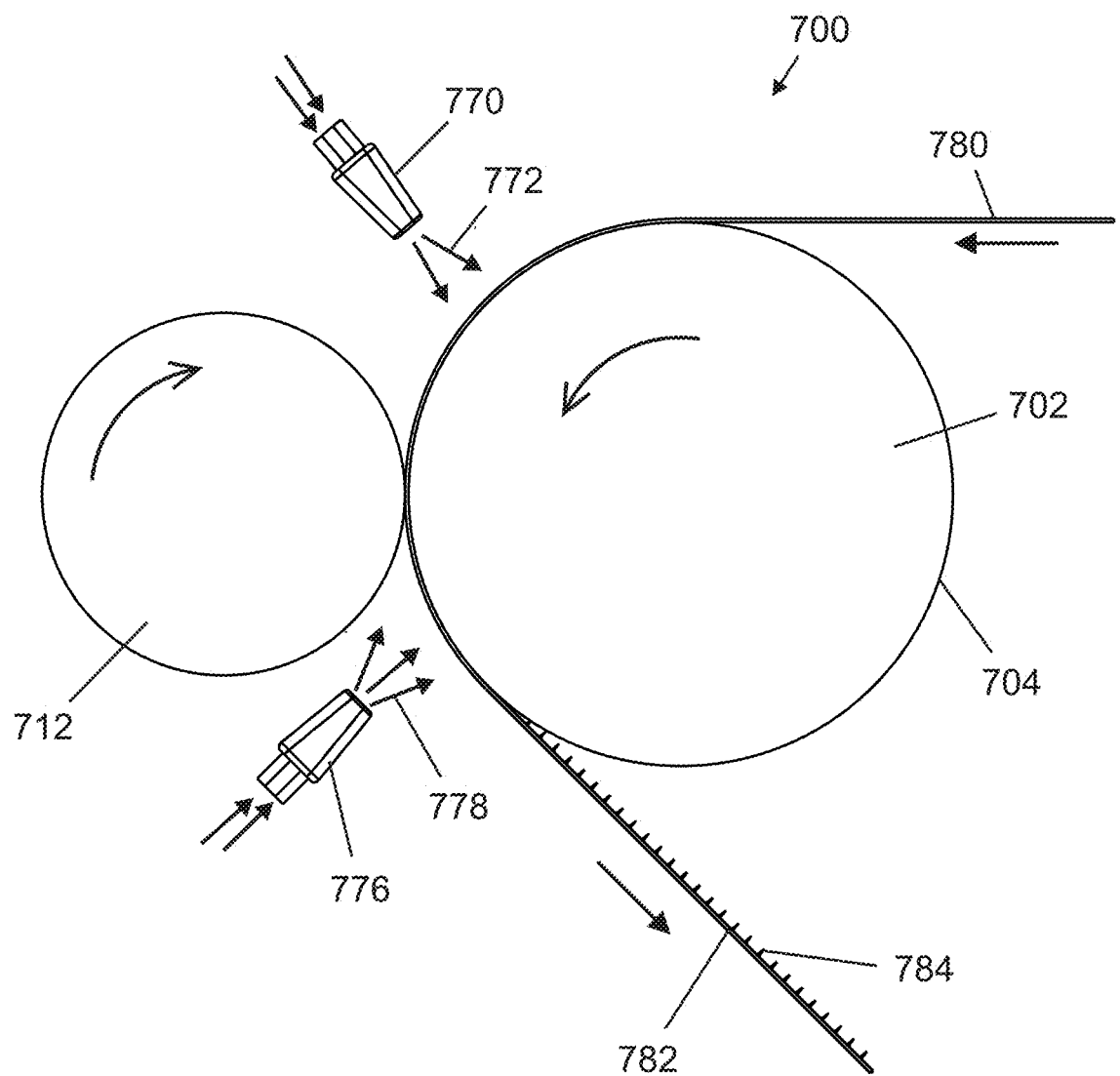
FIG. 32 is a side elevational view of the objects of FIG. 31.

In an alternate system for making films with nanofiber arrays for producing bioribbons of the present invention, nanofibers are embossed on an existing film of polymeric material, the embossing being accomplished in a process similar to the chill casting method previously herein described. In previous embodiments a molten polymer is applied to the mold. In the embossing embodiment film is applied to the mold; the film is sufficiently heated to allow the material to flow into the mold nanoholes, then cooled so that the film with its newly formed nanofibers can be peeled from the mold. Referring now to FIGS. 31 and 32 depicting an embossing system 700 of the present invention, film 780 wraps around circumferential surface 704 of mold 702 wherein are formed nanoholes 706. Film 780 is heated by airflow 772 from nozzle 770 sufficiently to melt or sufficiently softened to allow film material to flow into nanoholes 706. Quench roll 712 applies a compressive force to softened film 780 that assists with the flow of film material into nanoholes 706. Chilled air 778 cools film 780 so that chilled film 782 with nanofibers 784 to be peeled from cylindrical surface 704 of chill roll 702. Film 782 is like film 518 with nanofibers 516 formed by casting system 500 (FIG. 24) in all aspects of form and function. Layered films with embossed nanofibers may also be made by a method similar to that previously described and depicted in FIGS. 27 through 30. In the embossing method a second film is drawn into the juncture between quench roll 712 and film 780 so as to bond film 780 to the second film. System 700 uses heated airflow to increase the temperature of film so that film material can flow into nanoholes. In other embodiments film 780 is heated by a radiant heater or other suitable means.

Figure 33:
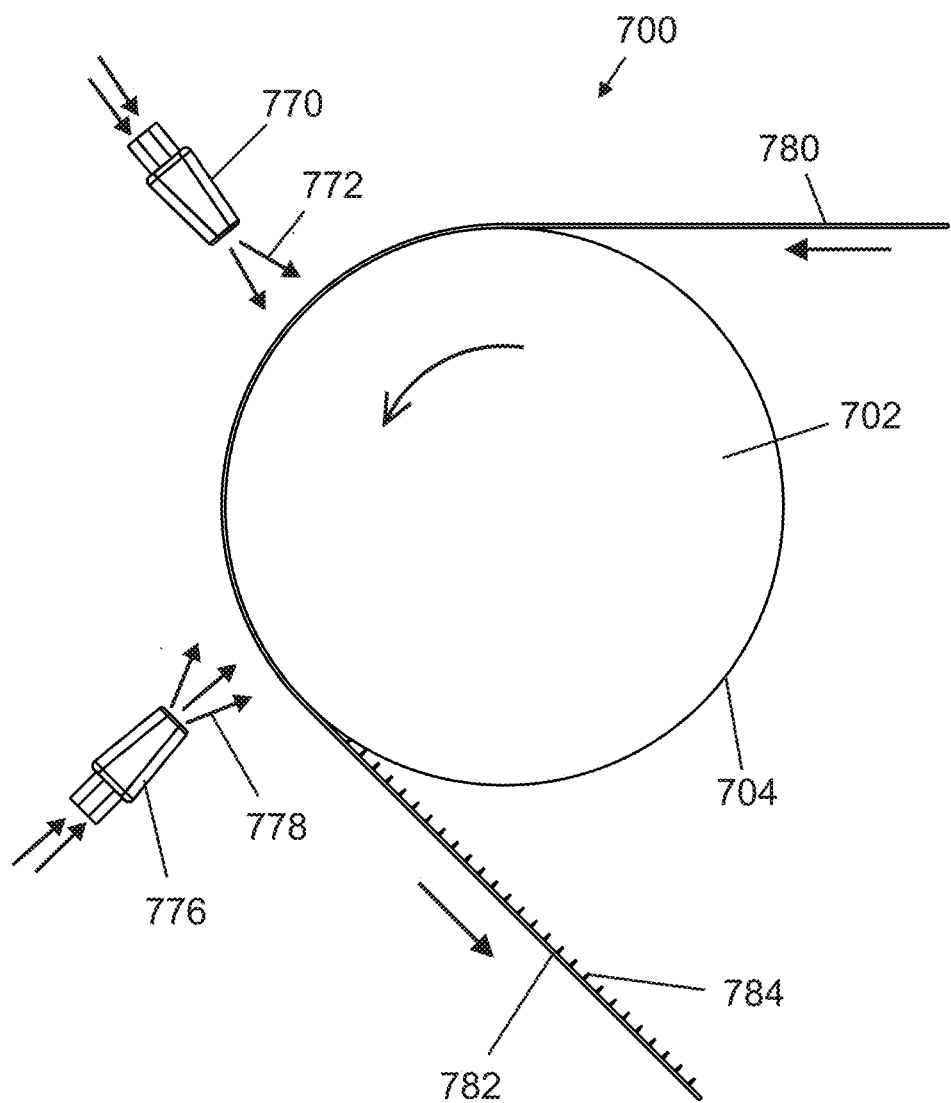
FIG. 33 is a side elevational view of a still yet another alternate embodiment molding system for forming laminar elongate film elements with nanofibers formed on a surface thereof for making embodiment of biomimetic tissue scaffolds of the present invention therefrom.
Figure 34:
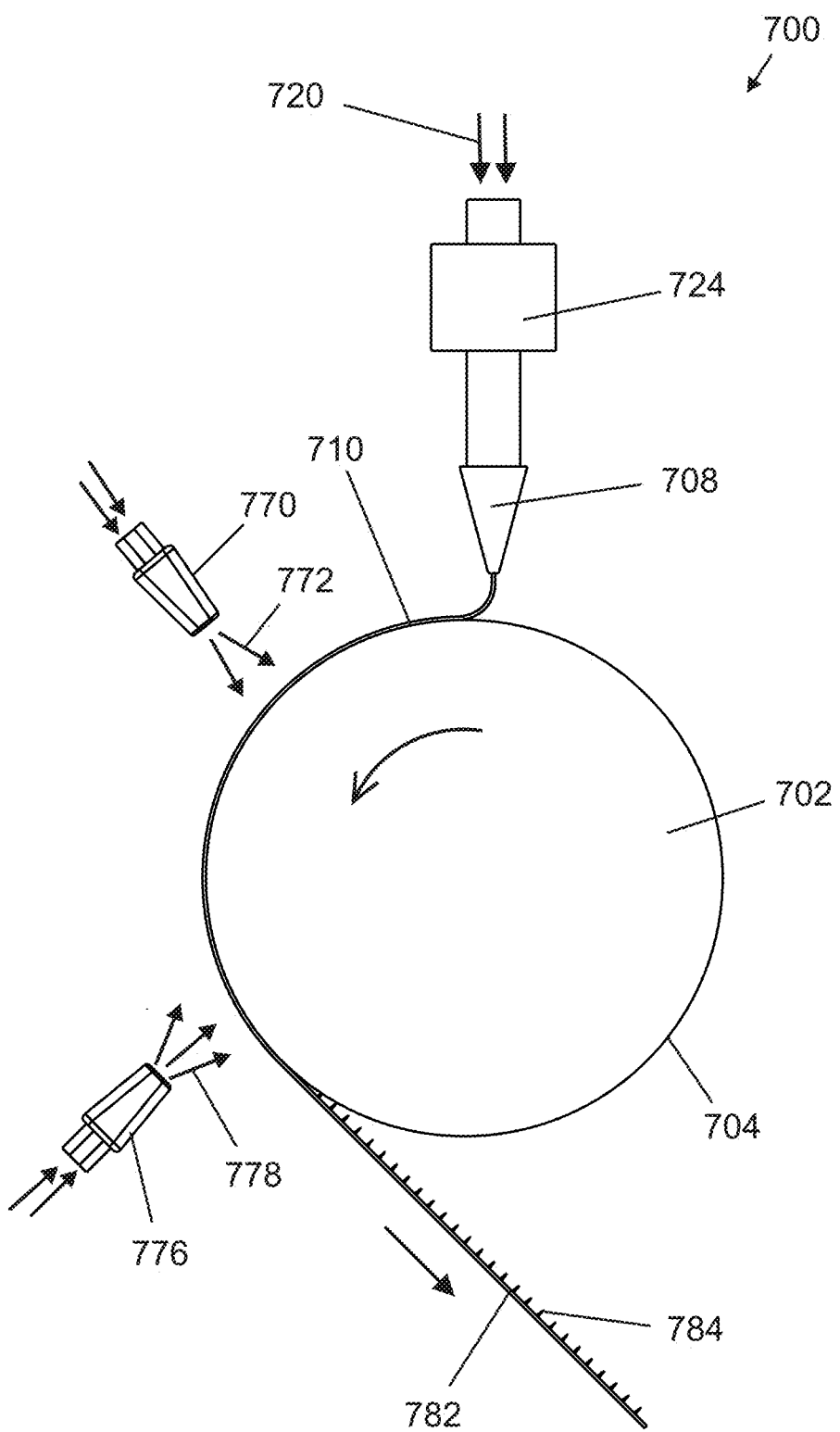
FIG. 34 is a perspective view of even yet another alternate embodiment molding system for forming laminar elongate film elements with nanofibers formed on a surface thereof for making embodiments of biomimetic tissue scaffolds of the present invention therefrom.

FIG. 33 depicts a variation of system 700 in which quench roll 712 is eliminated. Film 780 is heated by airflow 772 from nozzle 770 sufficiently to melt or sufficiently softened to allow film material to flow into nanoholes 706, the flow being driven by surface tension. FIG. 34 depicts another variation of system 700 in which rather than supplying film 780 to chill roll 702, melted polymer 720 is applied to chill roll 702 in the same manner as polymer 520 is applied to chill roll 502 of system 500 (see FIG. 24). The temperatures of melted polymer 720, chill roll 702, and heated air flow 772 from nozzle 770 are selected so that surface tension draws polymer 720 into nanoholes in the surface of chill roll 702. With subsequent cooling by flow 778 from nozzle 776, polymer 710 coating cylindrical surface 704 is cooled sufficiently to allow chilled film 782 with nanofibers 784 to be peeled from cylindrical surface 704 of chill roll 702.

Figure 35A:
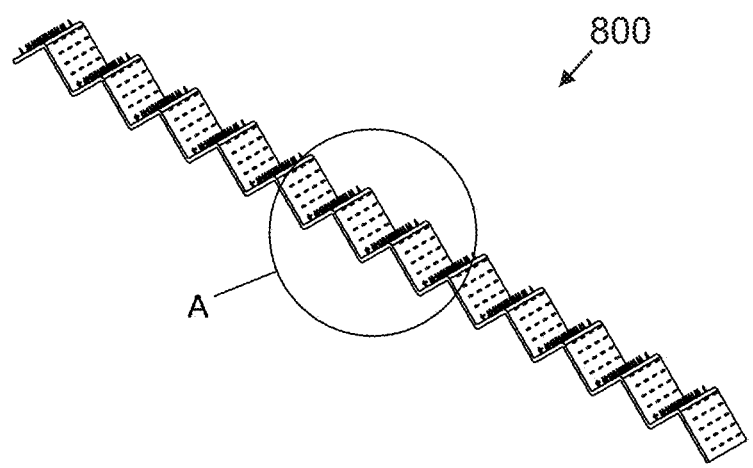
FIG. 35A is a perspective view of a segment of an alternate embodiment nanofiber-bearing bioribbon of the present invention.
Figure 35B:
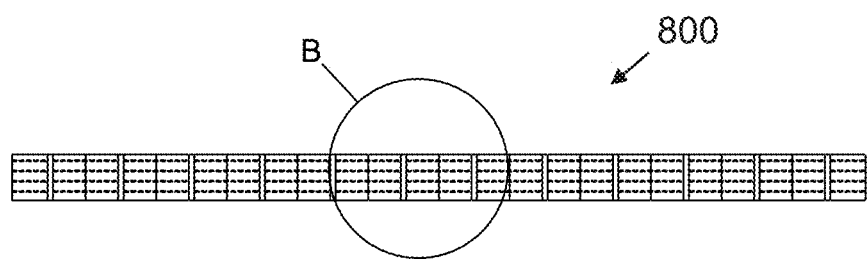
FIG. 35B is a plan view of the bioribbon of FIG. 33.
Figure 35C:
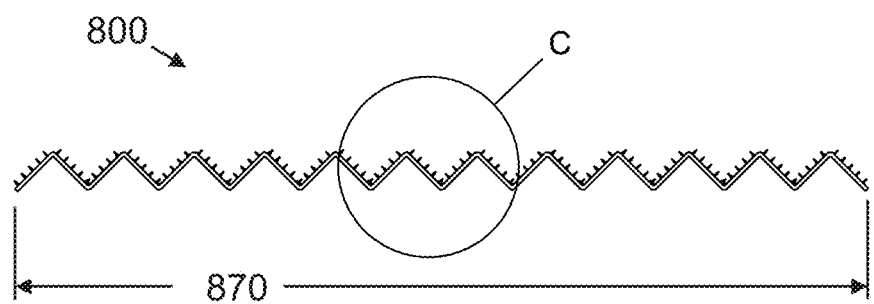
FIG. 35C is a side elevational view of the bioribbon of FIG. 33.
Figure 36:
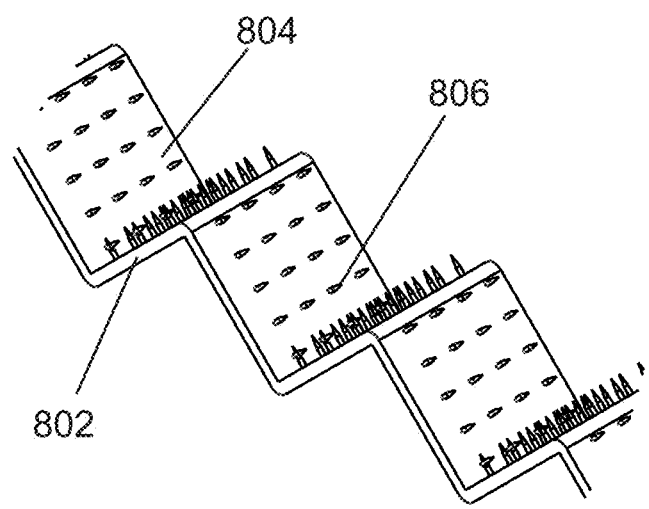
FIG. 36 is an expanded view of the bioribbon of FIG. 35A at location A.
Figure 37:
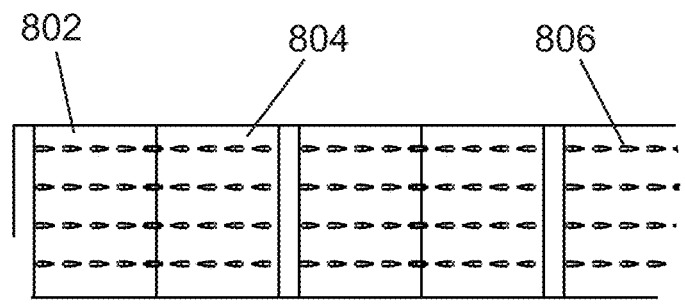
FIG. 37 is an expanded view of the bioribbon of FIG. 35B at location B.
Figure 38:
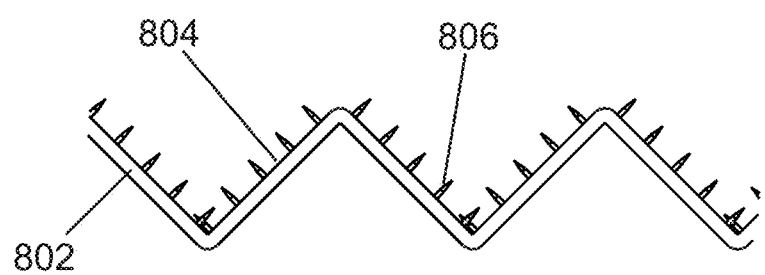
FIG. 38 is an expanded view of the bioribbon of FIG. 35C at location C.
Figure 39:
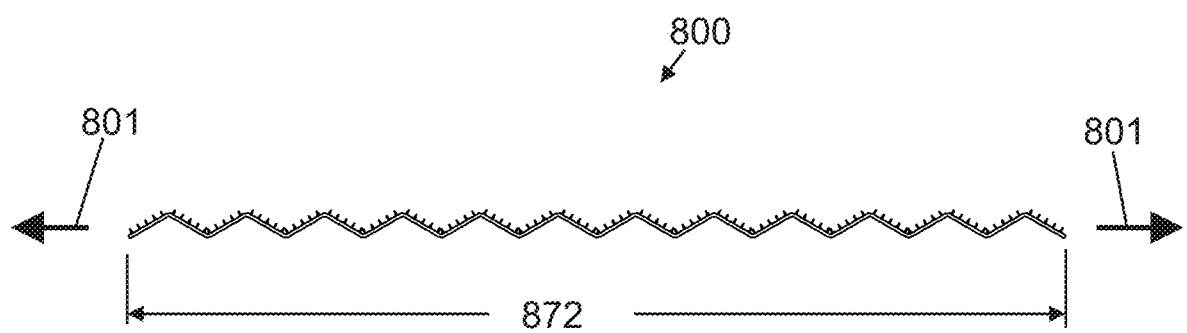
FIG. 39 is a side elevational depiction of the bioribbon of FIG. 35A subjected to a tensile force.
Figure 40:
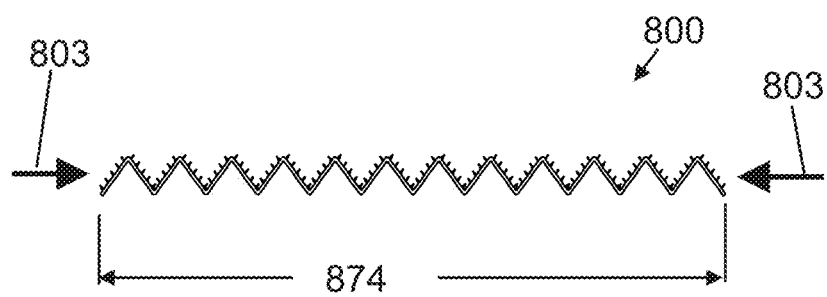
FIG. 40 is a side elevational depiction of the bioribbon of FIG. 35A subjected to a compressive force.
Figure 41:
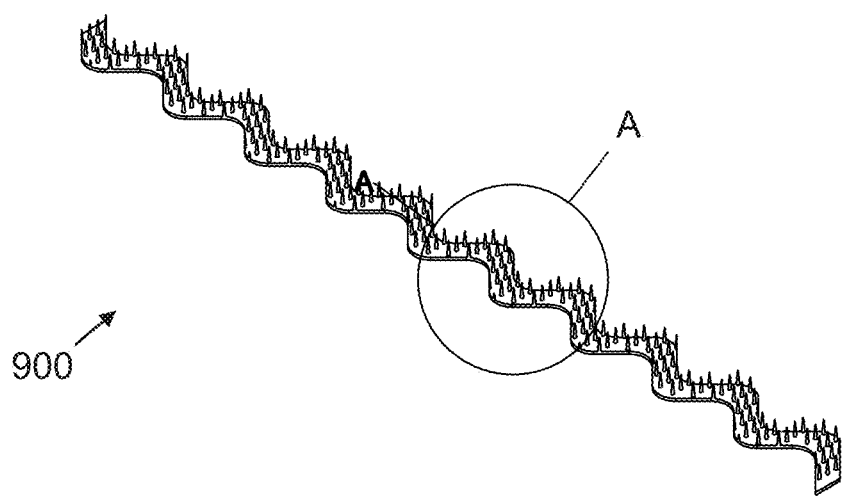
FIG. 41 is a perspective view of a segment of an alternate embodiment bioribbon of the present invention.
Figure 42:
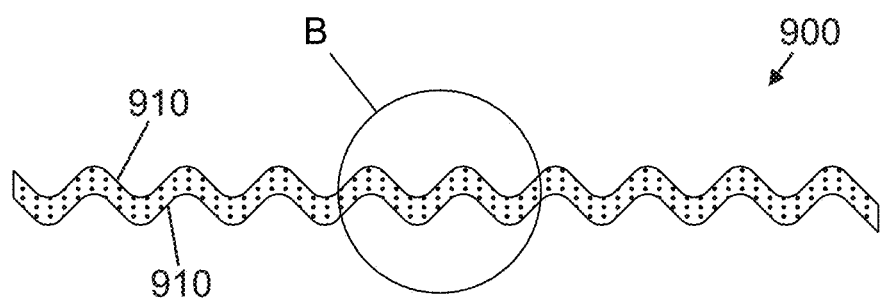
FIG. 42 is a plan view of the bioribbon of FIG. 41.
Figure 43:
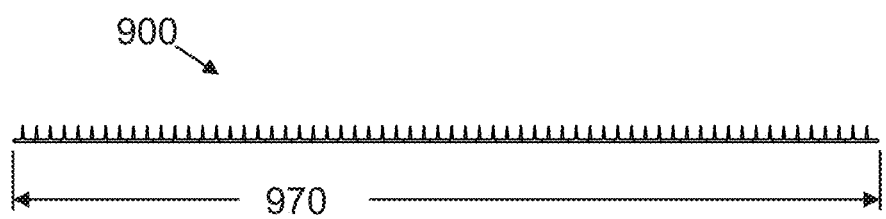
FIG. 43 is a side elevational view of the bioribbon of FIG. 41.
Figure 44:
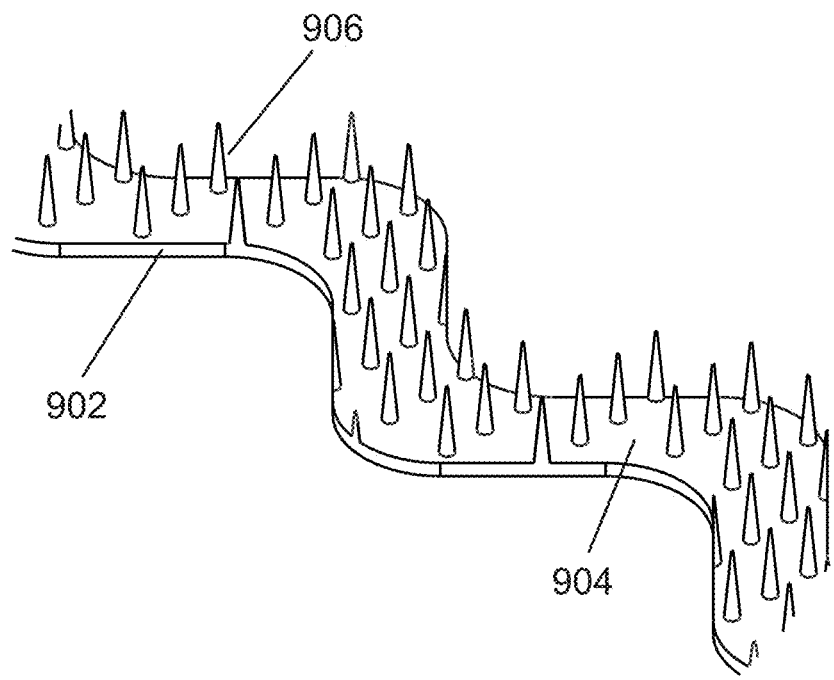
FIG. 44 is an expanded view of the bioribbon of FIG. 41 at location A.
Figure 45:
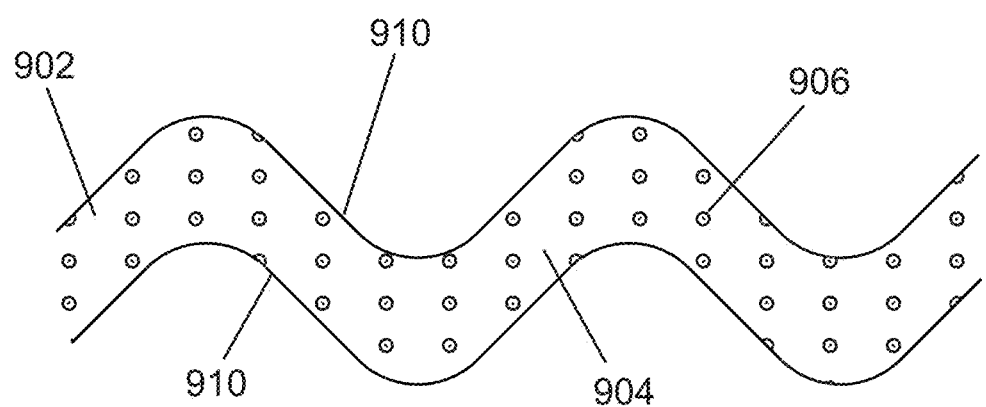
FIG. 45 is an expanded view of the bioribbon of FIG. 42 at location B.
Figure 46:
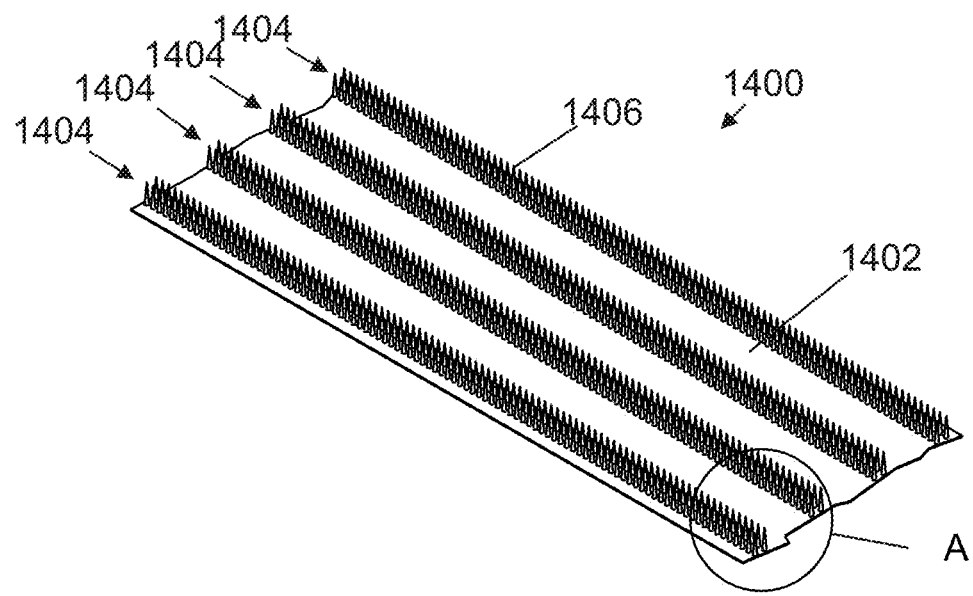
FIG. 46 is a perspective view of a portion of an embodiment of a bioribbon of the present invention whereon arrays of nanofibers are configured to direct cellular propagation in a preferred direction.
Figure 47:
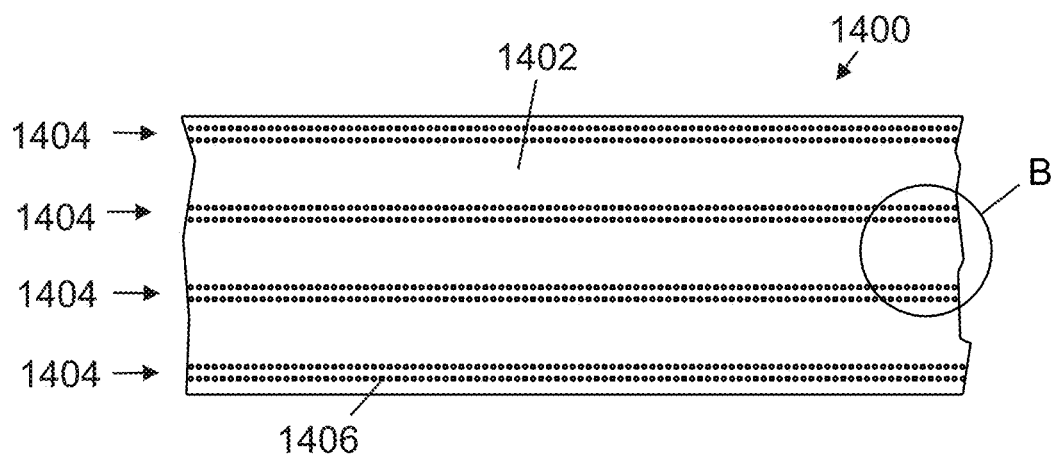
FIG. 47 is a plan view of the bioribbon portion of FIG. 46.
Figure 48:
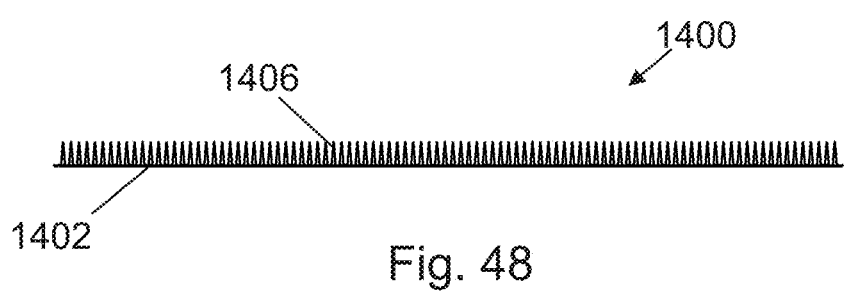
FIG. 48 is a side elevational view of the bioribbon portion of FIG. 46.
Figure 49:
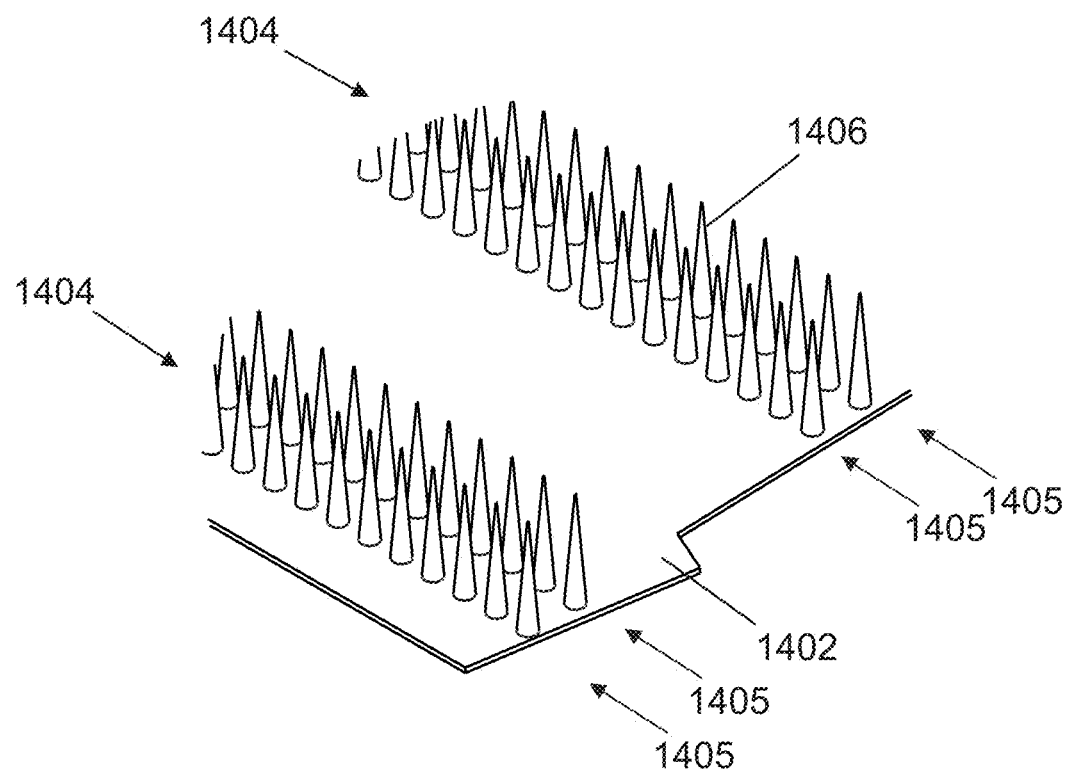
FIG. 49 is an expanded view of the bioribbon portion of FIG. 46 at location A.
Figure 50:
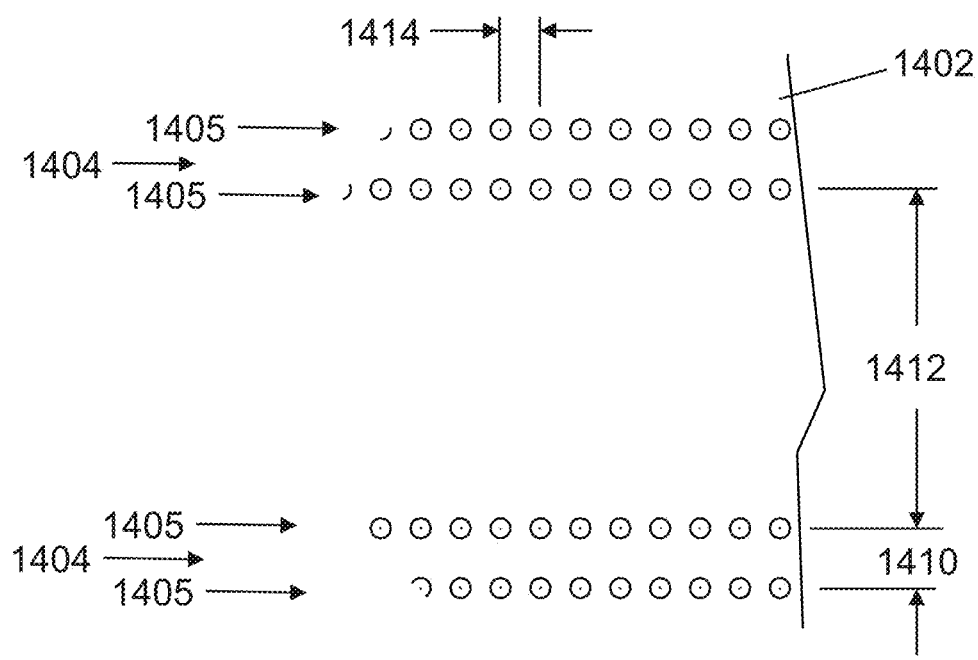
FIG. 50 is an expanded view of the bioribbon portion of FIG. 47 at location B.

Bioribbon 400 depicted in FIGS. 19 through 23 has a flexibly planar film portion 402 of constant width and linear parallel edges. In other embodiments the film portion may be formed to a non-planar configuration so as to impart desired properties to the bioribbon. For instance, film portion 802 of ribbon 800 has an "accordion fold" imparted thereto as depicted in FIGS. 35A through 40. Nanofibers 806 are substantially normal to surface 804 of film portion 802. Bioribbon 800 has an unconstrained length 870 in its unconstrained condition as depicted in FIG. 35C. Because of the accordion fold imparted to ribbon 800, length 870 increases to 872 when ribbon 800 is subjected to a tensile force as depicted in FIG. 39, or decreases to length 874 when ribbon 800 is subjected to a compressive force as depicted in FIG. 40. These length changes of ribbon 800 are accomplished without subjecting film portion 802 to inelastic deformation.

An alternate embodiment bioribbon 900 wherein the unconstrained length may be changed without inelastic deformation is depicted in FIGS. 41 through 45. Unlike previously described bioribbons, as best seen in a plan view as in FIG. 42, edges 910 of film portion 902 of ribbon 900 are not linear, but rather have an undulate shape. Because of this, length 970 may change in response to tensile or compressive loading without inelastic deformation of film portion 902.

In bioribbon embodiments previously herein described, arrays of nanofibers formed on a film portion of the ribbon are arranged in rows with uniform spacing between fibers in the rows, and between adjacent rows. While such arrays are useful for making biomimetic bioribbons for many applications, in others it may be desirable to form more complex arrays to achieve desired outcomes in regenerated tissues. For instance, in certain applications it may be desirable to control the direction of tissue propagation and/or to favor the formation of elongate cells with a preferred orientation. A portion of a bioribbon 1400 configured for directing cellular propagation in the axial direction of the ribbon has nanofiber arrays that form "corn rows" 1404 of closely spaced nanofiber rows that are spaced from the adjacent array 1400 by a second, greater spacing. Referring now to FIGS. 46 through 50, nanofibers 1406 on the surface of film portion 1402 are axially spaced distance 1414 apart in rows 1405. Rows 1405 are spaced distance 1410 apart within arrays 1404. Arrays 1404 are spaced distance 1410 apart. On bioribbon 1400, arrays 1404 are formed of two rows 1405 of nanofibers. In other embodiments arrays 1404 are formed of three or more rows 1405 of nanofibers. In some of these embodiments with three or more rows 1405 of nanofibers, the spacing 1414 between nanofibers within each row 1405 of nanofibers is uniform. In others, the spacing is not, the spacing 1414 of each row 1405 of nanofibers being selected to achieve a desired cell behavior with regard to cell propagation and differentiation.

Bioribbons of the present invention are versatile biomimetic elements that may be formed into scaffolds configured to address a variety of specific requirements. Broadly, scaffolds of the present invention may be grouped into those that have a three-dimensional shape, frequently cylindrical or tubular, or a two-dimensional shape sheet-like shape wherein the thickness of the scaffold is much less than its length or width.

Three-dimensional scaffolds of the present invention are frequently used in the treatment of injuries or discontinuities in elongate tissue structures. Among these are muscles, ligaments, tendons, vessels and peripheral nerves. A requirement for the reconnection of stumps of a severed structure is that the completed repair be tension free. When the length of the proximal and distal stumps is sufficient, the ends of the stumps may be debrided and sutured together. When the length of the stumps is insufficient, the length must be augmented using a graft or scaffold. Three dimensional scaffolds of the present invention for rejoining severed elongate tissue structures are depicted in FIGS. 51 through 62. Hereafter, the form and function of these scaffolds will be described primarily with regard to the treatment of peripheral nerve injuries and discontinuities.

Peripheral Nerve Repair

Peripheral nerves have an inherent ability to regenerate under suitable conditions. When a nerve is severed, the distal portion of the nerve experiences Wallerian degeneration within hours of the injury resulting in degeneration of the axons (nerve cells) and myelin sheath surrounding them. The proximal portion end experiences some retrograde degeneration, but once the debris is cleared, it begins to sprout axons that grow toward the distal portion. The proximal axons are able to grow distally so long as the cell body remains intact. If the growing axons reach the distal end of the severed nerve, regrowth of the neural tissue occurs in the gap so as to restore functioning of the nerve. The regeneration of neural tissue in this manner is generally limited to gaps of five millimeters or less.

Surgical methods to promote the reconstruction of nerve continuity and functions to damaged or severed peripheral nerves depend on the condition of the proximal and distal stumps of the nerve. A requirement for such repairs is that they be tension-free. If the remaining nerve portions have sufficient length for a tension-free repair, the ends may be simply sutured together in technique known as neurorrhaphy. Frequently, however, neurorrhaphy does not restore full neuro function.

The results of rejoining of nerves in a tension-free repair may be improved by providing a "nerve guide", a tubular sheath that surrounds the severed ends during healing. The nerve guide ensures proper alignment and proximation of the nerve ends, prevents the infiltration of fibroblasts and reduces the risk of scar tissue, and forms a scaffold that promotes the regrowth of cells. This cellular regrowth augments the tissue at the repair site so as to reduce stress on the repair. The severed ends of the nerve are sutured to the nerve guide at locations a distance from the repair so as to preserve the integrity of the severed ends. Typical of these nerve guides are the NeuroMend™ Collagen Nerve Wrap products by Stryker Incorporated (Kalamazoo, Mich.), and the Axoguard Nerve Connector™ by AxoGenis (Alachua, Fla.). The NeuroMend products are made of bovine derived collagen. Axoguard Nerve Connectors are made of porcine submucosa extracellular matrix. Synthetic bioabsorbable materials have also been developed for nerve guides. These include PLA, Chitosan, and Gelatin, among others. However, nerve guide scaffolds formed of these materials lack the fibrillar features of the native ECM and therefore are suboptimal for tissue regrowth and propagation.

In some embodiments, bioribbons of the present invention may be formed into tubular scaffolds for nerve guides, or for the reconnection and augmentation of elongate tissue structures such as vessels, tendons, ligaments or muscles, among others. The nanofiber arrays on the surface of the bioribbons mimic the fibrillar structure of the ECM, providing locations for bonding to cells, and for external signaling to cells that are bonded thereto through the configuration of the nanofibers and the matrices formed therefrom. Indeed, the arrangement and spacing of nanofibers within the arrays, and the length and stiffness of the nanofibers can affect cell behavior. These characteristics may be optimized to favor the formation of tissue of a desired type.

Biomimetic tissue scaffolds for the reconnection and augmentation of stumps of elongate tissue structures including peripheral nerves can be formed of bioribbons of the present invention. Typically such scaffolds can be formed by coiling, winding or weaving individual bioribbons or yarns made of multiple ribbons about a mandrel to form a tubular structure and then removing the mandrel. The structure may be held together by the weave, or by a bonding means such as an adhesive or thermal bonding. In some embodiments a mat of ribbons can be wound around the mandrel to form a tubular scaffold. For example, tissue scaffold 1100, shown in FIGS. 54 through 56, can be formed by coiling or winding multiple layers of bioribbons about a mandrel, the wind direction of each layer being counter to that of the layers immediately adjacent to it. The wind direction is sometimes referred to herein as "handedness." For instance, if the first layer 1106 is wound about the mandrel in a clockwise direction, second layer 1104 is wound in the counterclockwise direction, and third layer 1102 is wound in the clockwise direction. As such, each layer of a multi-layered scaffold 1100 supports or is supported by an adjacent layer. The layers are bonded one to another by heat, a suitable adhesive, or other means, after which the mandrel is withdrawn leaving scaffold 1100. Scaffold 1100 is depicted with three wound layers. It will be understood that the number of layers and the helical pitch of the layer coils or windings may be selected to affect the flexibility of the scaffold 1100 and its porosity, properties that may be optimized as required for specific applications. Scaffold 1100 forms a generally tubular body defining a first open end 1101, a second open end 1103, a lumen 1105 extending between the first and second open ends 1101, 1103, and an axis 1107.

Figure 57:
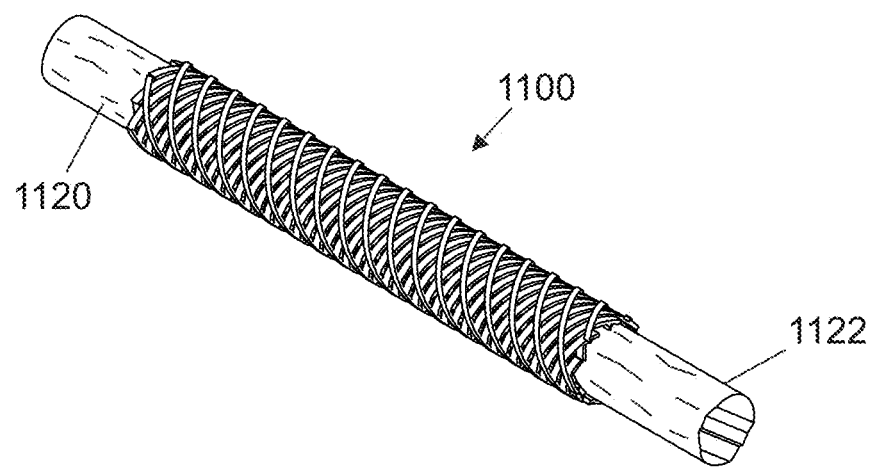
FIG. 57 is a perspective depiction of the tubular tissue scaffold of FIG. 54 in use joining the stumps of an elongate cylindrical severed tissue structure.
Figure 58:
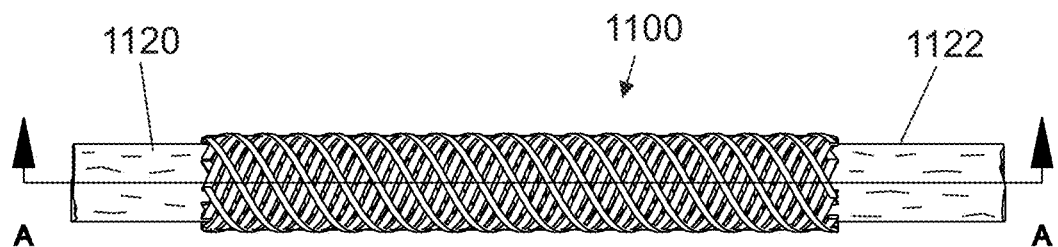
FIG. 58 is a plan view of the objects of FIG. 57.
Figure 59:
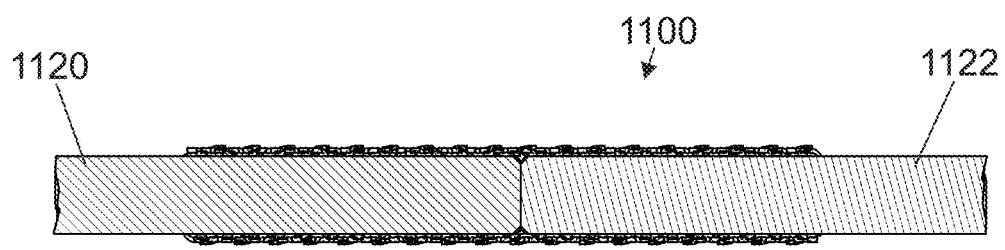
FIG. 59 is a sectional view of the objects of FIG. 58 taken along line A-A.
Figure 60:
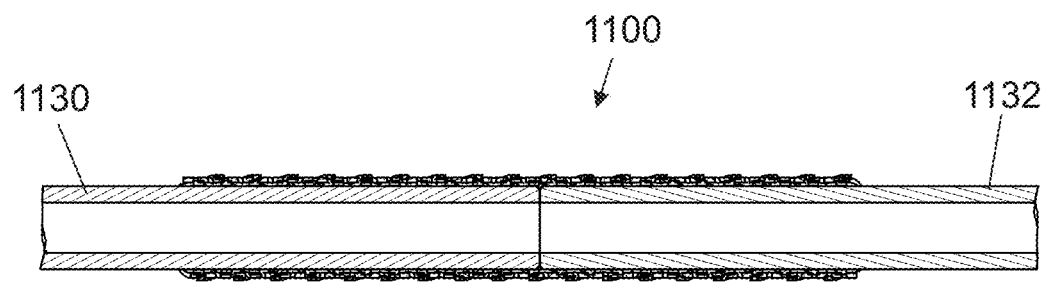
FIG. 60 sectional view taken along an axis of the tubular tissue scaffold of FIG. 54 showing the scaffold used in an end-to-end tensionless repair of an elongate tissue structure.

FIGS. 57 through 59 depict scaffold 1100 joining stumps 1120 and 1122. Scaffold 1100 maintains alignment between the stumps and may be secured to stumps 1120 and 1122 by suturing or a suitable adhesive. FIG. 60 depicts a similar repair in which stumps 1130 and 1132 are proximal and distal portions of a vessel. In FIGS. 59 and 60 stumps 1120 and 1122, and 1130 and 1132 have sufficient length to allow a tension-free repair. In addition to providing alignment and contact between stumps 1120 and 1122, and 1130 and 1132, nanofiber arrays formed on bioribbons forming layers 1102, 1104 and 1106 stimulate tissue growth and regeneration that augments the repair so as to reduce stress on the repaired tissue.

In another embodiment of the present invention similar in form to scaffold 1100, bioribbons are woven together rather than simply formed into counter-wound layers. The woven construct of the scaffold formed is similar in construction to a "Chinese finger trap", a tubular novelty device in which, when the fingers of a subject are inserted into the opposite ends, the fingers cannot be removed by applying tension. The finger trap tightens onto the fingers when an attempt is made to pull the fingers from the trap. In the same manner, a braided scaffold of the present invention formed of bioribbons of the present invention resists axial force applied to proximal and distal tissue stumps placed therein by tightening onto the stumps so as to prevent failure of the repair. This woven scaffold is particularly well suited to the repair of ligaments.

The regeneration of neural tissue in a small gap between the stump ends of a severed nerve may be enhanced by the use of a "nerve conduit", a bioabsorbable tubular implant that covers the proximal and distal ends of the severed nerve so as to direct the axons toward their distal target, and to isolate the region from fibroblasts, to retain Nerve Growth Factor and prevent the formation of scar tissue. Typical of these nerve conduits are NeuroMatrix™ and Neuroflex™ products by Stryker, Incorporated and NeuroGen™ Nerve Guide by Integra Life Sciences, Inc. (Princeton, N.J.). Scaffold 1100 may be used effectively as a nerve conduit, with the added benefit of providing tissue augmentation in the region of the repair so as to prevent failure.

When the remaining stumps of a severed nerve have insufficient length to allow tension-free direct reconnection or reconnection with a small gap using a nerve conduit, a graft may be used in the repair to achieve the required length. In the case of an autograft, a graft is harvested from a remote part of the patient's body, a time-consuming procedure with associated morbidity. Alternatively, a human nerve allograft like, for instance, the Avance Nerve Graft by AxoGen, Incorporated, may be used. The Avance Nerve Graft product is a decellularized human nerve allograft that retains structures of extracellular matrix. The graft serves as a scaffold that facilitates the growth of axons through the graft so as to bridge gaps greater than five millimeters. The fibrillar structure of collagen forming the graft provides a temporary ECM during axon regrowth.

Figure 51:
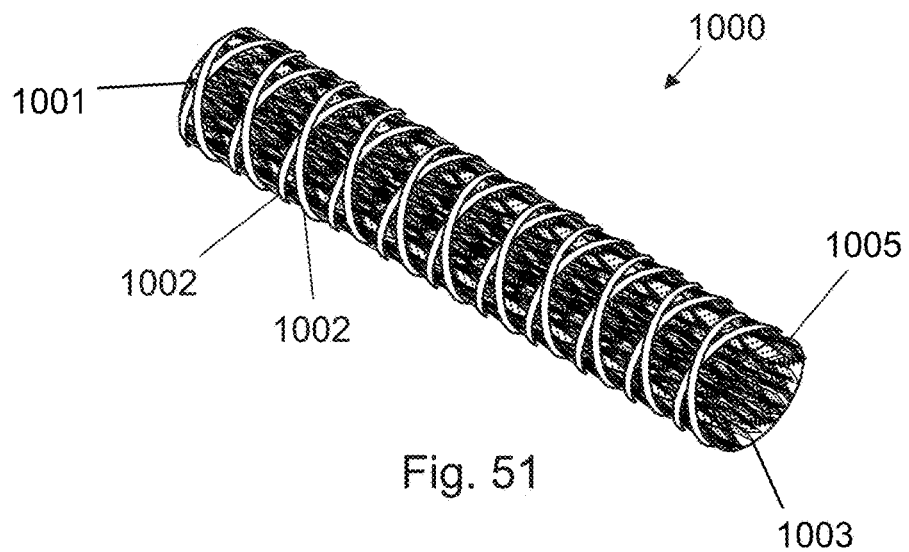
FIG. 51 is a perspective view of an embodiment of an elongate tissue scaffold of the present invention formed of a bundle of bioribbons.
Figure 52:
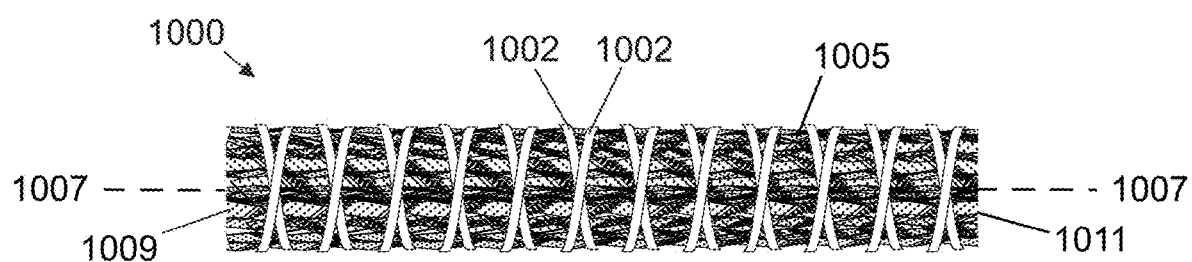
FIG. 52 is a plan view of the objects of FIG. 51.
Figure 53:
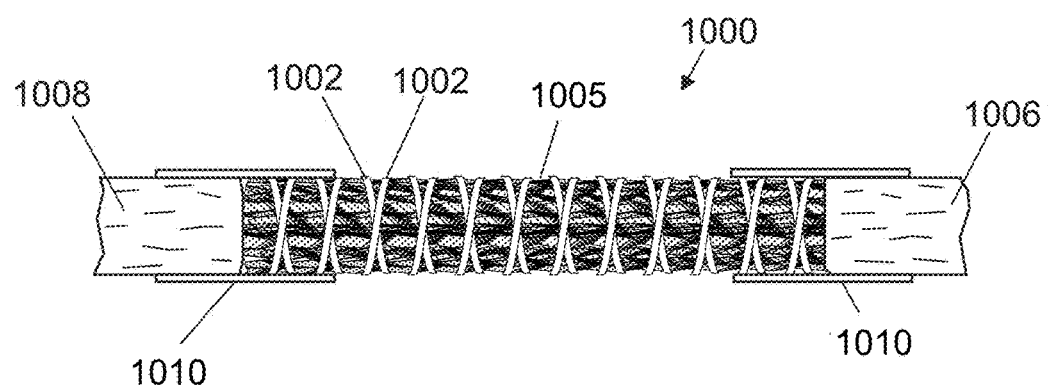
FIG. 53 depicts the scaffold of FIG. 51 in use forming a tension-less rejoining of the stumps of a severed elongate tissue structure.
Figure 54:
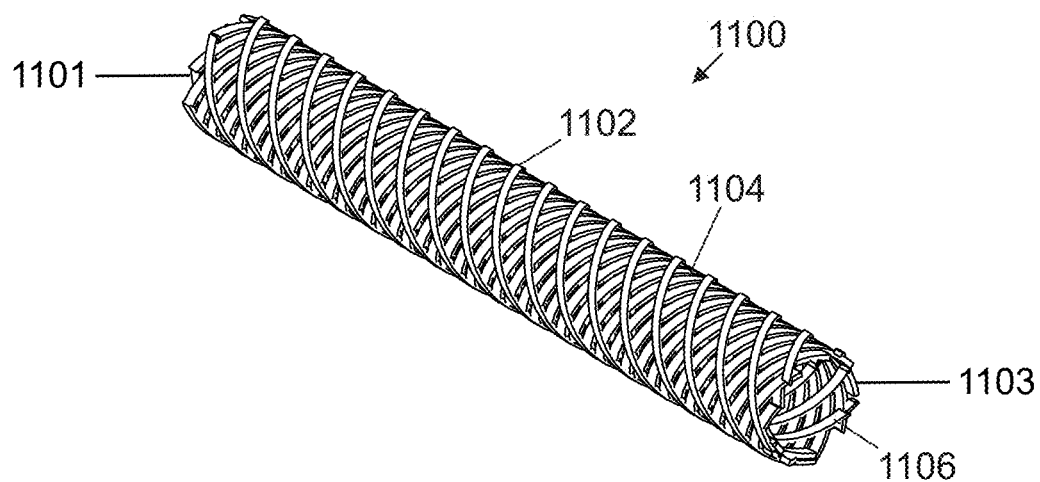
FIG. 54 is a perspective depiction of an embodiment of a tubular tissue scaffold of the present invention formed of bioribbons of the present invention.
Figure 55:
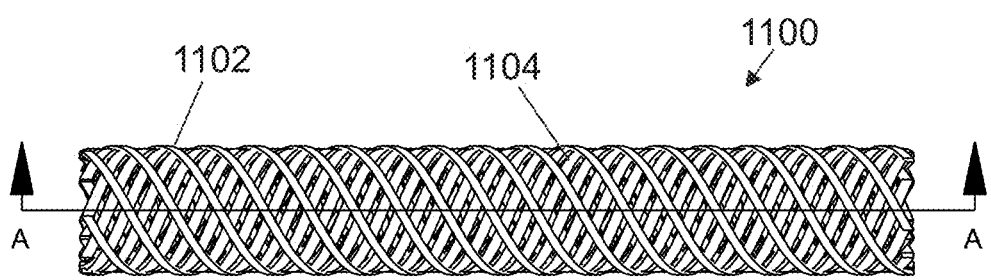
FIG. 55 is a plan view of the objects of FIG. 54.
Figure 56:
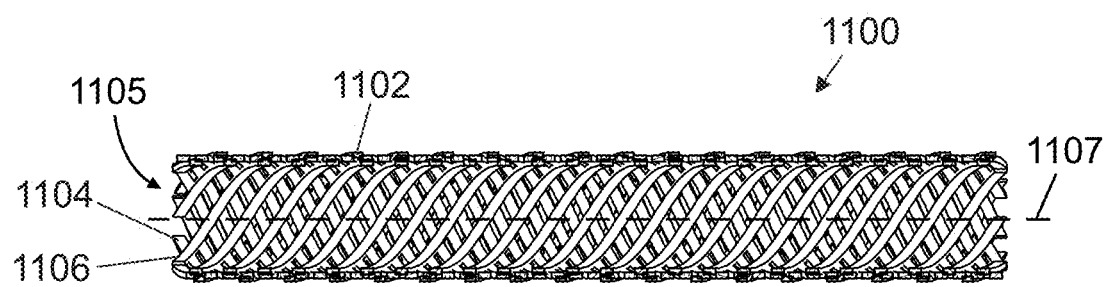
FIG. 56 is a sectional view of the objects of FIG. 55 taken along line A-A.

Bioribbons of the present invention may be formed into biomimetic tissue scaffolds that function as a temporary extracellular matrix, the nanofiber arrays of the ribbons providing sites for adhesion for growing cells, and affecting cell behavior through engineered properties of the nanofibers and arrays of which they are formed. FIGS. 51 through 53 depict a biomimetic scaffold 1000 of the present invention useful in the treatment of a severed elongate tissue structure like, for instance, a peripheral nerve, a tendon or a ligament. If the length of the stumps is insufficient to allow tension-free direct reconnection, it is necessary to insert a tissue graft or a tissue scaffold of sufficient length to make the repair tension-free. Scaffold 1000 is formed of a bundle of bioribbons 1005 wrapped with bioabsorbable bands 1002. The bioribbons 1005 forming scaffold 1000 can be arranged to form an elongated body having a first end 1001, a second end 1003, an axis 1007, and a generally circular cross section. As such, in some embodiments, the scaffold 1000 can be cylindrical. In addition, each bioribbon 1005 of the bundle has a first end 1009 and a second end 1011 and the bioribbons are arranged such that the first and second ends 1001, 1003 of each bioribbon are coterminous with the respective first and second ends of each other bioribbon in the bundle. Additionally, each bioribbon 1005 contacts at least one other bioribbon 1005 of the bundle. In a preferred embodiment, bioribbons 1005 are like bioribbon 800 (FIGS. 35A through 40) or bioribbon 900 (FIGS. 41 through 45) so as to give scaffold 1000 flexibility. In a preferred embodiment, the nanofiber arrays formed on bioribbons forming bioribbon bundle 1005 have a corn-row configuration like bioribbon 1400 (FIGS. 46 to 50) so as to direct cell propagation axially through scaffold 1000 along surfaces of bioribbons 1005 and in spaces formed between bioribbons 1005. FIG. 53 depicts scaffold 1000 used in a repair, joining first stump 1006 to second stump 1008. Scaffold 1000 is aligned with and secured to stumps 1006 and 1008 by bioabsorbable sleeves 1010, sleeves 1010 being secured to scaffold 1000 and stumps 1006 and 1008 by suturing or use of a suitable adhesive.

Figure 61:
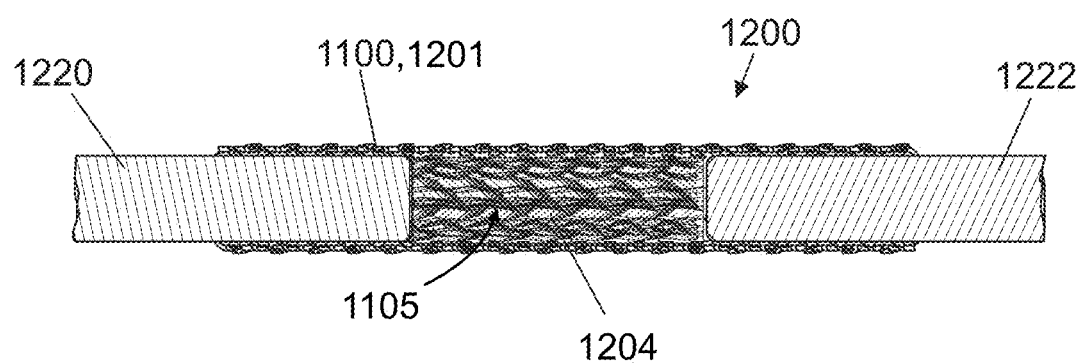
FIG. 61 is an axial sectional view of an embodiment of a biomimetic tissue scaffold including axially oriented bioribbons positioned within the tubular tissue scaffold of FIG. 54.

FIG. 61 depicts a tissue scaffold 1200 of the present invention for rejoining elongate tissue structures wherein the combined length of stumps 1220 and 1222 is insufficient for tension-free repair. Stumps 1220 and 1222 may be the proximal and distal portions of a severed elongate structure such as, for instance, a tendon, ligament, nerve or muscle. Scaffold 1200 has a tubular outer portion 1201 formed of scaffold 1100, and an inner portion 1204 positioned in the lumen 1105 thereof, the inner portion 1204 being formed of bioribbons 1005 configured as previously described in scaffold 1000 (FIGS. 51-53). Bioribbons 1005 can substantially fill at least a portion of the length of the lumen 1105. By "substantially fill" it is meant that each bioribbon 1005 contacts at least one other bioribbon 1005 while the bioribbons 1005 forming the exterior surface of the bundle of bioribbons 1005 also contact an interior surface of the scaffold 1100 forming tubular outer portion 1201.

Figure 62:
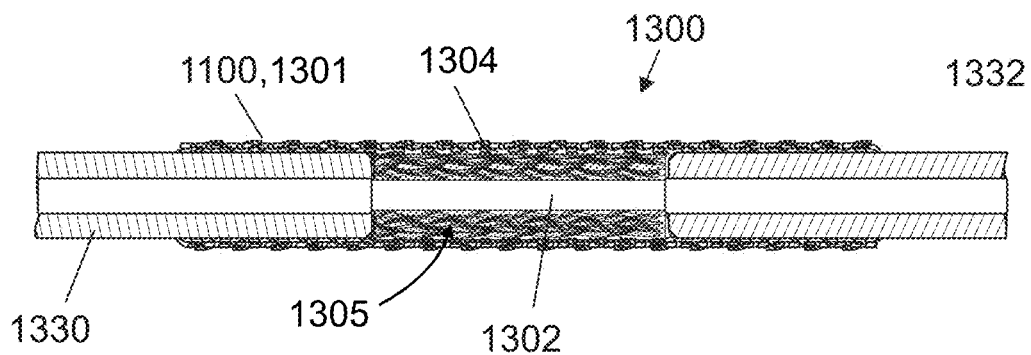
FIG. 62 is an axial sectional view of an embodiment of a biomimetic tissue scaffold including axially oriented bioribbons positioned within the tubular tissue scaffold of FIG. 54 so as to define a central lumen.
Figure 63:
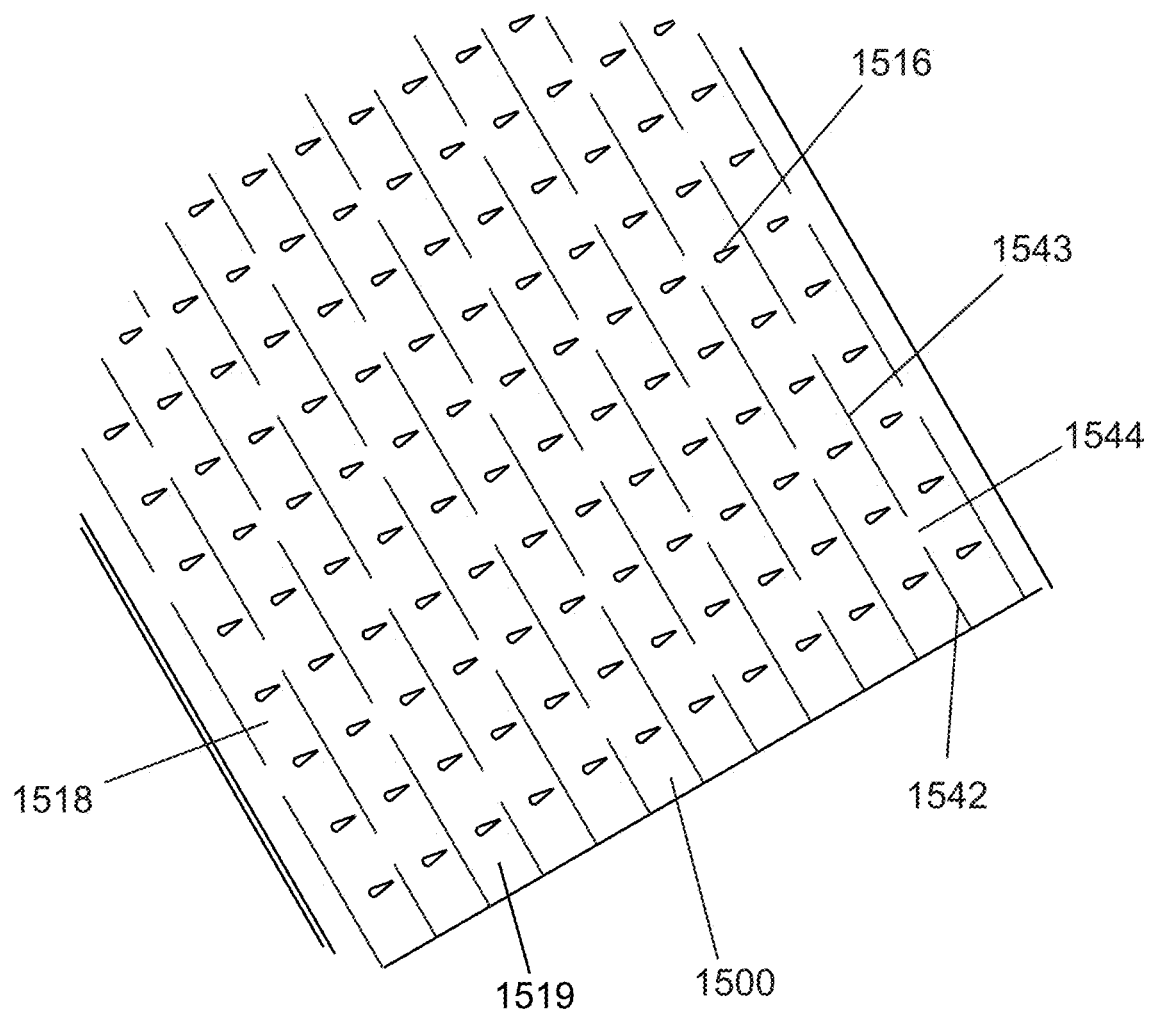
FIG. 63 is a perspective view of an alternate embodiment of an elongate film element in which intermittent slitting of the film resulted in a plurality of bioribbons that are locally joined one to another.
Figure 64:
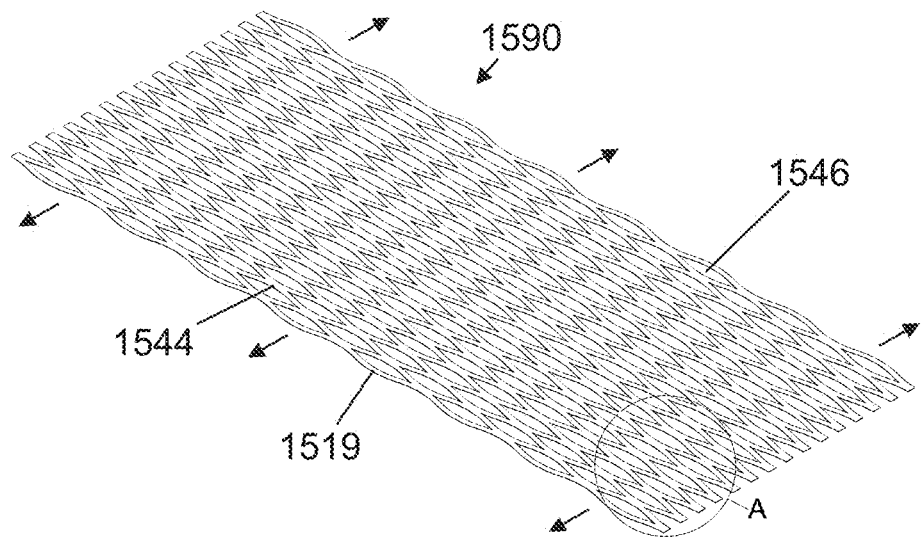
FIG. 64 is a perspective view of an embodiment of a nanofiber mesh formed by laterally expanding the film element of FIG. 63.
Figure 65:
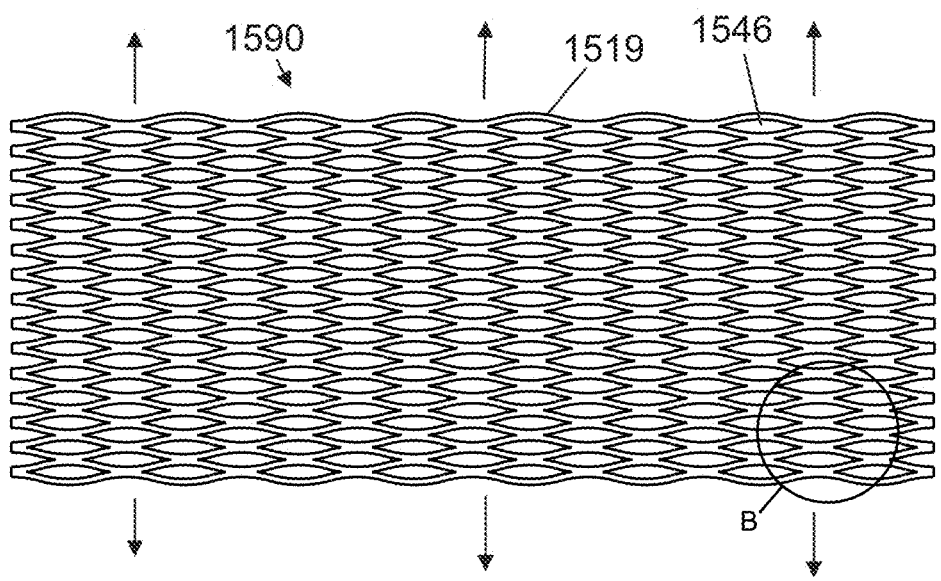
FIG. 65 is a plan view of the mesh of FIG. 64.
Figure 66:
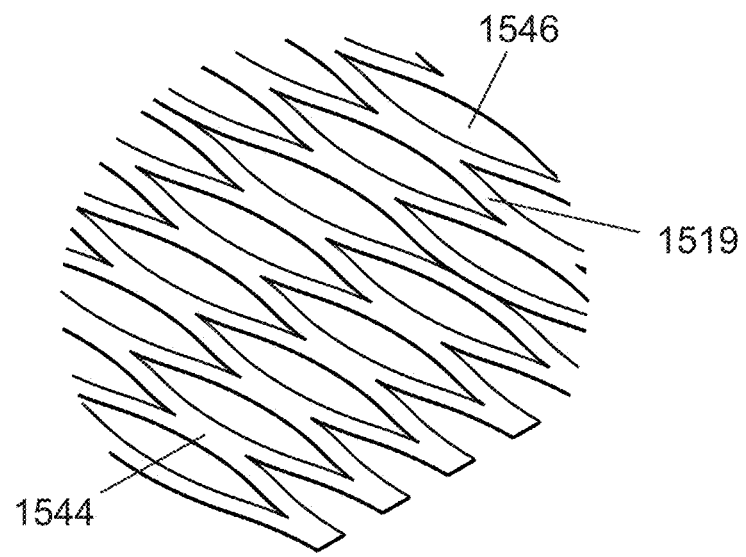
FIG. 66 is an expanded view of the mesh of FIG. 64 at location A.
Figure 67:
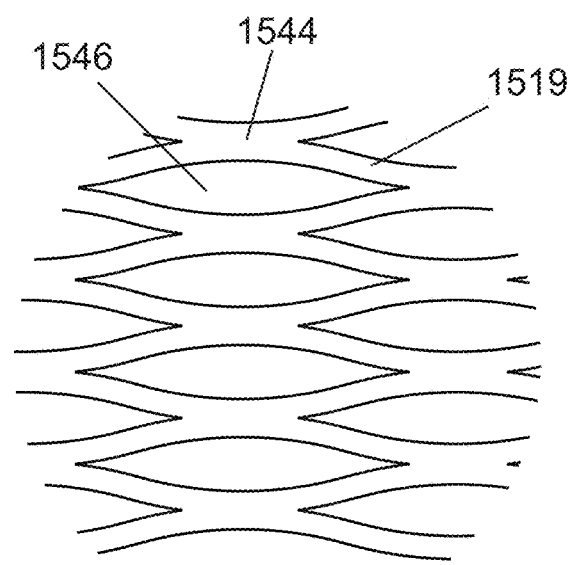
FIG. 67 is an expanded view of the mesh of FIG. 65 at location B.

FIG. 62 depicts a tissue scaffold 1300 that is identical in all aspects of form and function to scaffold 1200 except that inner portion 1304 of scaffold 1300 has a central lumen 1302 formed therein. Scaffold 1300 may be used to rejoin elongate luminal structures including ducts of various types. Tissue stumps 1330 and 1332 may be the proximal and distal portions of, for instance, a blood vessel, a lymphatic duct, or a vas duct, among others. Tissue scaffolds 1200 and 1300 each provide alignment through tubular portions 1100, and provide a scaffold 1204, 1304, respectively, for the regrowth of tissue in the gap between the tissue stumps.

In tissue scaffolds of the present invention previously herein described the bioribbons that make up the scaffolds are independent elongate elements that are formed into a desired construct and retained in that form by mechanical means, weaving, or a suitable bonding method. In other embodiments, a plurality of bioribbons are bonded one to another at predetermined locations of the lateral edges of the film portion of the bioribbons. Applying a lateral spreading force to the plurality of joined bioribbons causes them to spread to create a structure resembling a mesh, the relative proportion of area of the mesh openings relative to the ribbon area being determined by the degree of lateral spread.

Referring now to FIGS. 63 through 67, film 1518 is identical to film 518 depicted in FIG. 26 in all aspects of form and function except as subsequently herein described. Slits 1542 of film 1518 are not continuous like slit 542. Rather, slit 1542 is formed of cut portions 1543 separated by uncut portions 1544, the uncut portions 1544 in adjacent slits 1542 being longitudinally offset such that the uncut portions 1544 are centered in the cut portions 1543 of adjacent slits 1542. Bioribbons 1519 forming film 1518 are each joined to their adjacent ribbons 1519 by uncut portion 1544 of slit 1542. Applying lateral force to the edges of film 1518 as depicted by arrows in FIGS. 64 and 65 causes cut portions 1543 of slit 1542 to spread open to create mesh 1590, cut portions 1543 forming openings 1546. Portions of ribbons 1519 forming boundaries of openings 1546 are deformed by a twisting action when film 1518 is spread to form mesh 1590. Mesh 1590 is flexible and able to conform to a surface to which it is applied. The twisted portions of ribbons 1519 make mesh 1590 locally increase the thickness of mesh 1590 so that multiple meshes 1590 may be stacked one upon another with space created between their adjacent ribbons 1590 so that flow spaces are created not only through meshes 1590 via openings 1546 but also between meshes 1590 by spaces created by the twisted ribbons 1519 of adjacent meshes 1590.

For example, an embodiment of tissue scaffold 1100 (FIGS. 54 through 60) may be formed by wrapping multiple layers of mesh 1590 around a mandrel and securing or bonding them in the manner previously disclosed. Similarly, ribbons 1005 of scaffold 1000 (FIGS. 51 through 53) may be replaced by a coiled mesh 1590, and scaffolds 1200 and 1300 (FIGS. 61 and 62) may be formed in the same manner.

Figure 68:
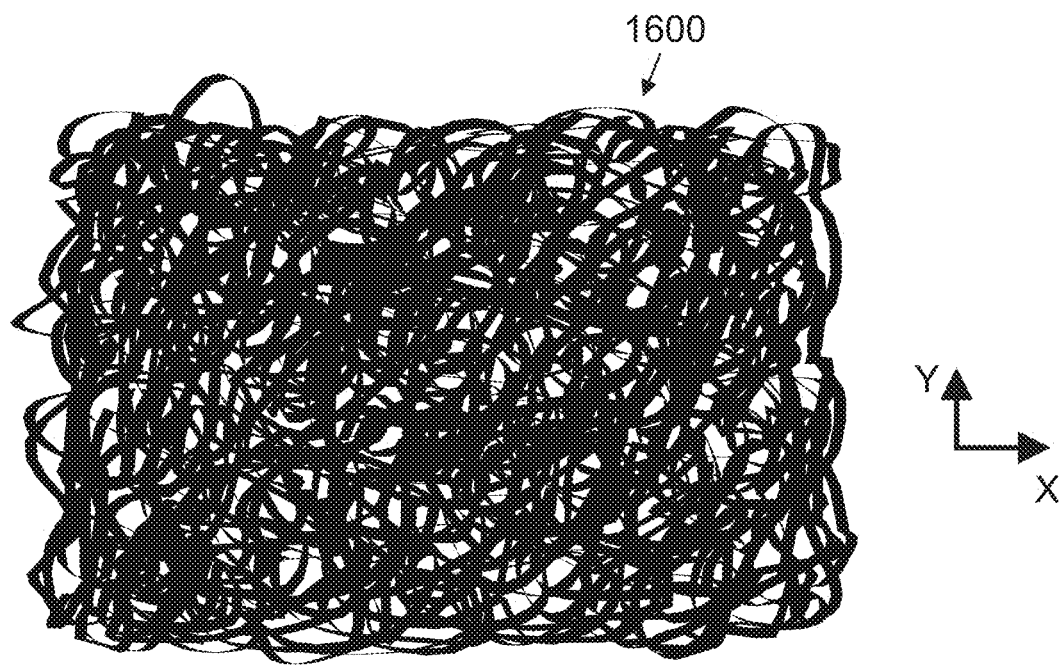
FIG. 68 is a plan view of randomly oriented bioribbons forming a non-woven mat.
Figure 69:
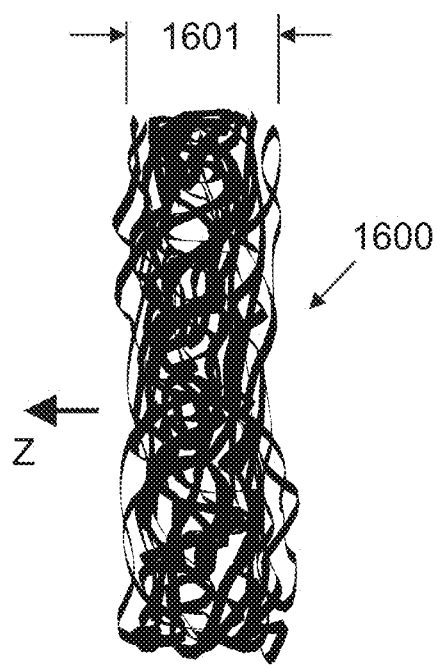
FIG. 69 is an edge view of the objects of FIG. 68.
Figure 70:
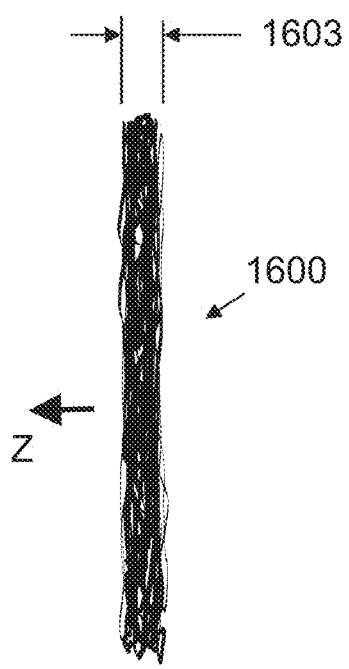
FIG. 70 is an edge view of a non-woven fabric formed from the mat of FIG. 68 wherein the mat has been compressed to form the fabric.

In other embodiments of the present invention, bioribbons of the present invention are formed into three-dimensional scaffolds that may be configured to meet specific requirements. FIGS. 68 and 69 depict a non-woven mat 1600 of bioribbons of the present invention. Each bioribbon forming mat 1600 supports or is supported by another bioribbon. Mat 1600 has an initial thickness 1601. In FIG. 70 mat 1600 has been compressed to thickness 1603 to form a non-woven scaffold 1607. The non-woven scaffold 1607 can be a flexible planar scaffold. In some embodiments scaffold 1607 is a non-woven fabric with ribbons bonded one to another by a suitable bonding method that may be incorporate a bonding agent, or heat, or a combination of the two. In other embodiments the fabric construct is maintained by needle punching (needling), a process in which barbed needles penetrate through the non-woven fiber mat so that fiber segments are reoriented and migrated from the surface of the mat towards the interior, in the process becoming perpendicular to the surface of the mat. The fiber mat is penetrated by multiple needles at numerous locations with predetermined spacing so that these perpendicular fibers create a complex three-dimensional coherent structure.

In contrast to other nanofiber scaffolds formed by electrospinning, scaffold 1607 has tensile strength, and a resistance to compression that allows it to maintain its three-dimensional characteristics. Indeed, although thickness 1603 may be reduced by compressive forces during use, because of the structural properties of the nanofiber bearing bioribbons, the scaffold will not be reduced to a thin membrane-like structure as may be the case with scaffolds formed by elongate nanofibers made by electrospinning.

As previously herein described, the nanofibers and arrays of nanofibers formed on the bioribbons of scaffold 1607 may be optimized so that the outside-in signaling provided to cells growing within scaffold 1607 causes a preferred behavior in the cells. For instance, the nanofiber array characteristics may be selected to favor the differentiation of stem cells within scaffold 1607 in a particular cell type such as muscle, ligament, or skin.

Figure 73:
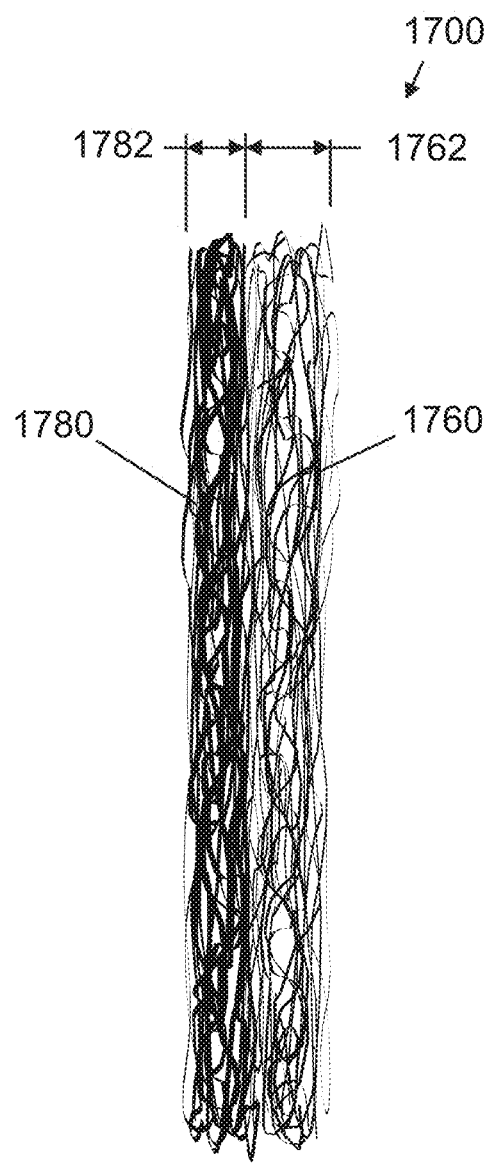
FIG. 73 is an edge view of another alternate embodiment biomimetic tissue scaffold of the present invention having a laminar construction, wherein two laminae are each configured to affect regeneration of a different tissue type.
Figure 74:
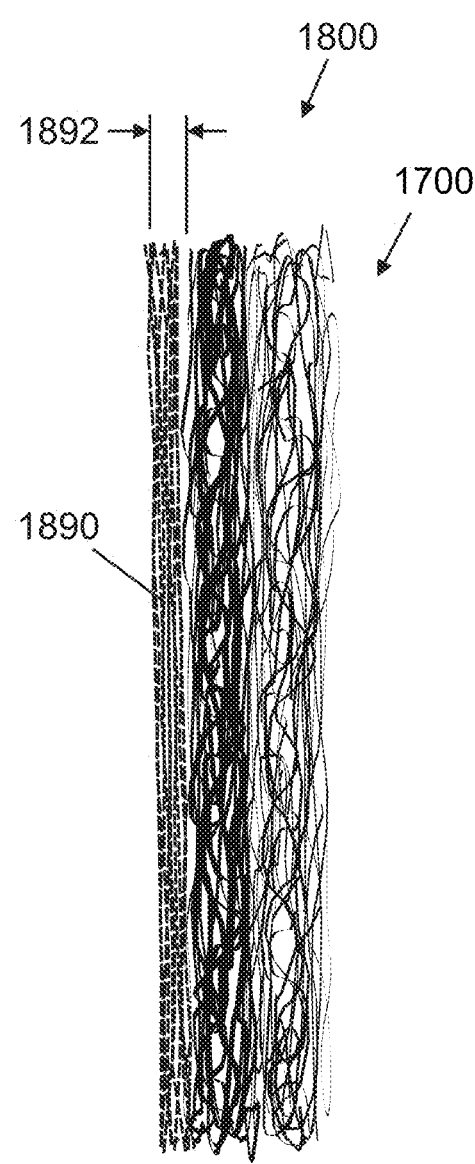
FIG. 74 is an edge view of yet another alternate embodiment biomimetic scaffold of the present invention having a laminar construction, wherein three laminae are each configured to affect regeneration of a different tissue type.

Accordingly, scaffolds formed of mats or non-woven fabrics of bioribbons of the present invention with optimized nanofiber array characteristics to favor a selected cell behavior or type may be combined so as to optimally regenerate more complex tissue structures. For instance, scaffold 1700 depicted in FIG. 73 has a layered construction formed of scaffold portion 1760 of thickness 1762 and scaffold portion 1780 of thickness 1782, portions 1760 and 1780 being each configured to affect a specific tissue effect. Portion 1760 may be optimized for the differentiation of stem cells into, for instance, muscle, while portion 1780 is optimized for the growth of dermal tissue. In FIG. 74, scaffold 1800 is formed of scaffold 1700 and an overlying layer 1890, layer 1890 being a biomimetic scaffold portion formed of one or more laminae of mesh 1590 (FIGS. 64 through 67). Each scaffold portion may be optimally configured for the propagation of a preferred cell type. For instance, portion 1760 may be optimized for the growth of subcutaneous tissue, 1780 for dermis, and 1890 for epidermal tissue.

Chronic wounds lack the ability to regenerate fully functional tissue with current treatment methods. Such wounds may have a variety of causes, but most commonly result from insufficient blood flow at the site. Among the types are pressure-induced skin and soft tissue injuries, usually formed over a bony prominence, ulcers due to venous insufficiency, arterial ulcers due to atherosclerosis and its associated restricted blood flow, diabetic foot ulcers, and non-healing surgical wounds. These wounds result in decreased quality of life and chronic pain for patients and require long-term treatment with its associated high costs. The recurrence rates for these injuries are high. The current standard of care currently focuses on compression, infection control, debridement, and selecting an appropriate dressing that maintains a moist wound healing environment.

There is a need for biomimetic scaffolds that support and induce the appropriate healing response, and that provide protection for the site. These scaffolds must not only be biodegradable and biocompatible, but must have suitable biomechanical properties and structures that facilitate cell propagation and differentiation into desired cell types. In short, the scaffold must mimic the ECM in its structure, particularly with regard to attachment sites for cells to the scaffold. In native tissue cells attach to the ECM via collagen tendrils—structures that through their properties provide cues for cell behavior.

Biomimetic scaffolds of the present invention formed with bioribbons having nanofiber arrays that mimic features of the ECM are ideally suited for this use. Because they are made of fully synthetic polymers rather than biologic materials their mechanical properties are consistent and may be optimized for specific applications. Additionally, there is no risk of disease transmission. Scaffolds formed of bioribbons have interstitial spaces for tissue propagation. Some surfaces defining these interstitial spaces have formed on them nanofiber arrays with characteristics that mimic tendrils of the native ECM for a desired cell type. The scaffold supports cellular ingrowth and regeneration of a desired tissue, and degrades in a manner that favorably affects tissue formation. These benefits all derive from the formation of tuned nanofiber arrays formed on a surface of the bioribbons. These, in turn, are enabled by the unique methods used to form the bioribbons.

Figure 75:
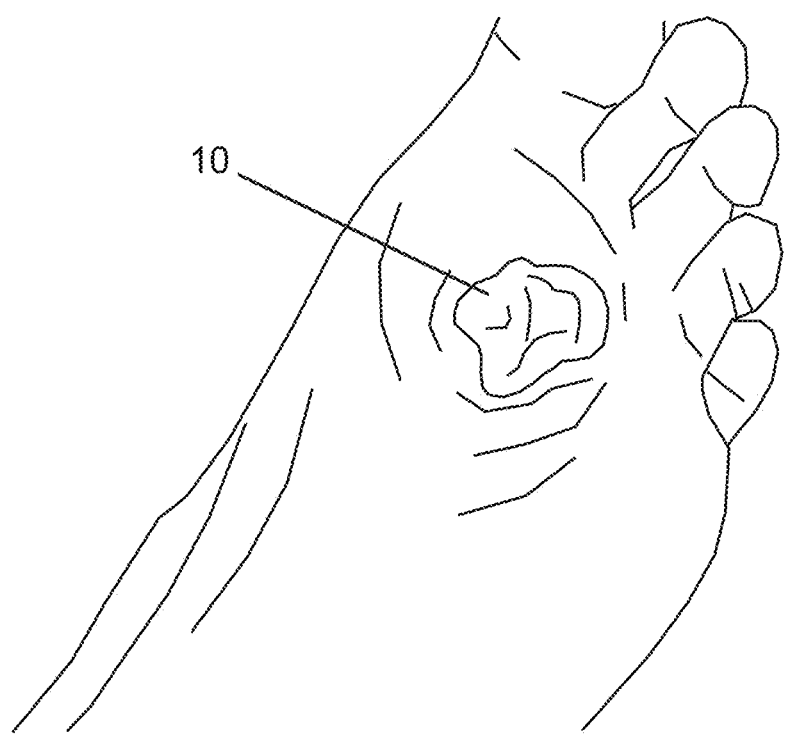
FIG. 75 depicts a chronic wound in need of repair on the foot of a patient.
Figure 76:
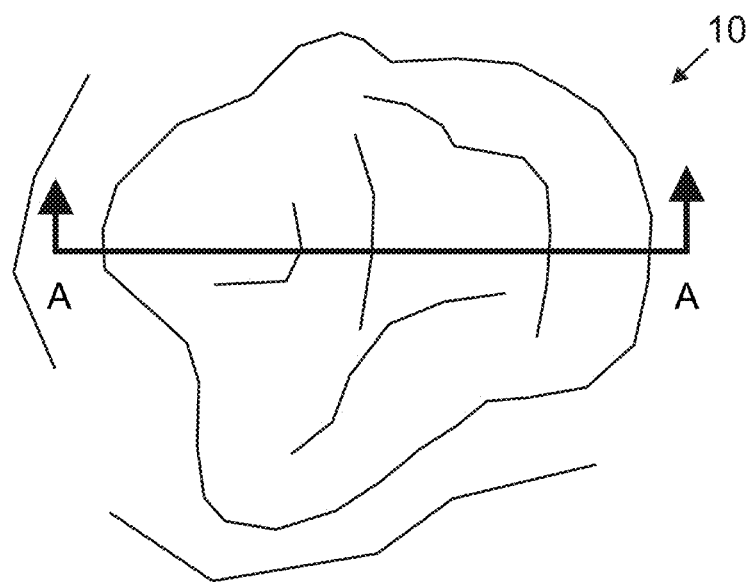
FIG. 76 is an expanded view of the wound of FIG. 75.
Figure 77:
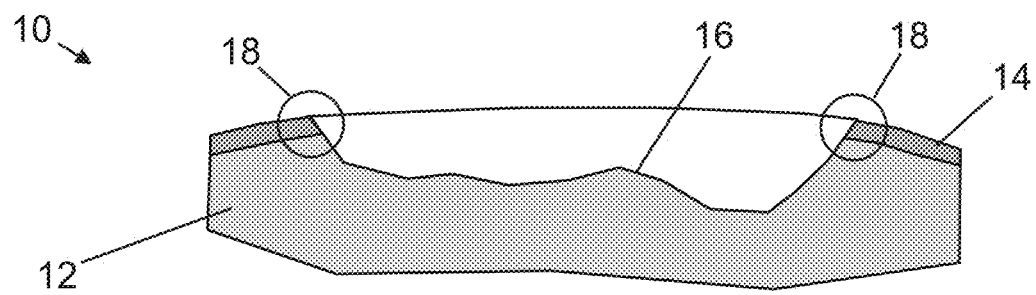
FIG. 77 is a sectional view of the wound of FIG. 76 taken along line A-A.
Figure 78:
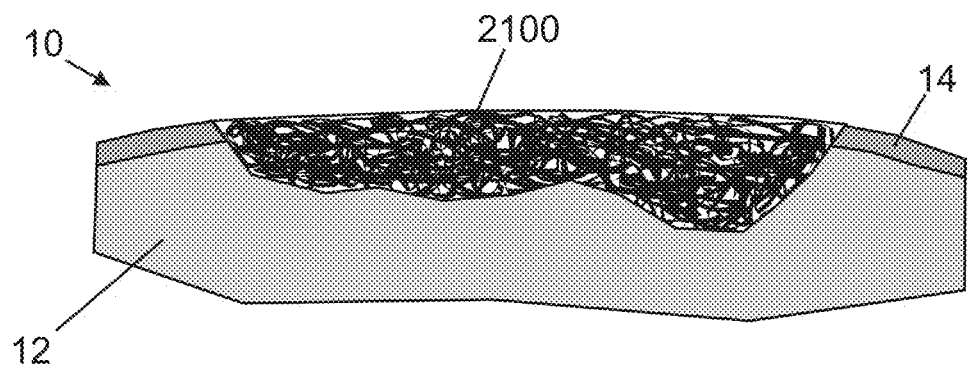
FIG. 78 shows the wound of FIG. 77 implanted with bioribbons of the present invention to form a biomimetic tissue scaffold.
Figure 79:
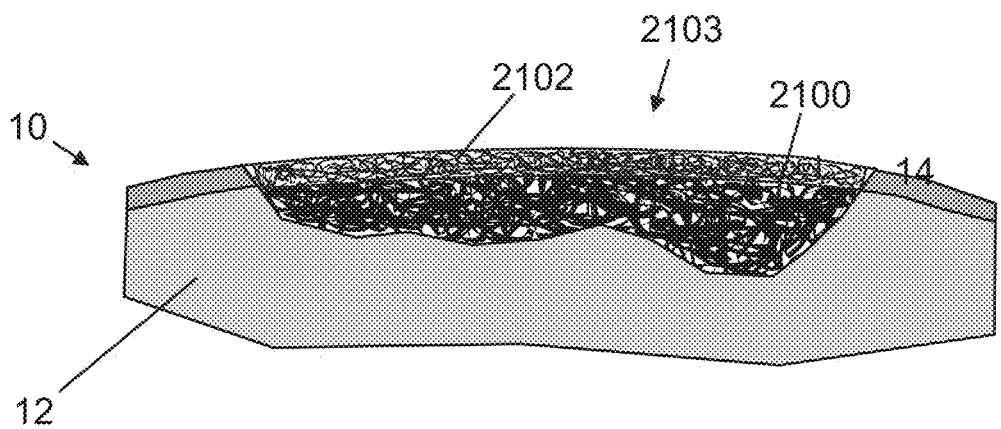
FIG. 79 shows the wound of FIG. 77 implanted with an embodiment of a multi-layered biomimetic tissue scaffold of the present invention formed of two uniquely configured layers, each containing bioribbons with nanofibers optimized for regeneration of a different tissue type.
Figure 80:
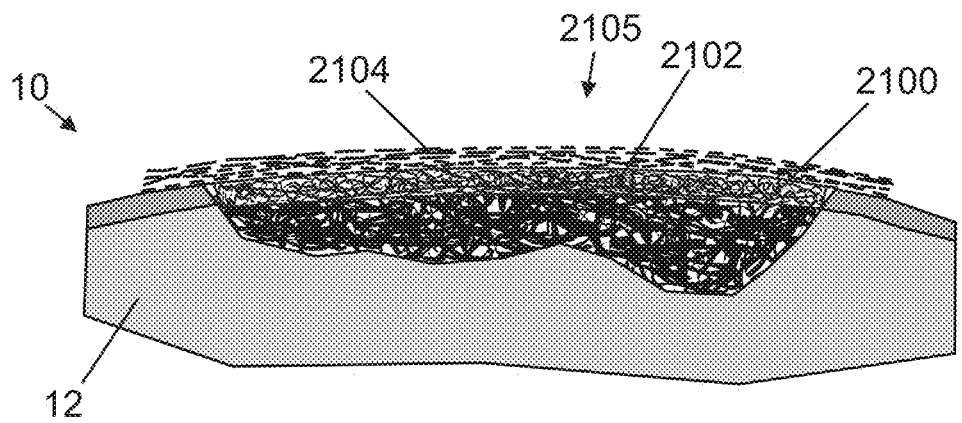
FIG. 80 shows the wound of FIG. 77 implanted with another embodiment of a multi-layered biomimetic tissue scaffold of the present invention formed of three uniquely configured layers, each containing bioribbons with nanofibers optimized for regeneration of a different tissue type.

FIGS. 75 and 76 depict a chronic wound 10 located on the foot of a patient. Sectional view 77 of wound 10 depicts its condition following debridement and cleansing to remove necrotic tissue and biofilm from surface 16 of tissue 12. Edges 18 have been debrided so that dermis 14 does not overhang tissue 16 and there are no barriers to the growth of epithelium across the wound. FIG. 78 depicts wound 10 with a biomimetic scaffold 2100 of the present invention positioned in the wound to facilitate tissue regeneration. In a preferred embodiment scaffold 2100 is a compressible non-woven mat formed of bioribbons having porosity and bioribbon characteristics optimal for regeneration of tissue to fill and seal wound 10. Following placement of scaffold 2100, the wound is treated in the usual manner with suitable dressings, etc. While scaffold 2100 is formed of bioribbons having a single nanofiber array configuration throughout, in other embodiments scaffolds of the present invention have a first portion optimized for regeneration of a first tissue type, and a second portion optimized for the regeneration of a second tissue type. Referring now to FIG. 79, scaffold 2103 has a first portion 2100 configured subdermal tissue, and a second portion 2102 optimized for the growth of dermal tissue. Scaffold 2105, show in FIG. 80, has three portions each optimized for the growth of a specific tissue type. In a preferred embodiment scaffold portion 2100 is a compressible non-woven mat of bioribbons optimally configured for subdermal tissue; portion 2102 is a non-woven mat/fabric of bioribbons optimally configured for dermal tissue; and portion 2104 is optimally configured for epidermal tissue. In some embodiments portion 2104 is formed of one or more layers of mesh 1590 depicted in FIGS. 64 through 67. In others portion 2104 is formed of a non-woven mat or fabric of bioribbons. Regardless of the construct, portions 2102 and 2104 are configured to provide a scaffold tuned to facilitate the attachment, migration and proliferation of unaffected skin cells at the wound margins.

Figure 81:
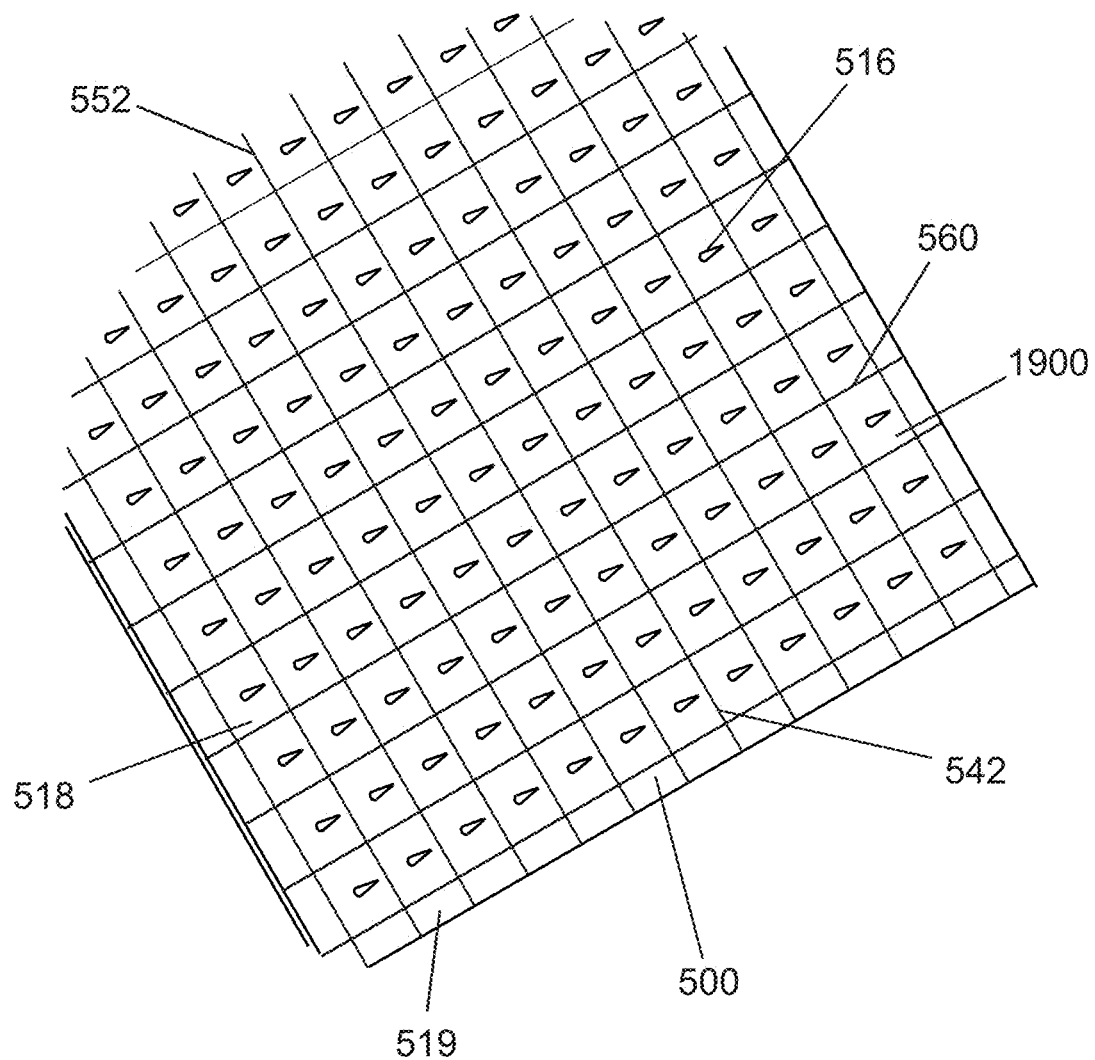
FIG. 81 is a perspective view of the elongate film element of FIG. 26 wherein lateral cuts are made so as to form a plurality of bioribbon segments.

FIG. 81 depicts the film segment of FIG. 26 wherein film strip 518 has formed therein slits 542 to create a plurality of bioribbons 519 of the present invention. In FIG. 81, lateral cuts 560 divide bioribbons 519 into short segments 1900. Lateral cuts 560 may be formed in ribbons 519 by a rotating cylindrical cutting element with axially oriented cutting edges formed on the circumferential surface of the elements. As with the forming slits 542 in strip 518, lateral cuts 560 may be formed by cooperative action between the cylindrical cutting element and a second cylinder as previously described. Transection of strip 518 by lateral cuts 560 creates a plurality of segments 1900, length 1905 of segment 1900 being determined by the spacing of cutting edges on the cylindrical cutting element.

Figure 82:
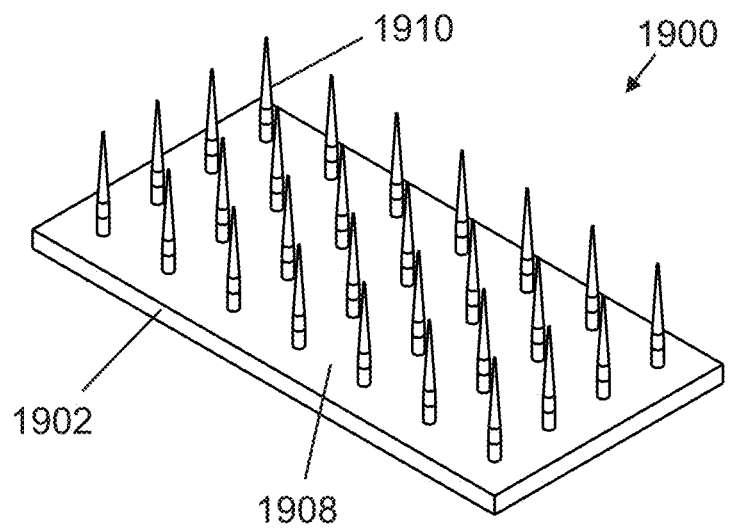
FIG. 82 is a perspective view of a bioribbon segment of FIG. 81.
Figure 83:
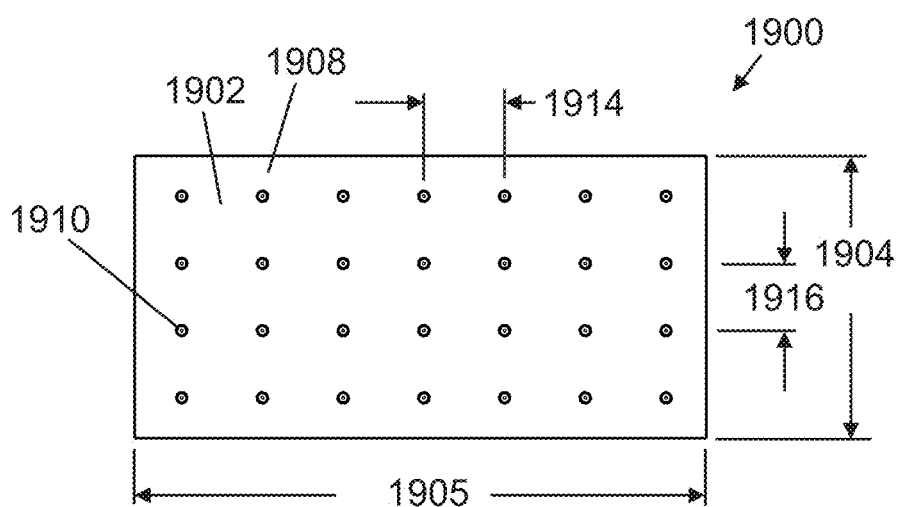
FIG. 83 is a plan view of the objects of FIG. 82.
Figure 84:
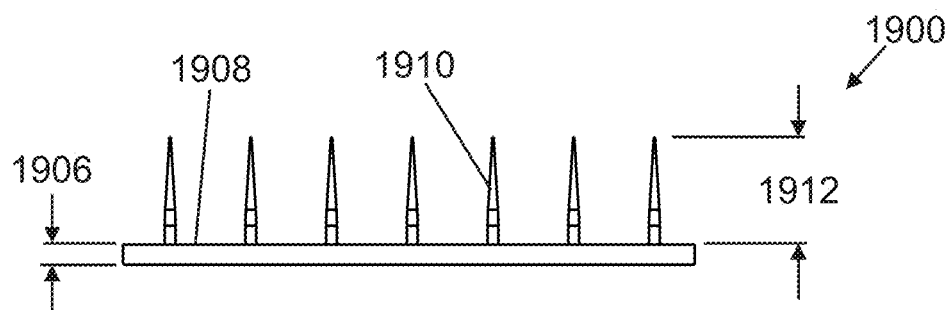
FIG. 84 is a side elevational view of the objects of FIG. 82.

Referring now to FIGS. 82 through 84, segment 1900 is identical to ribbon 100 in all aspects except as specifically hereafter described. Like ribbon 100, segment 1900 has arrays of nanofibers 1910 formed on first surface 1908 of film portion 1902. However, segment 1900 has a predetermined length 1905. In some embodiments length 1905 is 100× or greater than width 1904 of ribbon 1900. In other embodiments, length 1905 is between 10× and 100× width 1904 of ribbon 1900. In yet other embodiments, length 1905 is between 1× and 10× width 1904 of ribbon 1900. Length 1905 and width 1904 of segment 1900 may be optimized for the wound to be treated and/or method of delivery.

Figure 85:
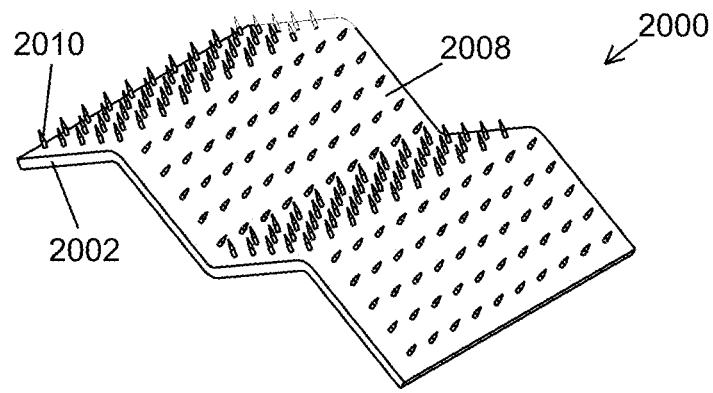
FIG. 85 is a perspective view of an embodiment of a bioribbon segment of the present invention having a non-planar shape.
Figure 86:
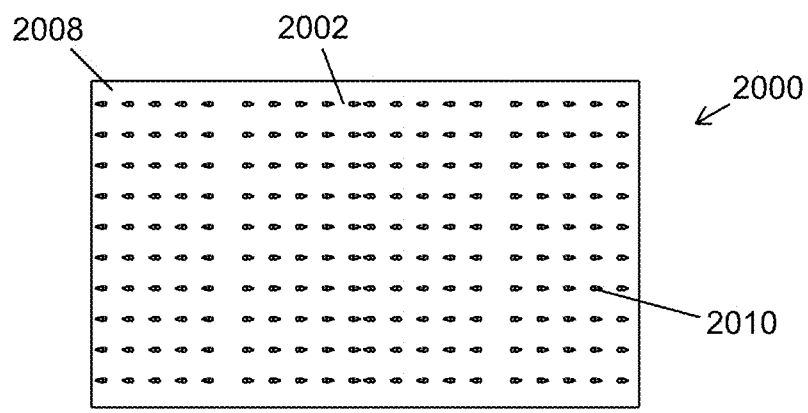
FIG. 86 is a plan view of the objects of FIG. 85.
Figure 87:
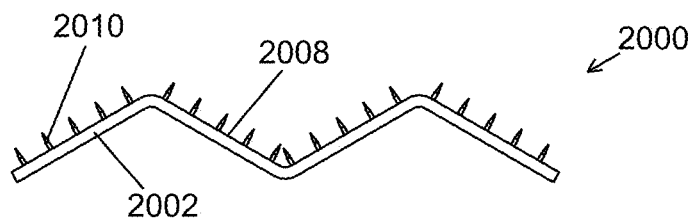
FIG. 87 is a side elevational view of the objects of FIG. 85.
Figure 88:
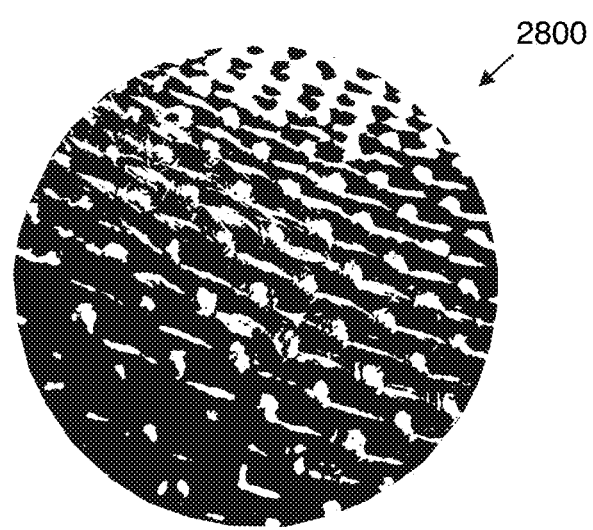
FIG. 88 is a perspective view of an embodiment of a biomimetic tissue scaffold in the form of a mat woven from yarn made from polymer bioribbons.

In certain embodiments ribbon segments may have a shape imparted to the film portion so that when the segments are assembled in a non-woven mat or introduced onto or into a wound, natural paths for cell propagation between segments are created. Referring now to FIGS. 85 through 87, segment 2000 is like segment 1900 with an array of nanofibers 2010 formed on first surface 2008 of film portion 2002. Film portion 2002 is not flexibly planar as in previously described embodiments, but rather has a form imparted thereto during manufacture. Forming of film portion 2002 in the manner depicted for segment 2000 may also be advantageously applied to elongate bioribbons of the present invention so as to aid in the creation of paths for cell propagation through the assembled tissue scaffold.

When viewed in a plan view, ribbon segments 1900 and 2000 have a rectangular shape imparted by the orthogonal cuts that formed them. In other embodiments formed by other slitting, cutting or chopping methods the shape of the ribbon segments may have other predetermined shapes, or may be randomly formed segments with irregular shapes. All fall within the scope of this invention.

Referring again to FIGS. 79 and 80, in some embodiments scaffold segment 2100 is formed of ribbon segments 1900 deposited in wound 10 prior to placing segment portion 2102. In some embodiments segments 1900 may be provided sterile and dry. In other embodiments segments 1900 may be provided as a suspension in a liquid selected for its therapeutic properties. Platelet-rich plasma (PRP) has been shown to be beneficial in the healing pressure ulcers and other chronic wounds. In some embodiments of the present invention bioribbon segments 1900 are mixed with platelet rich plasma or other suitable stem cell-rich fluid to form a viscous flowable suspension that can be implanted using a syringe. In other embodiments the consistency of the mixture is more paste-like so that rather than implanting with a syringe, the scaffold is implanted using a suitable hand instrument like a spatula packer. The beneficial healing properties of the fluid with which bioribbon segments 1900 are mixed may be enhanced by the addition of pluripotent stem cells. For instance, adipose derived stem cells (ASCs) may be easily harvested by liposuction and have a high differential potential. Pluripotent stem cells obtained from umbilical cord tissue have primitive properties and a rapid growth rate making them attractive as additives to a flowable scaffold. Cord blood and a gelatinous coating present within the cord commonly referred to as Wharton's Jelly both contain mesenchymal stem cells (MSCs). Because the umbilical cord is discarded after birth, there is no risk associated with stem cell collection. Bone marrow derived stem cells may also be used. Regardless of the source for the stem cells in the PRP or other fluid ingredient constituent in the flowable scaffold, the propagation will be enhanced by bioribbon segments 1900 forming the scaffold through the abundance site for cell adhesion, and cell differentiation will be substantially influenced by the arrangement of nanofibers forming arrays on bioribbon segments 1900, and by the properties of the nanofibers. The spacing of the nanofibers, and the length and stiffness of the nanofibers, may be selected to mimic the spacing and properties of fibrils of native ECM for the desired tissue type.

In a method of the present invention for treating a chronic wound using scaffolds formed of bioribbons, the surgeon debrides the wound in the usual manner to remove necrotic tissue and biofilm and remove overhanging tissue at the wound margins. Based on characteristics of the wound and the tissue to be regenerated, the surgeon selects a biomimetic scaffold of the present invention with nanofibers optimally configured for the desired tissue to be regenerated. For shallow wounds, the scaffold may have nanofibers of a single type. For instance, the scaffold may be formed of a non-woven mat or fabric 1600 shown in FIGS. 68 through 70 and FIG. 72, or may be formed of multiple layers of the mesh 1590 depicted in FIGS. 64 and 65. The nanofiber arrays on bioribbons of which these scaffolds are formed may be optimized for the differentiation and propagation of dermal cells. For deeper, more complex wounds, a biomimetic layered construct may be optimal with the outer layer optimized for the regeneration of dermal cells, and the underlying portions optimized for regeneration of subdermal cell types. Whatever the scaffold construction selected, the scaffold is implanted in the wound and secured by a suitable method. These methods may include suturing, skin staples, or a suitable adhesive like, for instance, BioGlue by CryoLife, Inc. (Kenesaw, Ga.) or a fibrin glue/sealant. Optionally, the scaffold may be infused with a PRP or another suitable fluid containing stem cells as previously described. After implantation of the scaffold, the site is covered with suitable dressings in the usual manner.

Tissue Augmentation

The use of scaffolds for the augmentation of tissue of various types is widely accepted. For instance, the Ossix family of scaffold products by Datum Dental Ltd. (Ness Ziona, Israel) are used for guided bone regeneration (GBR) and Guided tissue regeneration (GTR) to direct the growth of new bone and gingival tissue where this is required for implant and cosmetic dentistry. In cosmetic surgery, soft tissue volume replacement necessitated by aging or injury is facilitated by the use of appropriate tissue scaffolds. Scaffolds for tissue augmentation are widely used in the repair of tendons and ligaments, particularly when tears are large and the tissue is frayed due to degradation. The ArthroFLEX™ products by Arthrex, Inc. (Naples, Fla.) are decelluralized dermal allografts in which the donor DNA has been removed from the dermal matrix, to yield a biocompatible scaffold that retains its native collagen scaffold. The products are provided as flexible sheets of various thicknesses that may be trimmed as required for the specific application. The ArthroFLEX products are frequently used for the augmentation and reinforcement in the repair of rotator cuff tears when the cuff is thin, or the margins are frayed. They are also used to reinforce repairs to the Achilles tendon and other connective tissues throughout the body. The ArthroFLEX products are biomimetic in that they retain features of ECM of the dermal tissue and generally have a high rate of tissue ingrowth, however, like other biologic augmentation grafts their degradation may proceed at a suboptimal rate. Some biologic grafts may have biocompatibility variations that may lead to rejection, and/or a significant inflammatory response. The Artelon™ tissue reinforcement products by Artimplant AB, (Vastra Frolunda, Sweden) are Artelon (Artimplant) have a braided construct and are made of a synthetic polymeric material, the construct allowing the ingrowth of tissue in which it is implanted. The Artelon products retain their strength much longer than scaffolds formed of biologic materials and retain approximately fifty percent of their strength after four years. They are designed to degrade over the course of five to seven years as the host tissue replaces the majority of the graft material. The elasticity of the material is similar to that of the tendon or ligament that it is reinforcing. Because of this, shear forces are created in the ingrowing tissue that enhance cell propagation and development. The braided construction of the Artelon reinforcement products provides "pores" for the ingrowth of tissue, however, in other regards they do not mimic the native ECM. The scale of the braided material is substantially greater than the nano-scale features of the ECM to which cells attach.

Figure 14:
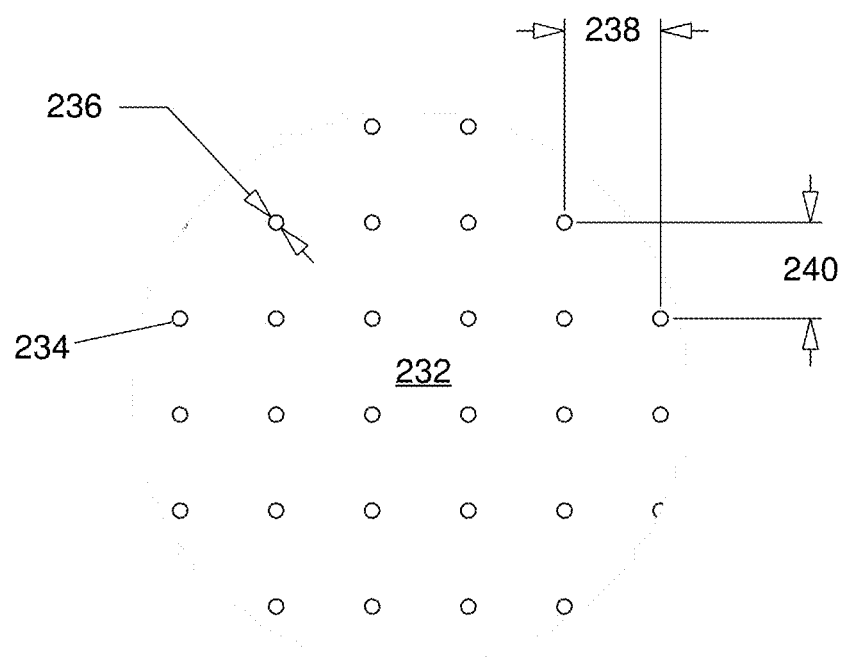
FIG. 14 is an expanded view of the objects of FIG. 11 at location B.
Figure 15:
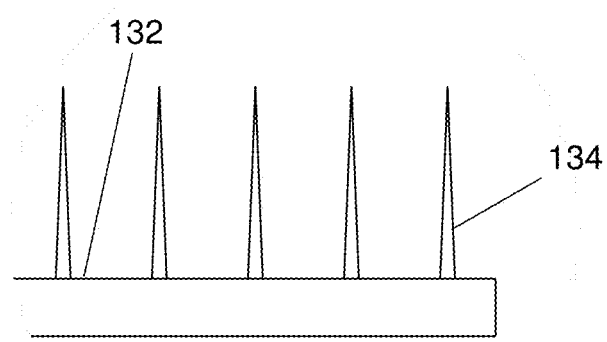
FIG. 15 is an expanded view of the objects of FIG. 12 at location C.

There is a need for a biomimetic scaffold for soft tissue reinforcement and augmentation with features optimal for differentiation and propagation of a preferred tissue type, and with tensile strength and elasticity to supplement the strength of the augmented tissue structure. Scaffolds of the present invention formed of bioribbons with biomimetic nanofiber arrays may be formed into a variety of constructs with properties that may be optimized to achieve specific tissue outcomes. Referring again to FIGS. 19 through 23 depicting bioribbon 400 of the present invention, width 420 and thickness 410 of film portion 402 may be chosen to provide stiffness, strength and resilience required to construct a biomimetic scaffold with properties that closely approximate that of the native tissue being augmented. These properties can be optimized without affecting the biomimetic properties of the nanofiber arrays formed on the ribbon. Referring to FIG. 14, diameter 236, and spacings 238 and 240 of nanofibers 234 are not affected by changes to the film portion 402 of ribbon 400, nor (referring to FIGS. 16 and 17) height 235, base diameter 233 or stiffness of nanofiber 234, or length 335, base diameter 333, or other form characteristics of nanofiber 331 depicted in FIG. 17. The stiffness, strength, and resiliency of a scaffold formed of bioribbons of the present invention may be further affected by the inclusion of bioribbons 800 (FIGS. 35 through 40) or bioribbons 900 (FIGS. 41 through 45).

Figure 71:
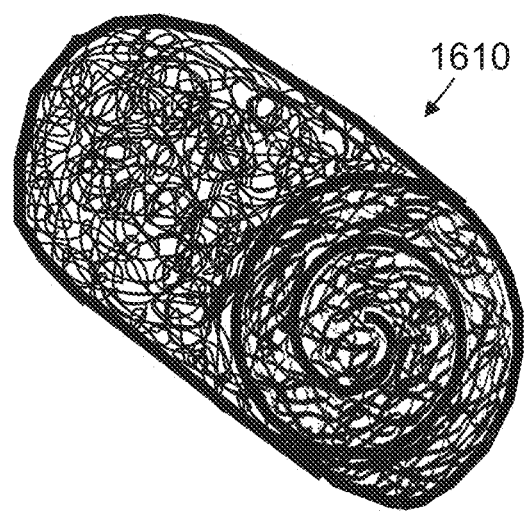
FIG. 71 is a perspective depiction of an embodiment of a cylindrical scaffold of the present invention formed by rolling the non-woven fabric of FIG. 70.
Figure 72:
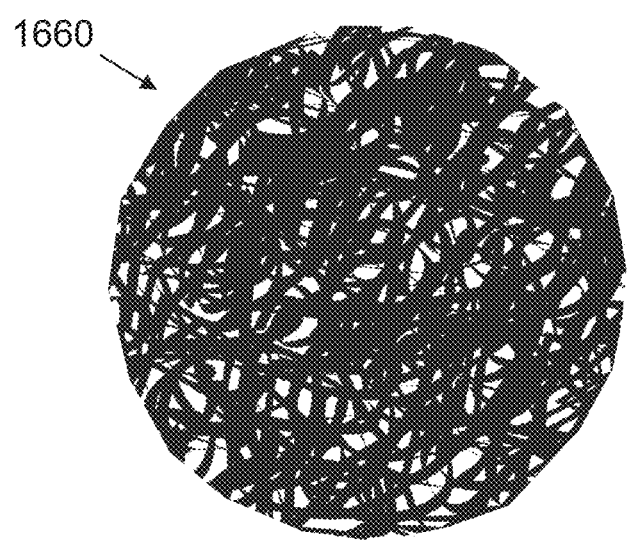
FIG. 72 is a plan view of another embodiment of a biomimetic tissue scaffold formed of the non-woven fabric of FIG. 70.

The physical properties of scaffolds of the present invention may be further affected by the orientation of bioribbons making up the scaffold. For instance, because of the random orientation of the ribbons of scaffold 1600 (FIGS. 68 through 70), the strength, stiffness and resiliency of scaffold 1600 in the X and Y directions will be equal. Scaffold 1000 depicted in FIGS. 51 to 53 has highly directional properties, the stiffness and rigidity in the axial direction being optimized for the growth of a selected tissue type in the interstitial spaces between bioribbons 1005, which as noted above can be bioribbons 800. Shear stresses applied to the propagating cells in these interstitial spaces are suitable/optimal for the tissue type. Another scaffold 1610 with highly directional properties is depicted in FIG. 71, which can be formed of a non-woven mat or fabric 1600 shown in FIGS. 68 through 70 rolled into a cylindrical body.

To summarize, when constructing biomimetic tissue scaffolds of the present invention, bioribbons in the scaffold have formed on them nanofiber arrays that may be optimized to affect a preferred cellular response—maintained stemness, differentiation into a selected cell type, preferred orientation, elongation, etc. These properties are independent of the physical characteristics of the bioribbons (stiffness, strength, resilience) that are determined by the ribbon material and physical dimension and form. These may be independently optimized to match the properties of the native tissue, to create optimal shear stresses within the scaffold, and to produce optimal properties in the tissue generated.

What is claimed is:

1. A tissue scaffold, comprising:
   a first plurality of coiled flexible polymeric ribbons, each ribbon of the first plurality having a surface on which is formed a first array of outwardly protruding nanofibers, wherein the first plurality of ribbons defines a tubular body having a first open end, a second open end, and a lumen extending between the first and second open ends; and
   a second plurality of flexible polymeric ribbons received in and extending axially through the lumen, each ribbon of the second plurality having a surface on which is formed a second array of outwardly protruding nanofibers.

2. The tissue scaffold of claim 1, wherein the first plurality of ribbons is arranged as a plurality of layers of coiled flexible polymeric ribbons.

3. The tissue scaffold of claim 2, wherein each layer supports or is supported by an adjacent layer.

4. The tissue scaffold of claim 3, wherein each layer has a handedness which differs from that of each adjacent layer.

5. The tissue scaffold of claim 4, further comprising a plurality of pores extending from an exterior surface of the tubular body to the lumen.

6. The tissue scaffold of claim 5, wherein the pores are at least partially defined by gaps between the ribbons of the first plurality forming adjacent layers.

7. A method of repairing an elongate tissue structure in need of repair, comprising:
providing a tissue scaffold of claim 1;
securing a first end of the elongate tissue structure in the first open end of the tissue scaffold; and
securing a second end of the elongate tissue structure in the second open end of the tissue scaffold.

8. The tissue scaffold of claim 1, wherein each ribbon of the second plurality of flexible polymeric ribbons is coterminous with each other ribbon of the second plurality of flexible polymeric ribbons.

9. The tissue scaffold of claim 1, wherein:
each ribbon of the second plurality of flexible polymeric ribbons has a first end and a second end;
the first ends of each ribbon of the second plurality of flexible polymeric ribbons are aligned;
the second ends of each ribbon of the second plurality of flexible polymeric ribbons are aligned;
the first ends of each ribbon of second plurality of flexible polymeric ribbons are coterminous with the open first end of the tubular body; and
the second ends of each ribbon of second plurality of flexible polymeric ribbons are coterminous with the open second end of the tubular body.

10. The tissue scaffold of claim 1, wherein the second plurality of flexible polymeric ribbons substantially fills the lumen such that each ribbon of the second plurality contacts at least one other ribbon of the second plurality.

11. A tissue scaffold, comprising:
a first layer comprising a first plurality of coiled flexible polymeric ribbons, each ribbon of the first plurality having a surface on which is formed a first array of outwardly protruding nanofibers, wherein the first layer defines a first open end, a second open end, and a lumen extending between the first and second open ends; and
a second plurality of flexible polymeric ribbons received in and extending axially through the lumen, each ribbon of the second plurality having a surface on which is formed a second array of outwardly protruding nanofibers.

12. The tissue scaffold of claim 11, further comprising:
a second layer comprising a third plurality of coiled flexible polymeric ribbons, each ribbon of the third plurality having a surface on which is formed a third array of outwardly protruding nanofibers;
wherein the second layer overlaps the first layer.

13. The tissue scaffold of claim 12, wherein:
each of the first and second layers has a handedness; and
the handedness of the first layer differs from that of the second layer.

14. The tissue scaffold of claim 13, further comprising:
a third layer comprising a fourth plurality of coiled flexible polymeric ribbons, each ribbon of the fourth plurality having a surface on which is formed a fourth array of outwardly protruding nanofibers;
wherein the third layer overlaps the second layer; and
wherein the third layer has a handedness which differs from that of the second layer.

15. A tissue scaffold, comprising:
a first plurality of flexible polymeric ribbons, each ribbon of the first plurality having a surface on which is formed a first array of outwardly protruding nanofibers, wherein the flexible polymeric ribbons of the first plurality are interlaced to form a tubular body defining a first open end, a second open end, and a lumen extending between the first and second open ends; and
a second plurality of flexible polymeric ribbons received in and extending axially through the lumen, each ribbon of the second plurality having a surface on which is formed a second array of outwardly protruding nanofibers.

16. The tissue scaffold of claim 15, wherein each ribbon of the first plurality is arranged to pass back and forth or over and under another ribbon of the plurality.

* * * * *